United States Patent
Pan et al.

(10) Patent No.: US 8,933,070 B2
(45) Date of Patent: Jan. 13, 2015

(54) METHODS OF TARGETING PTEN MUTANT DISEASES AND COMPOSITIONS THEREFOR

(75) Inventors: Guohua Pan, Oakville (CA); Jacqueline M. Mason, Toronto (CA); Xin Wei, Markham (CA); Miklos Feher, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 13/807,816

(22) PCT Filed: Jul. 4, 2011

(86) PCT No.: PCT/CA2011/000776
§ 371 (c)(1),
(2), (4) Date: Jan. 25, 2013

(87) PCT Pub. No.: WO2012/000103
PCT Pub. Date: Jan. 5, 2012

(65) Prior Publication Data
US 2013/0123273 A1    May 16, 2013

Related U.S. Application Data

(60) Provisional application No. 61/361,102, filed on Jul. 2, 2010.

(51) Int. Cl.
| | | |
|---|---|---|
| *A61K 31/553* | (2006.01) | |
| *A61K 31/00* | (2006.01) | |
| *A61K 31/535* | (2006.01) | |
| *C07D 273/00* | (2006.01) | |
| *C07D 211/00* | (2006.01) | |
| *A61K 31/495* | (2006.01) | |
| *A61K 31/416* | (2006.01) | |
| *A61K 31/4439* | (2006.01) | |
| *A61K 31/497* | (2006.01) | |

(52) U.S. Cl.
CPC ............ *A61K 31/495* (2013.01); *A61K 31/416* (2013.01); *A61K 31/4439* (2013.01); *A61K 31/497* (2013.01)
USPC .................. 514/211.09; 514/211; 514/234.5; 544/70; 544/230; 546/15; 548/357.5

(58) Field of Classification Search
CPC .. C07D 491/10; C07D 471/10; C07D 487/10; C07D 493/10; C07D 209/96; C07D 221/20; C07D 209/54; C07D 311/96; A61K 38/00; A61K 38/31; A61K 38/08; C07K 14/6555; C07K 14/655

USPC ................... 514/211.09, 234, 253, 278, 403; 544/70, 230; 546/15; 548/357.5
See application file for complete search history.

(56) References Cited

U.S. PATENT DOCUMENTS

2010/0016421 A1*   1/2010   Burger et al. ................ 514/456

FOREIGN PATENT DOCUMENTS

| CA | 2596967 A1 | 8/2006 |
|---|---|---|
| CA | 2631506 A1 | 1/2008 |
| CA | 2706075 A1 | 5/2009 |
| CA | 2732520 A1 | 2/2010 |
| WO | 2007109026 A2 | 9/2007 |
| WO | WO 2009/065232 * | 5/2009 |
| WO | WO-2009079767 A1 | 7/2009 |
| WO | 2010115279 A1 | 10/2010 |
| WO | 2011123946 A1 | 10/2011 |
| WO | 2012168721 A1 | 12/2012 |

OTHER PUBLICATIONS

Hollestelle et al (Breast Cancer Research and Treatment 121, 1(2009) 53-64).*
LoPiccolo et al., Crit. Rev. Oncol. Hematol. vol. 63, No. 3, 2007 p. 203-214.
Kobayashi et al., Oncol. Rep., vol. 22 No. 2, 2009 p. 233-240.
Pellegrino et al., Hepatology, vol. 51, No. 3, 2010 p. 857-868.
Min Sup Song et al., "Nuclear PTEN regulates the APC-CDH1 Tumor-Suppressive Complex in a Phosphate Independent Manner," Cell, Dec. 2010, vol. 144, No. 2, pp. 187-199, XP028152918.
Zhenbang Chen et al., "Crucial role of p53-dependent cellular senescence in suppression of Pten-deficient tumorigenesis," Nature, Aug. 2005, vol. 436, No. 7051, p. 725-730, XP055102190.

* cited by examiner

Primary Examiner — Shirley V Gembeh
(74) Attorney, Agent, or Firm — McCarter & English, LLP; Steven G. Davis; Wei Song

(57) ABSTRACT

Provided herein are methods, uses and compositions for treating a patient with cancer wherein the cancer is characterized by a PTEN gene mutation. In particular embodiments, the methods comprise administering to the patient a composition comprising a therapeutically effective amount of a PLK4 antagonist, and identifying a patient that is likely to be responsive to PLK4 antagonist therapy, if PTEN gene mutation is present.

17 Claims, 12 Drawing Sheets

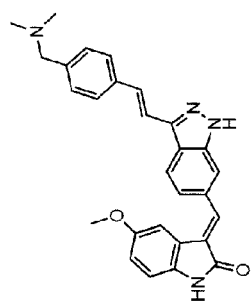
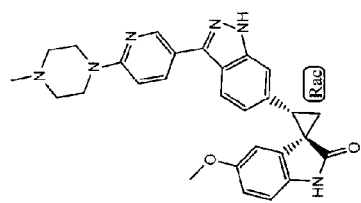
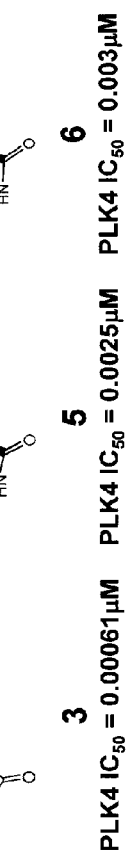
| CFI_ID | PLK4 IC$_{50}$, μM | | CFI_ID | PLK4 IC$_{50}$, μM |
|---|---|---|---|---|
| 1 | 0.00046 | | 11 | 0.013 |
| 2 | 0.00059 | | 12 | 0.026 |
| 3 | 0.00061 | | 13 | 0.047 |
| 4 | 0.0021 | | 14 | 0.048 |
| 5 | 0.0025 | | 15 | 0.057 |
| 6 | 0.003 | | 16 | 0.13 |
| 7 | 0.004 | | 17 | 0.25 |
| 8 | 0.0067 | | 18 | 13 |
| 9 | 0.0071 | | 19 (VX-680) | 0.017 |
| 10 | 0.0087 | | 20 (AG013736) | 0.046 |
FIG. 1A
FIG. 1B

21
PLK4 IC$_{50}$ = 0.00083 μM
MDA-MB-468 GI$_{50}$ < 0.01 μM
MDA-MB-231 GI$_{50}$ ~ 10 μM

Cells were treated with 21, and then subject to immunoblot analysis; GI$_{50}$s were measured by a 5 day SRB assay.

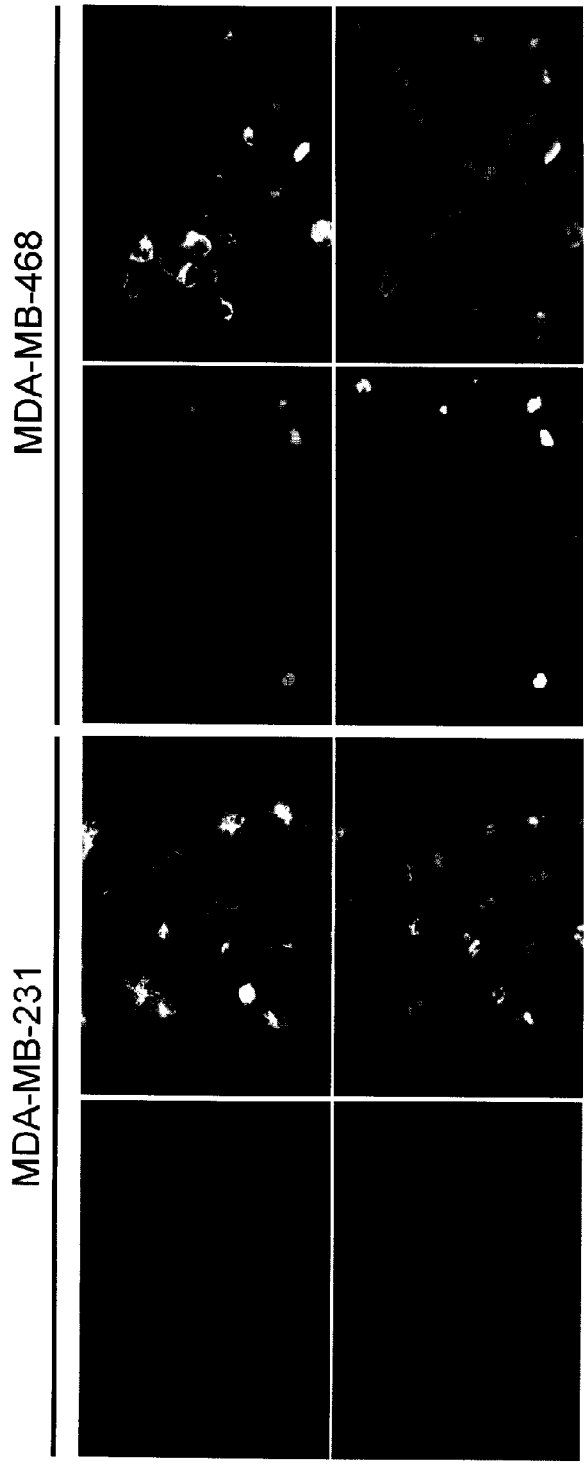
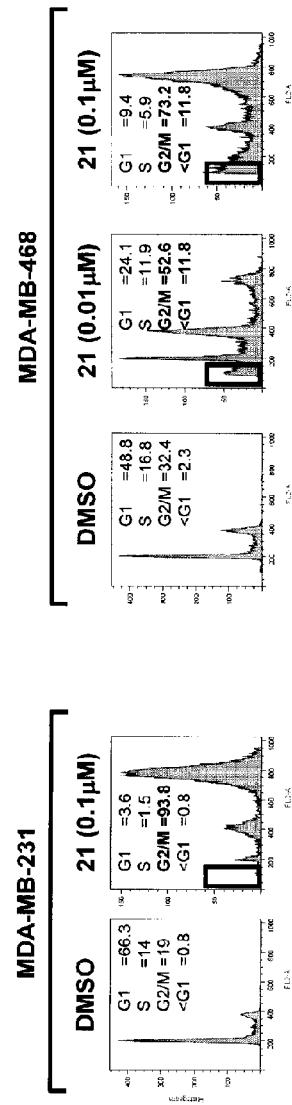
FIG. 5B
Cells were treated with 21 (0.1μM) for 3 days, and then subject to immunofluorescence analysis.
FIG. 5C
Cells were treated with 21 for 2 days, and then subject to cell cycle analysis.

Cells were treated with the indicated compounds for 5 days, and then subject to cell cycle analysis; $GI_{50}$s were measured by a 5 day SRB assay.

2 days after siRNA transfection, the cells were treated with 2 (0.5μM) for 2 days, and then subject to cell cycle analysis. Data is representative of three independent experiments.

METHODS OF TARGETING PTEN MUTANT DISEASES AND COMPOSITIONS THEREFOR

RELATED APPLICATIONS

The present application is a 35 U.S.C. §371 national stage filing of International Application No. PCT/CA2011/000776, filed Jul. 4, 2011, which, in turn, claims priority to U.S. Provisional Application Ser. No. 61/361,102, filed Jul. 2, 2010. The entire contents of this application are incorporated herein by this reference.

BACKGROUND OF THE INVENTION

PTEN (phosphatase and tensin homolog deleted on chromosome 10) is the protein which is encoded by the PTEN gene. The PTEN protein is found in almost all tissues in the body. PTEN is involved in the regulation of the cell cycle by preventing cells from growing and dividing too rapidly. The PTEN gene was identified as a tumor suppressor gene that is mutated in a large number of cancers at high frequency. These include cancers of the breast, prostate, endometrium, ovary, brain, skin, thyroid, lung, bladder and colon, as well as melanoma, glioblastoma. and lymphoma (Teng et al., Cancer Res. 57: 5221-5225, 1997) During tumor development, mutations and deletions of PTEN occur that inactivate its enzymatic activity leading to increased cell proliferation and reduced cell death. Genetic inactivation of PTEN occurs in glioblastoma, endometrial cancer, prostate cancer, and reduced expression is found in many other tumor types, such as lung and breast cancer.

PTEN mutations also cause a variety of inherited predispositions to cancer. For example, Cowden syndrome, Bannayan-Riley-Ruvalcaba syndrome, Proteus syndrome and Proteus-like syndrome. Together, the disorders caused by PTEN mutations are called PTEN hamartoma tumor syndromes, or PHTS. Mutations responsible for these syndromes cause the resulting protein to be nonfunctional or absent. The defective protein allows the cell to divide in an uncontrolled way and prevents damaged cells from dying, which can lead to the growth of tumors.

The prevalence of PTEN mutations in cancer underscores the significance of finding methods and compositions to treat, diagnose, and prevent such diseases. However, perhaps because of the many cellular biochemical reactions in which PTEN phosphatase activity is implicated in, or because of the nature of tumor suppressor genes, treatments that directly target PTEN activity or expression have had limited success. Thus, a need exists to develop new methods and compositions to identify patients suitable for treatment, treatments, diagnosis and prognosis of cancer and related diseases in which PTEN is mutated or lost.

SUMMARY OF THE INVENTION

The present teachings provide methods for treating a cancer patient. In particular, the cancer is characterized by a PTEN gene mutation. For example, the PTEN gene mutation results in reduced expression of PTEN as compared to a normal control, expression of a non-functional or limited functioning PTEN protein, or a loss of PTEN expression. Such cancers include breast cancer, prostate cancer, endometrial cancer, ovarian cancer, brain cancer, skin cancer, thyroid cancer, lung cancer, bladder cancer, colon cancer, melanoma, glioblastoma or lymphoma. In a particular embodiment, the cancer is a breast cancer selected from the subtypes: human epidermal growth factor receptor-2 (HER2)-overexpressing, luminal A, luminal B, and normal breast-like. In another embodiment, the cancer is a basal subtype breast cancer. The method of treating a patient with cancer, wherein said cancer is characterized by a PTEN gene mutation, comprises administering to the patient a composition comprising a therapeutically effective amount of a PLK4 antagonist. In one embodiment, the PLK4 antagonist is a small molecule inhibitor. In a particular embodiment, the small molecule inhibitor is selected from compounds 1-3, 5 and 6 as depicted in FIG. 1B, or a pharmaceutically acceptable salt thereof.

The present teachings also provide methods of identifying a patient that is likely to be responsive to PLK4 antagonist therapy. The method comprises providing a suitable sample from a cancer patient and determining PTEN expression in the sample, wherein if the sample is characterized by a PTEN mutation as compared with a suitable control then the patient is likely to be responsive to PLK4 antagonist therapy. In one embodiment, the patient is a cancer patient. For example, the cancer patient can have breast cancer, prostate cancer, endometrial cancer, ovarian cancer, brain cancer, skin cancer, thyroid cancer, lung cancer, bladder cancer, colon cancer, melanoma, glioblastoma or lymphoma. In a particular embodiment, the cancer is a basal subtype breast cancer. In a further embodiment, the method further comprises treating said patient with a PLK4 antagonist. In one embodiment, the PLK4 antagonist is a small molecule inhibitor. In a particular embodiment, the small molecule inhibitor is selected from compounds 1-3, 5 and 6 as depicted in FIG. 1B, or a pharmaceutically acceptable salt thereof. In a further embodiment, the method further comprises excluding a cancer patient for PLK4 antagonist therapy, wherein said excluded patient is negative for a PTEN mutation as compared with a suitable control.

Also provided by the teachings described herein are methods of treating a patient with breast cancer, wherein the breast cancer is characterized by a PTEN gene mutation. The method comprises administering to the patient a composition comprising a therapeutically effective amount of a PLK4 antagonist. In one embodiment, the breast cancer is selected from the subtypes: HER2-overexpressing, luminal A, luminal B, and normal breast-like. In another embodiment, the breast cancer is a basal subtype breast cancer. In a further embodiment, the breast cancer is estrogen receptor (ER) negative, human epidermal growth factor receptor-2 (HER2) negative, progesterone receptor (PR) negative, or a combination thereof. In one embodiment, the PLK4 antagonist is a small molecule inhibitor. In a particular embodiment, the small molecule inhibitor is selected from compounds 1-3, 5 and 6 as depicted in FIG. 1B, or a pharmaceutically acceptable salt thereof.

Also provided by the teachings described herein are methods of treating a patient with colon cancer, wherein the colon cancer is characterized by a PTEN gene mutation. The method comprises administering to the patient a composition comprising a therapeutically effective amount of a PLK4 antagonist. In one embodiment, the PLK4 antagonist is a small molecule inhibitor. In a particular embodiment, the small molecule inhibitor is selected from compounds 1-3, 5 and 6 as depicted in FIG. 1B, or a pharmaceutically acceptable salt thereof.

Also provided by the teachings described herein are methods of treating a patient with cancer, wherein the cancer is characterized by a PTEN gene mutation. The method includes identifying a patient that is likely to be responsive to PLK4 antagonist therapy; and administering to the patient a therapeutically effective amount of a PLK4 antagonist. In some embodiments, the patient likely to be responsive to PLK4 antagonist therapy is identified by providing a suitable sample from the patient; and determining PTEN expression in said sample; wherein if said sample is characterized by a PTEN mutation as compared with a suitable control then the patient is likely to be responsive to PLK4 antagonist therapy. For example, the PTEN gene mutation can result in reduced expression of PTEN as compared to a normal control, expression of a non-functional or limited functioning PTEN protein, or a loss of PTEN expression. Such cancers include breast cancer, prostate cancer, endometrial cancer, ovarian cancer, brain cancer, skin cancer, thyroid cancer, lung cancer, bladder cancer, colon cancer, melanoma, glioblastoma or lymphoma. In a particular embodiment, the cancer is a breast cancer selected from the subtypes: human epidermal growth factor receptor-2 (HER2)-overexpressing, luminal A, luminal B, and normal breast-like. In another embodiment, the cancer is a basal subtype breast cancer. In one embodiment, the PLK4 antagonist is a small molecule inhibitor. In a particular embodiment, the small molecule inhibitor is selected from compounds 1-3, 5 and 6 as depicted in FIG. 1B, or a pharmaceutically acceptable salt thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and 1B represent select PLK4 inhibitors of the present teachings. $GI_{50}$ data (i.e., the concentration of inhibitor that causes 50% growth inhibition) for over 33 breast cell lines were calculated for 20 PLK4 inhibitors. CFI_ID refers to the PLK4 inhibitor studied. FIG. 1B represents the chemical structures of particular PLK4 inhibitors of the present teachings (compounds 1-3, 5 and 6).

FIGS. 5A-5C illustrate how PLK4 inhibitor 21 induces cell death in the PTEN negative MDA-MB-468 breast cancer cell line, but not in the PTEN wild-type MDA-MB-231 breast cancer line. FIG. 5A depicts Western immunoblots showing levels of the cell death marker cleaved PARP in response to increasing concentrations of 21 in MDA-MB-231 and MDA-MB-468 cells (left panel), and a time course illustrating the induction of cleaved PARP in MDA-MB-468 cells from 0-36 hours after treatment with 0.03 μM of 21 (right panel). GAPDH levels are included as loading controls. The chemical structure of PLK4 inhibitor 21 is illustrated. FIG. 5B depict representative immunofluorescence photographs of MDA-MB-231 and MDA-MB-468 cells treated for 3 days with 0.1 μM PLK4 inhibitor 21. Staining for cleaved PARP, alpha-tubulin and DNA are shown in green, red and blue, respectively. FIG. 5C depict a series of FACS analyses showing the cell cycle profiles of MDA-MB-231 and MDA-MB-468 cells in response to treatment with PLK4 inhibitor 21 for 2 days. The percentage of cells in each cell cycle phase G1, S, G2/M and <G1 (sub-G1, which represents dead and dying cells, are boxed in red) is presented for the conditions indicated.

FIG. 8A are cell cycle analyses of cells transfected with either control siRNA (siCTRL) or siRNA targeting PTEN (siPTEN), and treated two days after transfection with either DMSO or 0.1 μM PLK4 inhibitor 21 for six days. The Western immunoblot confirmed knockdown of endogenous PTEN levels. The percentages of <G1 cells, indicative of cell death, were quantified and the averages from three separate experiments were shown. FIG. 8B are scatter plots from Annexin V/Propidium Iodide FACS analysis of control or PTEN siRNA-transfected MDA-MB-231 cells treated with DMSO or 0.1 μM PLK4 inhibitor 21 for 4 days. Counts of Annexin V-positive cells representing dead or apoptotic cells are boxed in red, while counts of Annexin V and propidium iodide double-negative cells, which constitute viable cells, are shown in the purple boxes.

DETAILED DESCRIPTION OF THE INVENTION

Figure 2:
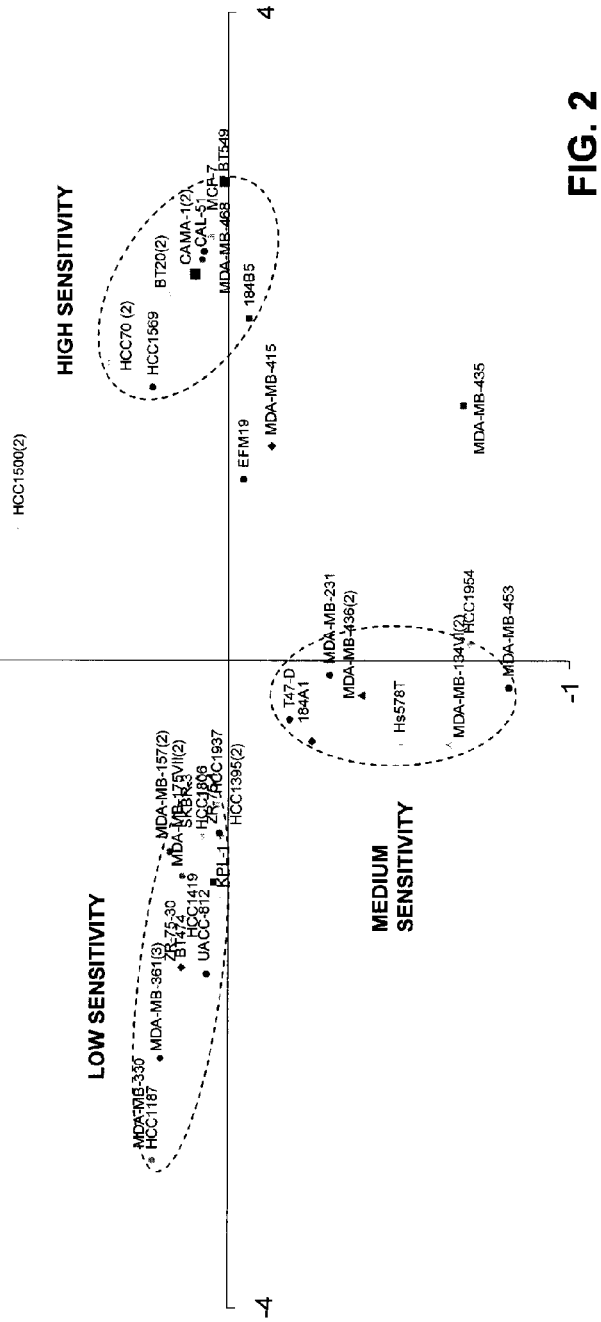
FIG. 2 is a scatter plot. The breast cancer cell lines studied clustered into three major groups: high sensitivity, medium sensitivity and low sensitivity to PLK4 inhibitors.

PTEN is involved in the regulation of the cell cycle by preventing cells from growing and dividing too rapidly. More specifically, PTEN is thought to act as a tumor suppressor by regulating several signaling pathways through the second messenger phosphatidylinositol 3,4,5 triphosphate (PIP3). PTEN is a dual-specific phosphatase that dephosphorylates the D3 position of PIP3 and down-regulates signaling events dependent on PIP3 levels (Maehama and Dixon, J Biol. Chem. 22: 13375-13378, 1998). PTEN catalyzes the reverse reaction of phosphatidylinositol 3-kinase (PI3K). The reversible phosphorylation of proteins and lipids is critical to the control of signal transduction in mammalian cells.

Mutations of the PTEN gene are found in a large number of human tumors. These include cancers of the breast, prostate, endometrium, ovary, brain, skin, thyroid, lung, bladder and colon, as well as melanoma, glioblastoma and lymphoma (Teng et al., Cancer Res. 57: 5221-5225, 1997). During tumor development, mutations and deletions of PTEN occur that inactivate its enzymatic activity leading to increased cell proliferation and reduced cell death. Genetic inactivation of PTEN occurs in glioblastoma, endometrial cancer, prostate cancer, and reduced expression is found in many other tumor types, such as lung and breast cancer.

PTEN mutations also cause a variety of inherited predispositions to cancer. For example, more than 70 mutations in the PTEN gene have been identified in people with Cowden syndrome. These mutations can be changes in a small number of base pairs, or in some cases, deletions of a large number of base pairs. Most of these mutations cause the PTEN gene to make a protein that does not function properly or does not work at all. The defective protein is unable to stop cell division or signal abnormal cells to die, which can lead to tumor growth, particularly in the breast, thyroid or uterus. Mutations in the PTEN gene cause several other disorders that, like Cowden syndrome, are characterized by the development of benign tumors called hamartomas. These disorders include Bannayan-Riley-Ruvalcaba syndrome, Proteus syndrome and Proteus-like syndrome. Together, the disorders caused by PTEN mutations are called PTEN hamartoma tumor syndromes or PHTS. Mutations responsible for these syndromes cause the resulting protein to be nonfunctional or absent. The defective protein allows the cell to divide in an uncontrolled way and prevents damaged cells from dying, which can lead to the growth of tumors.

PLK4 is a member of the polo-like kinase (PLK) family of serine/threonine kinases. The PLK family comprises at least five known members: PLK1, PLK2 (also known as Snk), PLK3 (also known as Fnk or Prk), PLK4 (also known as Sak) and PLK5. PLK1 is the best characterized member of the family, whereas PLK2, PLK3, PLK4 and PLK5 are less well characterized. Of the five members, PLK1, PLK2, and PLK3 all share a characteristic, highly conserved N-terminal catalytic domain and tandem C-terminal polo-box (PB) sequences that have a conserved function as phosphopeptide binding domains, which serve to localize the kinases and regulate their activity (Johnson et al., Biochemistry 46: 9551-9563, 2007, and references cited therein). PLK1 is a mitotic kinase and has been the target of therapeutic treatment of cancer (Johnson et al., Biochemistry 46: 9551-9563, 2007, and references cited therein).

PLK4 is the least understood and most divergent PLK family member. The N-terminal catalytic domain of PLK4 has a different substrate specificity from that of PLK1-3. PLK4 also has a divergent C-terminus comprising only a single polo-box sequence, not tandem PB sequences as in PLK1-3, that appears to act as a homodimerization domain rather than a localization domain (Lowery et al., Oncogene 24: 248-259, 2005).

PLK4 is involved in the control of mitotic entry and exit. It is a critical regulator of centrosome duplication (Habedanck et al., Nat. Cell Biol. 7: 1140-1146, 2005). PLK4 transcripts increase from S through M phase, and the protein is ubiquitylated and destroyed by the anaphase promoting complex (APC) (Hudson et al., Curr. Biol. 11: 441-446, 2001; Fode et al., Mol. Cell. Biol. 16: 4665-4672, 1996). PLK4 is required for late mitotic progression (Fode et al., PNAS 91: 6388-6392, 1994; Hudson et al., Curr. Biol. 11: 441-446, 2001), cell survival and postgastrulation embryonic development (Hudson et al., Curr. Biol. 11: 441-446, 2001). PLK4 knockout mice are embryonic lethal (E7.5), with a marked increase in mitotic and apoptotic cells (Hudson et al., Curr. Biol. 11: 441-446, 2001). PLK4 is transcriptionally repressed by p53 (Li et al., Neoplasia 7: 312-323, 2005). This repression is likely mediated through the recruitment of histone deacetylase (HDAC) repressors, and appears to contribute to p53-induced apoptosis (Li et al., Neoplasia 7: 312-323, 2005).

Described herein is the discovery that PLK4 inhibitors act synergistically on PTEN mutant cells to induce cell death. Thus, PLK4 inhibitors are useful in methods for treating cancers that are characterized by PTEN mutations.

Definitions

As used herein, a "therapy" is the administration of one or more therapeutic agents to a subject. A subject is any individual (e.g., a mammal, such as a primate (e.g., human), cow, sheep, goat, horse, dog, cat, rabbit, guinea pig, rat, mouse or other bovine, ovine, equine, canine feline, rodent or murine species) in need of therapy. Therapy can be the administration of a therapeutic agent in a single dose, in multiple doses, simultaneously with other agents, or sequentially with other agents. In addition, the one or more therapeutic agents can be administered to a subject at a particular dose (e.g., level, amount, mass) and on a particular schedule or at particular intervals (e.g., in increments of minutes, days, weeks, months, etc.).

A "therapeutic agent" is an agent which is used in a medical treatment, such as a therapy, e.g., to treat or cure a disease or condition, and/or to treat or alleviate a symptom, and/or to prevent or mitigate a disease or condition.

A "therapeutically effective amount" is an amount sufficient to achieve the desired therapeutic effect (such as a curing effect, treatment) under the conditions of administration. A therapeutically effective amount may also achieve a prophylactic effect under the conditions of administration.

An "anti-tumor effective amount" is an amount of an agent that is sufficient to directly inhibit tumor cell growth (e.g., inhibit tumor cell proliferation), inhibit tumor survival and/or promote tumor cell death.

An agent administered as a "primary therapy" is an agent that is the principal therapeutic agent in a therapy.

An adjunct therapy is another (e.g., secondary) therapy used together with the primary therapy, wherein the combination provides the desired treatment. Adjunct therapy is also known in the art as "adjunctive therapy".

An adjuvant therapy is a therapy given after the primary therapy to increase the chances of a cure. Adjuvant therapy may include chemotherapy, radiation therapy, hormone therapy, biological therapy and the like.

As used herein, "expression" (e.g., PLK4 expression, PTEN expression, etc.) means the expression (e.g., presence, absence, level, amount, etc.) of the nucleic acid sequence (e.g., mRNA), protein, and/or the activity of the protein (e.g., kinase activity, phosphatase activity, ability to bind substrate, ability to localize in the cell, etc.) in a sample. Negative expression means a lack of expression of the gene of interest, or expression of a non-functional protein. Expression can also mean the localization of the protein in a tissue sample (e.g., cellular localization).

An "antagonist" is an agent that binds the target molecule (e.g., PLK4), and inhibits one or more activities of the target molecule; or an agent that inhibits (e.g., reduces, prevents) the expression of the target molecule gene and/or protein. Thus, a "PLK4 antagonist" is an agent (e.g., small molecule, protein, peptide, polypeptide, peptidemimetic, non-peptidic molecule, antibody, siRNA molecule, antisense oligonucleotide, chemical compound, or a combination thereof) which specifically and preferably selectively binds PLK4, and inhibits one or more activities of PLK4; or an agent that inhibits (e.g., reduces, prevents) the expression of PLK4 gene and/or protein. Preferably, a PLK4 antagonist selectively binds or inhibits expression of PLK4 and, therefore, does not substantially bind other PLK family members (e.g., PLK1, PLK2, PLK3, PLK5, or a combination thereof) under physiological or therapeutic conditions. The terms antagonist and PLK4 antagonist are intended to include neutral and salt forms of the antagonist as well as anhydrous forms, hydrates and solvates thereof.

Methods for Identifying Patients for PLK4 Therapy

In one aspect, the present teachings provide a method for identifying a cancer patient candidate for anti-cancer therapy using a PLK4 antagonist, wherein the cancer is characterized by a PTEN mutation. As used herein, "characterized by a PTEN mutation" means that the cancer contains or comprises cancerous cells that have a PTEN mutation in the gene sequence that results in reduced expression of PTEN, expression of a non-functional or limited functioning PTEN protein, or lacks (so called "negative") expression of PTEN protein in the cell. The method comprises providing a suitable sample from the patient (e.g., a tumor sample, a cancer tissue sample) and determining the PTEN expression in the sample. A sample characterized by a PTEN mutation, e.g., exhibiting decreased (low) or negative PTEN expression in the sample relative to a suitable control indicates that the cancer patient is a candidate for anti-cancer therapy using a PLK4 antagonist. In one embodiment is a method for identifying a breast cancer patient candidate for anti-cancer therapy using a PLK4 antagonist. The method comprises providing a suitable sample from the patient (e.g., a tumor sample, a breast cancer sample) and determining the PTEN expression in the sample. Decreased (low) or negative PTEN expression in the sample relative to a suitable control indicates that the breast cancer patient is a candidate for anti-cancer therapy using a PLK4 antagonist.

A suitable sample can be obtained for example by cell or tissue biopsy. A sample can also be obtained from other tissues, bodily fluids and products, e.g., from a blood sample, spinal tap, feces, tissue smear, tissue scrape, and the like. Thus, the sample can be a biopsy specimen (e.g., tumor, polyp, mass (solid, cellular)), aspirate, smear, fecal sample and/or blood sample. The sample can be from a tissue that has a tumor (e.g., cancerous growth) and/or tumor cells, or is suspected of having a tumor and/or tumor cells. For example, a tumor biopsy can be obtained in an open biopsy, a procedure in which an entire (excisional biopsy) or partial (incisional biopsy) mass is removed from a target area. Alternatively, a tumor sample can be obtained through a percutaneous biopsy, a procedure performed with a needle-like instrument through a small incision or puncture (with or without the aid of a imaging device) to obtain individual cells or clusters of cells (e.g., a fine needle aspiration (FNA)) or a core or fragment of tissues (core biopsy). The biopsy samples can be examined cytologically (e.g., smear), histologically (e.g., frozen or paraffin section) or using any other suitable method (e.g., molecular diagnostic methods). A tumor sample can also be obtained by in vitro harvest of cultured human cells derived from an individual's tissue. Tumor samples can, if desired, be stored before analysis by suitable storage means that preserve a sample's protein and/or nucleic acid in an analyzable condition, such as quick freezing, or a controlled freezing regime. If desired, freezing can be performed in the presence of a cryoprotectant, for example, dimethyl sulfoxide (DMSO), glycerol, or propanediol-sucrose. Tumor samples can be pooled, as appropriate, before or after storage for purposes of analysis.

Determining or assessing gene expression can be performed using any suitable method, such methods are routine in the art. For example, screening a BAC array data set, quantitative polymerase chain reaction (QPCR), including quantitative real-time PCR, in situ hybridization, western blot analysis, immunohistochemical staining, kinase assays, and the like. Other such methods to detect a protein or peptide encoded by the gene of interest can include immunological and immunochemical methods like flow cytometry (e.g., FACS analysis), enzyme-linked immunosorbent assays (ELISA), including chemiluminescence assays, radioimmunoassay, and immunohistology, or other suitable methods such as mass spectroscopy. For example, antibodies to PTEN can be used to determine the presence and/or expression level of PTEN in a sample directly or indirectly using, for instance, immunohistology. For instance, paraffin sections can be taken from a biopsy, fixed to a slide and combined with one or more antibodies by suitable methods.

Methods to characterize a PTEN mutation, such as detecting, sequencing, analyzing a PTEN gene or expression thereof (e.g., DNA, mRNA) include PTEN nucleic acid amplification and/or visualization. To detect a PTEN gene or expression thereof, nucleic acid can be isolated from an individual by suitable methods which are routine in the art (see, e.g., Sambrook et al. Molecular Cloning, 1989). Isolated nucleic acid can then be amplified (by e.g., polymerase chain reaction (PCR) (e.g., direct PCR, quantitative real time PCR, reverse transcriptase PCR), ligase chain reaction, self sustained sequence replication, transcriptional amplification system, Q-Beta Replicase, or the like) and visualized (by e.g., labeling of the nucleic acid during amplification, exposure to intercalating compounds/dyes, probes). PTEN gene or expression thereof can also be detected using a nucleic acid probe, for example, a labeled nucleic acid probe (e.g., fluorescence in situ hybridization (FISH)) directly in a paraffin section of a tissue sample taken from, e.g., a tumor biopsy, or using other suitable methods. PTEN gene or expression thereof can also be assessed by Southern blot or in solution (e.g., dyes, probes). Further, a gene chip, microarray, probe (e.g., quantum dots) or other such device (e.g., sensor, nanonsensor/detector) can be used to detect expression and/or differential expression of a PTEN gene.

A sample characterized by a PTEN mutation, e.g., decreased or negative PTEN expression in a sample as compared with a suitable control indicates that the patient is a candidate for PLK4 antagonist therapy. Likewise, a sample not characterized by a PTEN mutation indicates that the patient may not be a candidate for PLK4 antagonist therapy and/or that the patient is a candidate for an anti-cancer therapy other than PLK4 antagonist therapy. PTEN expression in a tissue sample, such as a cancer tissue sample, can be compared with a suitable control. Suitable controls are well recognized in the art and include, for example, normal cells or a non-neoplastic tissue sample such as one isolated from the donor of the cancer tissue sample, non-cancerous cells, non-metastatic cancer cells, non-malignant (benign) cells or the like, or any other suitable known or determined standard. In addition, the control can be a known or pre-determined typical, normal or normalized range or level of expression of a PTEN protein or gene (e.g., an expression standard). Thus, the methods of the present teachings do not require that expression of the gene and/or protein be separately assessed in a suitable control each time a suitable sample from a patient is assessed for PTEN expression. Instead, whether PTEN expression in a sample is decreased or absent can be determined using prior knowledge or comparison with a known or pre-determined typical, normal or normalized range or level of expression of a PTEN protein or gene, such as a standard. Thus, PTEN expression can be compared to its expression in a known or a determined standard or it can be determined whether PTEN expression is below a threshold, typical, normal, or normalized level. In one embodiment, a suitable control is a normal breast tissue sample obtained from the same donor of the breast cancer tissue sample.

In one embodiment, provided is a method for selecting a cancer patient for PLK4 therapy, wherein a suitable sample from said patient is characterized by a PTEN mutation. The method can further comprise treating said patient selected for PLK4 therapy with a PLK4 antagonist. Additionally or alternatively, the method further comprises excluding a cancer patient for therapy, wherein said excluded patient is negative for a characteristic of a PTEN mutation. In a further embodiment, provided is a method for selecting a cancer patient for therapy other than PLK4 therapy, wherein a suitable sample from said patient is not characterized by a PTEN mutation. The method can further comprise treating said patient selected for therapy with an anti-cancer agent other than a PLK4 antagonist.

In another embodiment, provided is a method for selecting a breast cancer patient for PLK4 therapy, wherein the patient is or has been diagnosed with a basal subtype breast cancer. The method comprises selecting a breast cancer patient, wherein a suitable sample from said patient is characterized by a PTEN mutation. The method can further comprise treating said patient selected for PLK4 therapy with a PLK4 antagonist. Additionally or alternatively, the method further comprises excluding a breast cancer patient for therapy, wherein said excluded patient is negative for a characteristic of a PTEN mutation.

In another aspect, a method is provided for identifying a patient that will be responsive to PLK4 antagonist therapy. The method comprises providing a suitable sample, e.g., a tissue sample, a tumor sample, from the patient and characterizing said sample for a PTEN mutation (e.g., determining PTEN expression) in the sample. A sample characterized by a PTEN mutation, e.g., decreased or negative PTEN expression in the sample, as compared with a suitable control indicates that the patient will be responsive to PLK4 antagonist therapy. In one embodiment, the tissue sample is a breast tissue sample and the patient has breast cancer. For example, the patient that has breast cancer has a basal subtype breast cancer.

Antagonists

As described above, a "PLK4 antagonist" is an agent (e.g., small molecule, protein, peptide, polypeptide, peptidemimetic, non-peptidic molecule, antibody, siRNA molecule, antisense oligonucleotide, chemical compound, or a combination thereof) which specifically and preferably selectively binds PLK4, and inhibits one or more activities of PLK4; or an agent that inhibits (e.g., reduces, prevents) the expression of PLK4 gene and/or protein. A PLK4 antagonist can, for example, inhibit binding of a ligand or substrate (e.g., ATP) to PLK4. A PLK4 antagonist can inhibit the activity of a PLK4 in response to ligand or substrate binding. A PLK4 antagonist that inhibits the expression and/or activity of PLK4 can be, for example, a natural or synthetic nucleic acid or nucleic acid analog, antisense molecule, small interfering RNA (siRNA), short hairpin RNA (shRNA), protein, peptide, peptidomimetic, antibody, chemical compound or the like. Preferably, a PLK4 antagonist selectively binds or inhibits expression of PLK4 and, therefore, does not substantially bind other PLK family members (e.g., PLK1, PLK2, PLK3 and/or PLK5) under physiological or therapeutic conditions. The term PLK4 antagonist is intended to include neutral and salt forms of the antagonist as well as anhydrous forms, hydrates and solvates thereof.

A composition comprising a PLK4 can be used in such a screen or binding assay to detect and/or identify agents that can bind to a PLK4. Compositions suitable for use include, for example, cells which naturally express a PLK4. Agents which bind PLK4 can be further evaluated for PLK4 antagonist activity.

An agent that binds a PLK4 can be identified in a competitive binding assay, for example, in which the ability of a test agent to inhibit the binding of a reference agent (e.g., a ligand or substrate) is assessed. The reference agent can be labeled with a suitable label (e.g., radioisotope, epitope label, affinity label (e.g., biotin and avidin or streptavidin), spin label, enzyme, fluorescent group, chemiluminescent group, dye, metal (e.g., gold, silver), magnetic bead) and the amount of labeled reference agent required to saturate the PLK4 in the assay can be determined. The specificity of the formation of the complex between the PLK4 and the test agent can be determined using a suitable control (e.g., unlabeled agent, label alone).

The capacity of a test agent to inhibit formation of a complex between the reference agent and a PLK4 can be determined as the concentration of test agent required for 50% inhibition ($IC_{50}$ value) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent.

An agent which binds a PLK4 can be further studied to assess the ability of that agent to antagonize (reduce, prevent, inhibit) one or more functions of the PLK4. Functional characteristics of a PLK4 include binding activities (e.g., ligand or substrate binding), kinase activity (e.g., phosphorylation of a substrate) and/or an ability to stimulate a cellular response (e.g., mitosis). Such assays are standard in the art (see, e.g., Johnson et al., Biochemistry 46: 9551-9563, 2007 for a description of kinase assays for assessing activity of PLK1, PLK2, PLK3 or PLK4). For example, the agent can be incubated with PLK4 (purified, recombinant, or the like), in the presence of a suitable substrate (such as a peptide substrate, which can be labeled with a suitable label, e.g., an epitope label, an affinity label, such as biotin, avidin, streptavidin, and the like, magnetic bead, etc.) under conditions suitable for kinase activity. Suitable conditions include the presence of a kinase reaction buffer, with ATP. The ATP can be suitably labeled, e.g., with a radioisotope, epitope label, affinity label (e.g., biotin, avidin, streptavadin), spin label, enzyme, fluorescent group, chemiluminescent group, dye, metal (e.g., gold, silver), magnetic bead, or the like. Following incubation of the agent with PLK4, substrate and ATP, phosphorylation of the substrate can be assessed, e.g., by determining the amount of label from the ATP has transferred to the substrate. Alternatively, a phosphorylated substrate can be detected using a phospho-specific antibody. The substrate peptide: TPSDSLIYDDGLS (SEQ ID NO: 15) can be used to selectively assay PLK4 activity (see Johnson et al., Biochemistry 46: 9551-9563, 2007).

A PLK4 antagonist can be, for example, a small molecule, which can be found in nature (e.g., identified, isolated, purified) and/or artificially produced (e.g., synthesized). Small molecules can be tested for PLK4 binding specificity in a screen for example, a high-throughput screen of chemical compounds and/or libraries (e.g., chemical, peptide, nucleic acid libraries). Compounds or small molecules can be identified from numerous available libraries of chemical compounds from, for example, the Chemical Repository of the National Cancer Institute, the Molecular Libraries Small Molecules Repository (PubChem) and other libraries that are commercially available. Examples of small molecule antagonists of PLK, including PLK4, are described in Johnson et al., Biochemistry 46: 9551-9563, 2007 (see also FIG. 1B). Such libraries or collections of molecules can also be prepared using well-known chemical methods, such as well-known methods of combinatorial chemistry. The libraries can be screed to identify compounds that bind and inhibit PLK4. Identified compounds can serve as lead compounds for further diversification using well-known methods of medicinal chemistry. For example, a collection of compounds that are structural variants of the lead can be prepared and screened for PLK4 binding and/or inhibiting activity. This can result in the development of a structure activity relationship that links the structure of the compounds to biological activity. Compounds that have suitable binding and inhibitory activity can be further developed for in vivo use.

Exemplary small molecule antagonists of PLK, including PLK4, are described in U.S. Pat. No. 7,528,142; U.S. Pat. No. 7,622,463; U.S. Pat. No. 7,763,629; U.S. Pat. No. 7,829,590; U.S. Pat. No. 7,851,491; U.S. Pat. No. 7,915,305; U.S. Pat. No. 7,838,517; WO 09/079,767; and WO 10/115,279. The contents of these applications are incorporated herein by reference in their entireties.

In one embodiment, small molecule PLK4 antagonists include compounds represented by Structural Formula (I) or (I'):

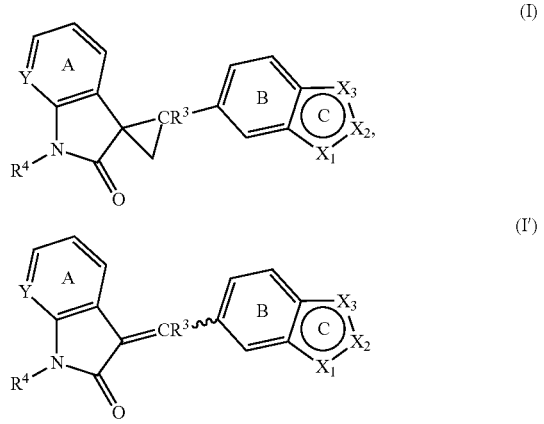

or a pharmaceutically acceptable salt thereof.

Ring A is optionally and independently substituted with one or more substituents represented by $R^a$ and ring B is optionally and independently substituted with one or more substitutents represented by $R^b$;

ring C is a 5-membered heteroaromatic ring wherein one of $X_1$-$X_3$ is N, one of $X_1$-$X_3$ is $NR^5$, and one of $X_1$-$X_3$ is N or $CR^6$;

Y is independently N, CH or $CR^a$;

each of $R^a$ and $R^b$ independently is:

halogen, —C(O)OR$^1$, —C(O)R$^1$, —C(S)R$^1$, —OC(O)R$^1$—, —C(O)NR$^1$R$^2$, —C(S)NR$^1$R$^2$, —OC(O)NR$^1$R$^2$, —S(O)R$^1$, —S(O)$_2$R$^1$, —SO$_3$R$^1$, —SO$_2$NR$^1$R$^2$, —OR$^1$, —SR$^1$, —NR$^1$R$^2$, —NR$^2$C(O)R$^1$, —NR$^2$S(O)R$^1$, —NR$^2$C(O)OR$^1$, —NR$^2$C(O)ONR$^1$R$^2$, —N(R$^2$)C(O)NR$^1$R$^2$, —NR$^2$SO$_2$NR$^1$R$^2$, —NR$^2$SO$_2$R$^1$; —NO$_2$, —CN, —NCS; or two ortho $R^a$ groups taken together form —O—[CH$_2$]$_p$—O—, —S—[CH$_2$]$_p$—S— or —[CH$_2$]$_q$—; or $C_{1-10}$ aliphatic group optionally substituted with one or more substituents selected from the group consisting halogen, nitro, cyano, —N(R$^{21}$)$_2$, —C(O)N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, —NR$^{21}$SO$_2$R$^{22}$, —NR$^{21}$C(O)OR$^{21}$, —OC(O)N(R$^{21}$)$_2$, —NR$^{21}$C(O)N(R$^{21}$)$_2$, —NRC(O)ON(R)$_2$, —NR$^{21}$SO$_2$N(R$^{21}$)$_2$, —OR$^{21}$, —SR$^{21}$, $C_{1-10}$ haloalkoxy, —C(O)R$^{21}$, —C(O)OR$^{21}$ and —OC(O)R$^{21}$; or ($C_{0-10}$ alkylene)-Ar$^1$, ($C_{2-10}$ alkenylene)-Ar$^1$, wherein Ar$^1$ is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, —N(R$^{21}$)$_2$, —C(O)N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, —NR$^{21}$SO$_2$R$^{22}$, —NR$^{21}$C(O)N(R$^{21}$)$_2$, —NRC(O)ON(R)$_2$, —NR$^{21}$SO$_2$N(R$^{21}$)$^2$, —OR$^{21}$, —SR$^{21}$, $C_{1-10}$ haloalkoxy, —C(O)R$^{21}$, —C(O)OR$^{21}$, —OC(O)R$^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^1$ independently is:

i) hydrogen;

ii) a $C_{6-14}$ aryl group or a 5-14 membered heteroaryl group, each optionally and independently substituted with one or more substituents selected from the group consisting of halogen, —NO$_2$, —CN, —NCS, aliphatic, ($C_{1-10}$ alkylene)-Ar$^{10}$, ($C_{2-10}$ alkenylene)-Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$; or iii) a $C_{1-10}$ aliphatic group optionally substituted with one or more substituents selected from the group consisting of halogen, —NO$_2$, —CN, —NCS, Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$, provided that R$^1$ is other than hydrogen when R$^a$ or R$^b$ is —S(O)R$^1$, —S(O)$_2$R$^1$, —SO$_3$R$^1$, —NR$^2$S(O)R$^1$ or —NR$^2$SO$_2$R$^1$; and each R$^2$ independently is —H or C$_1$-C$_6$ alkyl, or, taken together with NR$^1$, forms a non-aromatic heterocyclic group optionally substituted with one or more substituents selected from the group consisting of =O, =S, halogen, nitro, cyano, hydroxy, C$_{1-6}$ alkyl, C$_{1-6}$ haloalkyl, C$_{1-6}$ hydroxyalkyl, amino, C$_{1-6}$ alkylamino, C$_{1-6}$ dialkylamino, C$_{1-6}$ aminoalkyl, (C$_{1-6}$ alkylamino)C$_{1-6}$ alkyl, (C$_{1-6}$ dialkylamino)C$_{1-6}$ alkyl, (phenyl)C$_{1-6}$ alkyl, (5-6 membered heteroaryl)C$_{1-6}$ alkyl, C$_{1-6}$ alkoxy, C$_{1-6}$ haloalkoxy, C$_{1-6}$ alkylcarbonyloxy, C$_{1-6}$ alkoxycarbonyl, C$_{1-6}$ alkylcarbonyl, phenyl and 5-6 membered heteroaryl;

R$^3$ is —H, halogen, C$_{1-6}$ alkyl or C$_{1-6}$ haloalkyl;

each of R$^4$ and R$^5$ independently is —H, C$_{1-6}$ alkyl, phenyl, —C(O)(C$_{1-6}$ alkyl), —C(O)(phenyl), —C(O)O(C$_{1-6}$ alkyl), —C(O)O(phenyl), —S(O)$_2$(C$_{1-6}$ alkyl) or —S(O)$_2$(phenyl), wherein each alkyl in the groups represented by R$^4$ and R$^5$ independently is optionally substituted with one or more substituents selected from the group consisting of halogen, hydroxy, nitro, cyano, amino, phenyl, 5-6 membered heteroaryl, C$_{1-6}$ alkoxy and C$_{1-6}$ haloalkoxy, and wherein each phenyl in the groups represented by R$^4$ and R$^5$ independently is optionally substituted with one or more substituents selected from the group consisting of halogen, hydroxy, nitro, cyano, amino, C$_{1-6}$ alkyl, C$_{1-6}$ haloalkyl, C$_{1-6}$ alkoxy and C$_{1-6}$ haloalkoxy;

R$^6$ is hydrogen, halogen, nitro, cyano, R', —OR, —SR, —N(R)$_2$, —C(O)R, —C(O)OR, —OC(O)R, —C(O)N(R)$_2$, —OC(O)N(R)$_2$, —NRC(O)R, —NRC(O)OR, —SOR', —SO$_2$R', —SO$_3$R', —SO$_2$N(R)$_2$, —NRS(O)R', —NRSO$_2$R', —NRC(O)N(R)$_2$, —NRC(O)ON(R)$_2$, or —NRSO$_2$N(R)$_2$;

each R$^{10}$ independently is:

i) hydrogen;

ii) a C$_{6-14}$ aryl group or a 5-14 membered heteroaryl group, each optionally and independently substituted with one or more substituents selected from the group consisting of halogen, nitro, cyano, hydroxy, C$_{1-10}$ alkyl, C$_{1-10}$ haloalkyl, (C$_{1-10}$ haloalkoxy)C$_{1-10}$ alkyl, (C$_{1-10}$ alkoxy) C$_{1-10}$ alkyl, C$_{1-10}$ hydroxyalkyl, C$_{1-10}$ aminoalkyl, (C$_{1-10}$ alkylamino)C$_{1-10}$ alkyl, (C$_{1-10}$ dialkylamino) C$_{1-10}$ alkyl, (phenyl)C$_{1-10}$ alkyl, (5-6 membered heteroaryl)C$_{1-10}$ alkyl, amino, C$_{1-10}$ alkylamino, C$_{1-10}$ dialkylamino, C$_{1-10}$ alkoxy, C$_{1-10}$ haloalkoxy, alkylcarbonyloxy, C$_{1-10}$ alkoxycarbonyl and C$_{1-10}$ alkylcarbonyl; or iii) a C$_{1-10}$ alkyl group optionally substituted with one or more substituents selected from the group consisting of halogen, nitro, cyano, hydroxy, C$_{1-10}$ haloalkyl, C$_{1-10}$ alkoxy, C$_{1-10}$ haloalkoxy, amino, C$_{1-10}$ alkylamino, C$_{1-10}$ dialkylamino, C$_{1-10}$ alkylcarbonyloxy, C$_{1-10}$ alkoxycarbonyl, C$_{1-10}$ alkylcarbonyl and phenyl, said phenyl being optionally substituted with one or more substituents selected from the group consisting of halogen, hydroxy, nitro, cyano, amino, C$_{1-3}$ alkyl, C$_{1-3}$ haloalkyl, C$_{1-3}$ alkoxy and C$_{1-3}$ haloalkoxy;

each R$^{11}$ independently is R$^{10}$, —CO$_2$R$^{10}$, —SO$_2$R$^{10}$ or —C(O)R$^{10}$, or —N(R$^{11}$)$_2$ taken together is a non-aromatic heterocyclic group optionally substituted with one or more substituents selected from the group consisting of =O, =S, halogen, nitro, cyano, hydroxy, C$_{1-6}$ alkyl, C$_{1-6}$ haloalkyl, C$_{1-6}$ hydroxyalkyl, amino, C$_{1-6}$ alkylamino, C$_{1-6}$ dialkylamino, C$_{1-6}$ aminoalkyl, (C$_{1-6}$ alkylamino)C$_{1-6}$ alkyl, (C$_{1-6}$ dialkylamino)C$_{1-6}$ alkyl, C$_{1-6}$ alkoxy, C$_{1-6}$ haloalkoxy, C$_{1-6}$ alkylcarbonyloxy, C$_{1-6}$ alkoxycarbonyl and C$_{1-6}$ alkylcarbonyl; and each R$^{12}$ is independently is R$^{10}$ provided that R$^{12}$ is not hydrogen;

each R$^{21}$ independently is hydrogen, C$_{1-6}$ alkyl, phenyl or 5-6 membered heteroaryl, wherein each of the phenyl and heteroaryl groups represented by R$^{21}$ is independently and optionally substituted with one or more substituents selected from the group consisting of halogen, hydroxy, nitro, cyano, amino, C$_{1-3}$ alkyl, C$_{1-3}$ haloalkyl, C$_{1-3}$ alkoxy and C$_{1-3}$ haloalkoxy, and wherein the alkyl group represented by R$^{21}$ is optionally substituted with one or more substituents selected from the group consisting of halogen, hydroxy, nitro, cyano, amino, C$_{1-3}$ alkyl, C$_{1-3}$ haloalkyl, C$_{1-3}$ alkoxy and C$_{1-3}$ haloalkoxy; or N(R$^{21}$)$_2$ forms a non-aromatic heterocyclic group optionally substituted with one or more substituents selected from the group consisting of halogen, hydroxy, nitro, cyano, =O, C$_{1-3}$ alky, C$_{1-3}$ haloalkyl, C$_{1-3}$ alkoxy, C$_{1-3}$ haloalkoxy and amino; and each R$^{22}$ independently C$_{1-6}$ alkyl, phenyl or 5-6 membered heteroaryl, wherein each of the phenyl and heteroaryl groups represented by R$^{22}$ is independently and optionally substituted with one or more substituents selected from the group consisting of halogen, hydroxy, nitro, cyano, amino, C$_{1-3}$ alkyl, C$_{1-3}$ haloalkyl, C$_{1-3}$ alkoxy and C$_{1-3}$ haloalkoxy, and wherein the alkyl group represented by R$^{22}$ is optionally substituted with one or more substituents selected from the group consisting of halogen, hydroxy, nitro, cyano, amino, C$_{1-3}$ alkyl, C$_{1-3}$ haloalkyl, C$_{1-3}$ alkoxy and C$_{1-3}$ haloalkoxy;

each R independently is hydrogen, C$_{1-10}$ aliphatic, phenyl or 5-6 membered heteroaryl, wherein the aliphatic group represented by R is optionally substituted with one or more substituents selected from the group consisting of halogen, hydroxy, nitro, cyano, amino, phenyl, 5-6 membered heteroaryl, C$_{1-6}$ alkoxy, C$_{1-6}$ haloalkoxy, and wherein each of the phenyl and heteroaryl groups represented by R, and the phenyl and heteroaryl substituents for the aliphatic group represented by R independently are optionally and independently substituted with one or more substituents selected from the group consisting of halogen, hydroxy, nitro, cyano, amino, C$_{1-6}$ alkyl, C$_{1-6}$ haloalkyl, C$_{1-6}$ alkoxy, C$_{1-6}$ haloalkoxy, or N(R)$_2$ forms a non-aromatic heterocyclic group optionally substituted with one or more substituents selected from the group consisting of =O, halogen, nitro, cyano, hydroxy, C$_{1-6}$ alkyl, C$_{1-6}$ haloalkyl, C$_{1-6}$ hydroxyalkyl, amino, C$_{1-6}$ alkylamino, C$_{1-6}$ dialkylamino, C$_{1-6}$ aminoalkyl, (C$_{1-6}$ alkylamino)C$_{1-6}$ alkyl, (C$_{1-6}$ dialkylamino)C$_{1-6}$ alkyl, (phenyl) C$_{1-6}$ alkyl, (5-6 membered heteroaryl)C$_{1-6}$ alkyl, C$_{1-6}$ alkoxy, C$_{1-6}$ haloalkoxy, C$_1$-6 alkylcarbonyloxy, C$_{1-6}$ alkoxycarbonyl, C$_{1-6}$ alkylcarbonyl, phenyl and 5-6 membered heteroaryl; and each R' independently is C$_{1-10}$ aliphatic, phenyl or 5-12 membered heteroaryl, wherein the aliphatic group represented by R$^1$ is optionally substituted with one or more substituents selected from the group consisting of halogen, hydroxy, nitro, cyano, amino, phenyl, 5-12 membered heteroaryl, C$_1$-C$_6$ alkoxy, C$_1$-C$_6$ haloalkoxy, C$_{1-6}$ alkylamino, C$_{1-6}$ dialkylamino, —C(O)(C$_1$-C$_6$ alkyl), —C(O)(C$_1$-C$_6$ haloalkyl), —C(O)(phenyl), —C(O)(non-aromatic heterocyclic group), —C(O)O(C$_1$-C$_6$ alkyl), —C(O)O(C$_1$-C$_6$ haloalkyl), —C(O)O(phenyl), —OC(O)(C$_1$-C$_6$ alkyl), —OC (O)(C$_1$-C$_6$ haloalkyl), —OC(O)(phenyl), —S(O)$_2$(C$_1$-C$_6$ alkyl), —S(O)$_2$(C$_1$-C$_6$ haloalkyl) and —S(O)$_2$(phenyl), and wherein each of the phenyl and heteroaryl groups represented by R', and the phenyl and heteroaryl groups in the substituents for the aliphatic group represented by R' independently are optionally substituted with one or more substituents selected from the group consisting of halogen, —OH, —SH, nitro, cyano, amino, $C_{1-6}$ alkylamino, $C_{1-6}$ dialkylamino, $C_1$-$C_6$ alkyl, $C_1$-$C_6$ haloalkyl, —O($C_{1-6}$ alkyl), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{0-6}$ alkyl, (5-6 membered heteroaryl)$C_{0-6}$ alkyl, (non-aromatic heterocyclic group)$C_{0-6}$ alkyl (optionally substituted with $C_{1-6}$ alkyl or $C_{1-6}$ acyl), —C(O)($C_1$-$C_6$ alkyl), —C(O)($C_1$-$C_6$ haloalkyl), —C(O)(phenyl), —C(O)(non-aromatic heterocyclic group), —C(O)O($C_1$-$C_6$ alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_{1-6}$ haloalkyl), and —S(O)$_2$(phenyl);

each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, ($C_{1-10}$ aminoalkyl), ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;

each p is 1, 2 or 3; and each q is 2, 3, 4 or 5.

Values and alternative values for the variables in Structural Formula (I) or (I') are provided in the following paragraphs:

Ring A and Ring B are optionally and independently substituted at any one or more substitutable ring carbon atoms, including the position represented by "Y" when "Y" is CH. Substituents for Ring A are represented by $R^a$ and substituents for Ring B are represented by $R^b$. Typically, Ring A has "n" substituents; whereas Ring B typically has "m" substituents. Definitions for $R^a$, $R^b$, "m" and "n" are provided below.

Ring C is a 5-membered heteroaromatic ring wherein one of $X_1$-$X_3$ is N, one of $X_1$-$X_3$ is $NR^5$, and one of $X_1$-$X_3$ is N or $CR^6$. Alternatively, $X_3$ is $CR^6$, $X_2$ is N and $X_1$ is $NR^5$. In another alternative, $X_3$ is $CR^6$, $X_2$ is N and $X_1$ is NH. In another alternative, $X_3$ is $NR^5$, $X_2$ is N and $X_1$ is $CR^6$. In another alternative, $X_3$ is NH, $X_2$ is N and $X_1$ is $CR^6$.

Y is independently CH or N. Alternatively, Y is CH.

Each $R^a$ and each $R^b$ are each independently halogen, —C(O)OR$^1$, —C(O)R$^1$, —C(S)R$^1$, —OC(O)R$^1$—, —C(O)NR$^1$R$^2$, —C(S)NR$^1$R$^2$, —OC(O)NR$^1$R$^2$, —S(O)R$^1$, —S(O)$_2$R$^1$, —SO$_3$R$^1$, —SO$_2$NR$^1$R$^2$, —OR$^1$, —SR$^1$, —NR$^1$R$^2$, —NR$^2$C(O)R$^1$, —NR$^2$S(O)R$^1$, —NR$^2$C(O)OR$^1$, NR$^2$C(O)ONR$^1$R$^2$, —N(R$^2$)C(O)NR$^1$R$^2$, —NR$^2$SO$_2$NR$^1$R$^2$, —NR$^2$SO$_2$R$^1$; —NO$_2$, —CN, —NCS; or two ortho $R^a$ groups taken together form —O—[CH$_2$]$_p$—O—, —S—[CH$_2$]$_p$—S— or —[CH$_2$]$_q$—; or a $C_{1-10}$ aliphatic group optionally substituted with one or more substituents selected from the group consisting halogen, nitro, cyano, —N(R$^{21}$)$_2$, —C(O)N(R$^{21}$)$_2$, —C(O)N(R$^{21}$)$_2$, —NR$^{21}$C(O)R$^{21}$, —SO$_2$R$^{22}$, —SO$_2$N(R$^{21}$)$_2$, NR$^{21}$SO$_2$R$^{22}$, —NR$^{21}$C(O)OR$^{21}$, —OC(O)N(R$^{21}$)$_2$, —NR$^{21}$C(O)N(R$^{21}$)$_2$, —NRC(O)ON(R)$_2$, —NR$^{21}$SO$_2$N(R$^{21}$)$_2$, —OR$^{21}$, —SR$^{21}$, $C_{1-10}$ haloalkoxy, —C(O)R$^{21}$, —C(O)OR$^{21}$ and —OC(O)R$^{21}$; or ($C_{0-10}$ alkylene)-Ar$^1$, ($C_{2-10}$ alkenylene)-Ar$^1$. Alternatively, each $R^a$ and each $R^b$ is independently halogen, cyano, —NR$^1$R$^2$, —NR$^2$C(O)R$^1$, —C(O)OR$^1$, —OC(O)R$^1$, —C(O)NR$^1$R$^2$, —NR$^2$C(O)OR$^1$, —N(R$^2$)C(O)NR$^1$R$^2$, —OR$^1$, —SO$_2$NR$^1$R$^2$, —NR$^2$SO$_2$R$^1$, $C_{1-6}$ alkyl, phenyl or 5-12 membered heteroaryl, wherein the $C_{1-6}$ alkyl represented by $R_a$ and $R_b$ is optionally and independently substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl; and the phenyl or the 5-12 membered heteroaryl represented by $R_a$ and $R_b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl. In another alternative, each $R^a$ is halogen, cyano, —NR$^1$R$^2$, —NR$^2$C(O)R$^1$, —C(O)OR$^1$, —OC(O)R$^1$, —N(R$^2$)C(O)NR$^1$R$^2$, —OR$^1$, $C_{1-6}$ alkyl, wherein the $C_{1-6}$ alkyl is optionally substituted with one or more substituents selected from the group consisting of halogen, —OH, —SH, —O($C_{1-6}$ alkyl), —S($C_{1-6}$ alkyl) and $C_{1-6}$ haloalkoxy. In another alternative, $R^a$ is halogen, —NH$_2$, ($C_{1-6}$ alkyl)amine or $C_{1-6}$ alkoxy. In another alternative, $R^b$ is —F, Cl or methyl.

Each $R^1$ independently is: i) hydrogen; ii) a $C_{6-14}$ aryl group or a 5-14 membered heteroaryl group, each optionally and independently substituted with one or more substituents selected from the group consisting of halogen, —NO$_2$, —CN, —NCS, $C_1$-$C_{10}$ aliphatic, ($C_{1-10}$ alkylene)-Ar$^{10}$, ($C_{2-10}$ alkenylene)-Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$C(O)R$^{10}$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$; or iii) a $C_{1-10}$ aliphatic group optionally substituted with one or more substituents selected from the group consisting of halogen, —NO$_2$, —CN, —NCS, Ar$^{10}$, —C(O)OR$^{10}$, —C(O)R$^{10}$, —C(S)R$^{10}$, —OC(O)R$^{10}$, —C(O)N(R$^{11}$)$_2$, —C(S)N(R$^{11}$)$_2$, —OC(O)N(R$^{11}$)$_2$, —S(O)R$^{12}$, —S(O)$_2$R$^{12}$, —SO$_3$R$^{12}$, —SO$_2$N(R$^{11}$)$_2$, —OR$^{10}$, —SR$^{10}$, —N(R$^{11}$)$_2$, —NR$^{11}$S(O)R$^{12}$, —NR$^{11}$C(O)OR$^{12}$, —N(R$^{11}$)C(O)N(R$^{11}$)$_2$, —NR$^{11}$SO$_2$N(R$^{11}$)$_2$ and —NR$^{11}$SO$_2$R$^{12}$, provided that $R^1$ is other than hydrogen when $R^a$ or $R^b$ is —S(O)R$^1$, —S(O)$_2$R$^1$, —SO$_3$R$^1$, —NR$^2$S(O)R$^1$ or —NR$^2$SO$_2$R$^1$. Alternatively, each $R^1$ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$ haloalkoxy.

Each $R^2$ independently is —H or $C_1$-$C_6$ alkyl, or, taken together with $NR^1$, forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl.

$R^3$ is —H, halogen, $C_{1-6}$ alkyl or $C_{1-6}$ haloalkyl. Alternatively, $R^3$ is —H.

$R^4$ is —H, $C_{1-6}$, phenyl, —C(O)($C_{1-6}$ alkyl), —C(O)(phenyl), —C(O)O($C_{1-6}$ alkyl), —C(O)O(phenyl), —S(O)$_2$($C_{1-6}$ alkyl) or —S(O)$_2$(phenyl), wherein each alkyl in the groups represented by $R^4$ independently is optionally substituted with one or more substituents selected from the group consisting of halogen, hydroxy, nitro, cyano, amino, phenyl, 5-6 membered heteroaryl, $C_{1-6}$ alkoxy and $C_{1-6}$ haloalkoxy, and wherein each phenyl in the groups represented by $R^4$ independently is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy. Alternatively, $R^4$ is —H, $C_{1-6}$ alkyl, phenyl, —C(O)($C_{1-6}$ alkyl), —C(O)(phenyl), —C(O)O($C_{1-6}$ alkyl), —C(O)O(phenyl), —S(O)$_2$($C_{1-6}$ alkyl) or —S(O)$_2$(phenyl), wherein each phenyl in the group represented by $R^4$ is optionally substituted with one or more substituents independently selected from the group consisting of halogen, $C_{1-6}$ alkyl, —O($C_{1-6}$ alkyl), $C_{1-6}$ haloalkyl, $C_{1-6}$ haloalkoxy, cyano and nitro. In another alternative, $R^4$ is —H.

$R^5$ is —H, $C_{1-6}$, phenyl, —C(O)($C_{1-6}$ alkyl), —C(O)(phenyl), —C(O)O($C_{1-6}$ alkyl), —C(O)O(phenyl), —S(O)$_2$($C_{1-6}$ alkyl) or —S(O)$_2$(phenyl), wherein each alkyl in the groups represented by $R^5$ independently is optionally substituted with one or more substituents selected from the group consisting of halogen, hydroxy, nitro, cyano, amino, phenyl, 5-6 membered heteroaryl, $C_{1-6}$ alkoxy and $C_{1-6}$ haloalkoxy, and wherein each phenyl in the groups represented by $R^5$ independently is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy. Alternatively, $R^5$ is —H, $C_{1-6}$ alkyl, phenyl, —C(O)($C_{1-6}$ alkyl), —C(O)(phenyl), —C(O)O($C_{1-6}$ alkyl), —C(O)O(phenyl), —S(O)$_2$($C_{1-6}$ alkyl) or —S(O)$_2$(phenyl), wherein each phenyl in the group represented by $R^5$ is optionally substituted with one or more substituents independently selected from the group consisting of halogen, $C_{1-6}$ alkyl, —O($C_{1-6}$ alkyl), $C_{1-6}$ haloalkyl, $C_{1-6}$ haloalkoxy, cyano and nitro. In another alternative, $R^5$ is —H.

$R^6$ is hydrogen, halogen, nitro, cyano, W, —OR, —SR, —N(R)$_2$, —C(O)R, —C(O)OR, —OC(O)R, —C(O)N(R)$_2$, —OC(O)N(R)$_2$, —NRC(O)R, —NRC(O)OR, —SOR$^1$, —SO$_2$R$^1$, —SO$_3$R$^1$, —SO$_2$N(R)$_2$, —NRS(O)R$^1$, —NRSO$_2$R$^1$, —NRC(O)N(R)$_2$, —NRC(O)ON(R)$_2$, or —NRSO$_2$N(R)$_2$. Alternatively, $R^6$ is optionally substituted phenyl, optionally substituted 5-12 membered heteroaryl, —CH$_2$— (optionally substituted phenyl), —CH$_2$— (optionally substituted 5-12 membered heteroaryl), —CH$_2$—CH$_2$— (optionally substituted phenyl), —CH$_2$—CH$_2$— (optionally substituted 5-12 membered heteroaryl), —CH=CH-(optionally substituted phenyl), —CH=CH-(optionally substituted 5-12 membered heteroaryl), —C≡C-(optionally substituted phenyl) or —C≡C-(optionally substituted 5-12 membered heteroaryl). Exemplary 5-12 membered heteroaryls in the group represented by $R^6$ include pyridyl, thiazolyl, pyrazinyl, thiophenyl, indolyl, quinolinyl, pyrrolyl, pyrazolyl, and pyrimidinyl, each of which is optionally substituted. In another alternative, exemplary 5-12 membered heteroaryls in the group represented by $R^6$ include optionally substituted pyridinyl, pyrimidinyl or pyrazinyl. Exemplary substituents for the phenyl or 5-12 membered heteroaryl in the group represented by $R^6$ include halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl, $C_{1-6}$ alkylcarbonyl, —(CH$_2$)$_{0-3}$—N-piperidinyl, —(CH$_2$)$_{0-3}$—N-morpholinyl, (CH$_2$)$_{0-3}$—N-pyrrolidinyl and —(CH$_2$)$_{0-3}$—N—(CH$_2$)$_{0-3}$-piperazinyl, wherein the N-piperazinyl is optionally substituted with $C_{1-6}$ alkyl or $C_{1-6}$ acyl. Alternatively, exemplary substituents for the phenyl or 5-12 membered heteroaryl in the group represented by $R^6$ include halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N-piperazinyl, wherein the N-piperazinyl is optionally substituted with $C_{1-6}$ alkyl or $C_{1-6}$ acyl. When substituted, the phenyl and 5-12 membered heteroaryl group represented by $R^6$ can have one or more substituents.

Each $R^{10}$ independently is: i) hydrogen; ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy.

Each $R^{11}$ independently is $R^{10}$, —CO$_2$R$^{10}$, —SO$_2$R$^{10}$ or —C(O)R$^{10}$, or —N(R$^{11}$)$_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl.

Each $R^{12}$ is independently is $R^{10}$ provided that $R^{12}$ is not hydrogen;

Each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy; or N(R$^{21}$)$_2$ forms a non-aromatic heterocyclic group optionally substituted with one or more substituents selected from the group consisting of halogen, hydroxy, nitro, cyano, =O, $C_{1-3}$ alky, $C_{1-3}$ haloalkyl, $C_{1-3}$ alkoxy, $C_{1-3}$ haloalkoxy and amino; and Each $R^{22}$ independently $C_{1-6}$ alkyl, phenyl or 5-6 membered heteroaryl, wherein each of the phenyl and heteroaryl groups represented by $R^{22}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{22}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

Each R independently is hydrogen, $C_{1-10}$ aliphatic, phenyl or 5-6 membered heteroaryl. The aliphatic group represented by R is optionally substituted with one or more substituents selected from the group consisting of halogen, hydroxy, nitro, cyano, amino, phenyl, 5-6 membered heteroaryl, $C_{1-6}$ alkoxy, $C_{1-6}$ haloalkoxy, and wherein each of the phenyl and heteroaryl groups represented by R, and the phenyl and heteroaryl substituents for the aliphatic group represented by R independently are optionally and independently substituted with one or more substituents selected from the group consisting of halogen, hydroxy, nitro, cyano, amino, $C_{1-6}$ alkyl, $C_{1-6}$ haloalkyl, $C_{1-6}$ alkoxy, $C_{1-6}$ haloalkoxy, or $N(R)_2$ forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_1$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl.

Each R' independently is $C_{1-10}$ aliphatic, phenyl or 5-12 membered heteroaryl. The aliphatic group represented by $R^1$ is optionally substituted with one or more substituents selected from the group consisting of halogen, hydroxy, nitro, cyano, amino, phenyl, 5-12 membered heteroaryl, $C_1$-$C_6$ alkoxy, $C_1$-$C_6$ haloalkoxy, $C_{1-6}$ alkylamino, $C_{1-6}$ dialkylamino, —C(O)($C_1$-$C_6$ alkyl), —C(O)($C_1$-$C_6$ haloalkyl), —C(O)(phenyl), —C(O)(non-aromatic heterocyclic group), —C(O)O($C_1$-$C_6$ alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl); and each of the phenyl and heteroaryl groups represented by W, and the phenyl and heteroaryl groups in the substituents for the aliphatic group represented by $R^1$ independently are optionally substituted with one or more substituents selected from the group consisting of halogen, —OH, —SH, nitro, cyano, amino, $C_{1-6}$ alkylamino, $C_{1-6}$ dialkylamino, $C_1$-$C_6$ alkyl, $C_1$-$C_6$ haloalkyl, —O($C_{1-6}$ alkyl), —S($C_{1-6}$ alkyl), —O($C_{1-6}$ haloalkyl), ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{0-6}$ alkyl, (5-6 membered heteroaryl)$C_{0-6}$ alkyl, (non-aromatic heterocyclic group)$C_{0-6}$ alkyl (optionally substituted with $C_{1-6}$ alkyl or $C_{1-6}$ acyl), —C(O)($C_1$-$C_6$ alkyl), —C(O) ($C_1$-$C_6$ haloalkyl), —C(O)(phenyl), —C(O)(non-aromatic heterocyclic group), —C(O)O($C_1$-$C_6$ alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl), and —S(O)$_2$(phenyl). Alternatively, suitable substituents for the each of the aliphatic, phenyl and heteroaryl groups represented by $R^1$, and the phenyl and heteroaryl groups in the substituents for the aliphatic group represented by $R^1$ independently are as described for the phenyl and 5-12 membered heteroaryl groups represented by $R^6$.

$Ar^1$ is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, —$N(R^{21})_2$, —C(O)N $(R^{21})_2$, —C(O)N($R^{21}$)$_2$, —$NR^{21}$C(O)$R^{21}$, —SO$_2R^{22}$, —SO$_2$N($R^{21}$)$_2$, —$NR^{21}$SO$_2R^{22}$, —$NR^{21}$C(O)N($R^{21}$)$_2$, —NRC(O)ON(R)$_2$, —$NR^{21}$SO$_2$N($R^{21}$)$_2$, —$OR^{21}$, —$SR^{21}$, $C_{1-10}$ haloalkoxy, —C(O)$R^{21}$, —C(O)O$R^{21}$, —OC(O)$R^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy.

Each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, ($C_{1-10}$ aminoalkyl), ($C_{1-10}$ alkylamino)$C_{1-10}$ alkyl, ($C_{1-10}$ dialkylamino)$C_{1-10}$ alkyl, (phenyl) $C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl.

Each n is 0, 1, 2, 3 or 4. Alternatively, each n is 0, 1 or 2.

Each m is 0, 1, 2 or 3. Alternatively, each m is 0 or 1. In another alternative, m is 0.

Each p is 1, 2 or 3; and

Each q is 2, 3, 4 or 5.

In another embodiment, small molecule PLK4 antagonists include a compound represented by any one of following structural formulas (Ia)-(Id), (II)-(XIII), (IIa)-(XIIIa), (IIb)-(XIIIb), (IIc)-(XIIIc), (IId)-(XIIId), and (II')-(XIII') or a pharmaceutically acceptable salt thereof:

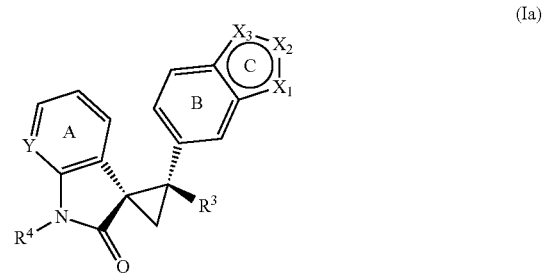

(Ia)

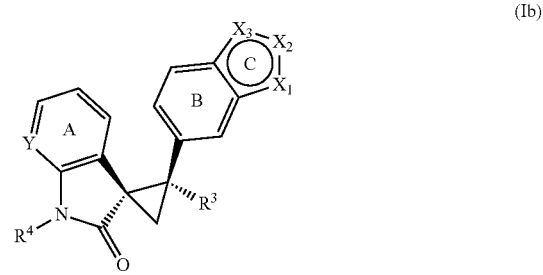

(Ib)

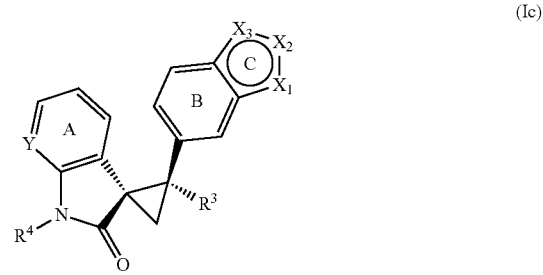

(Ic)

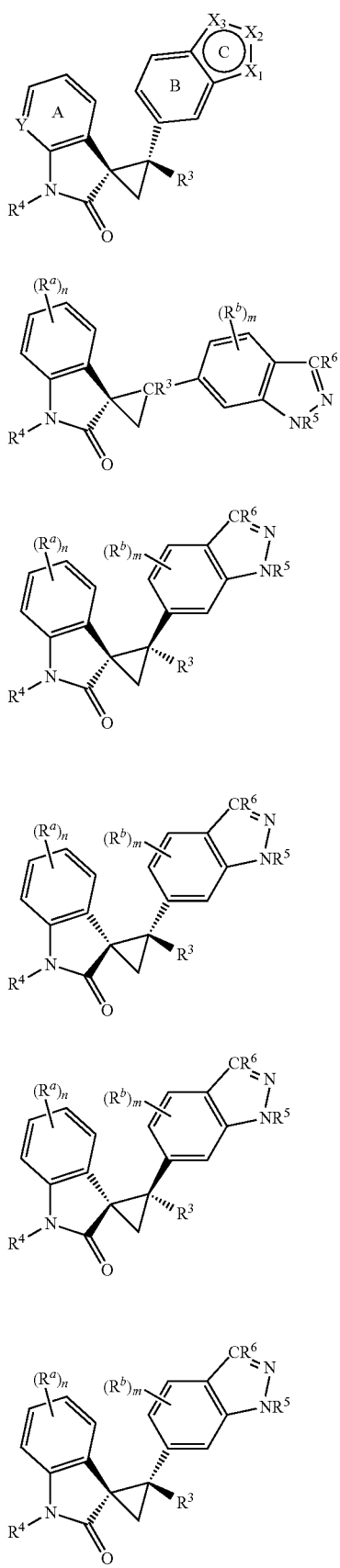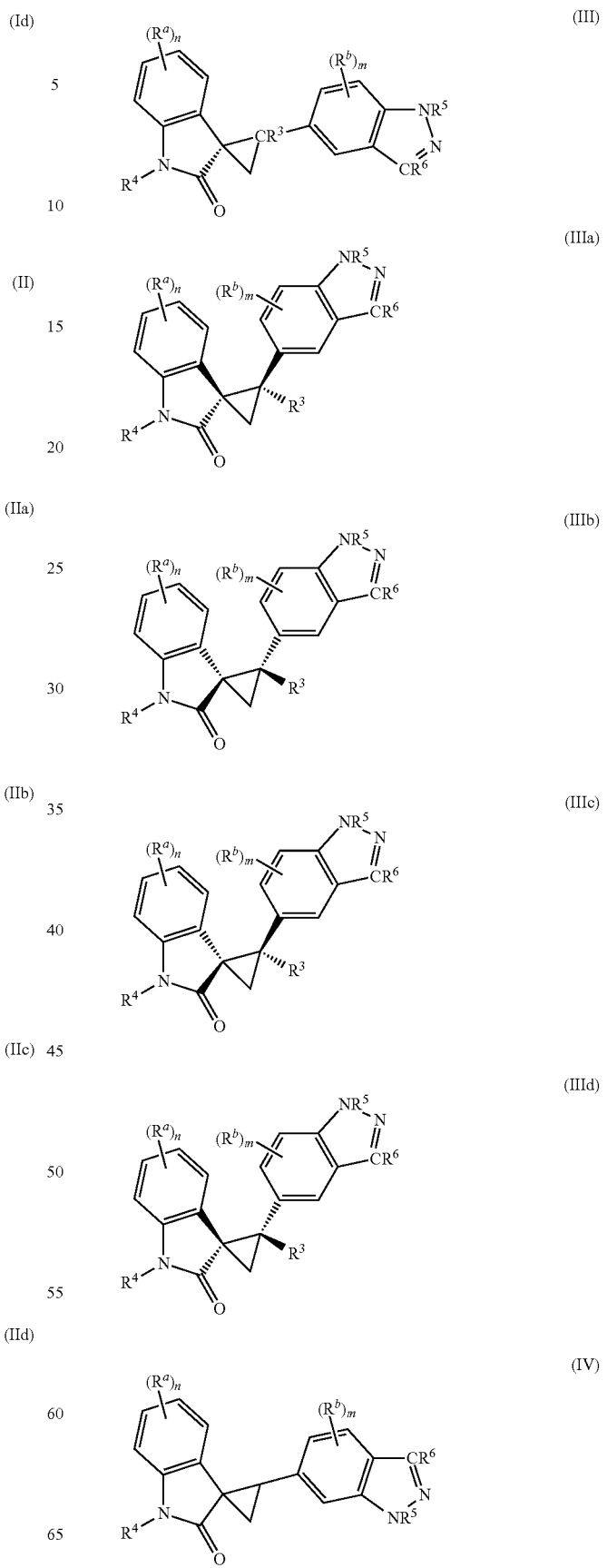

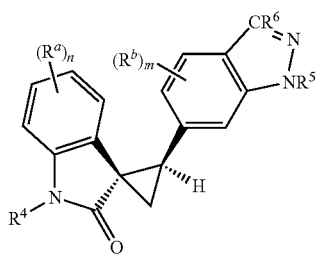 (IVa)
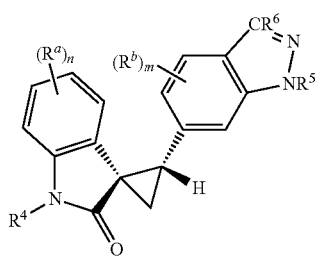 (IVb)
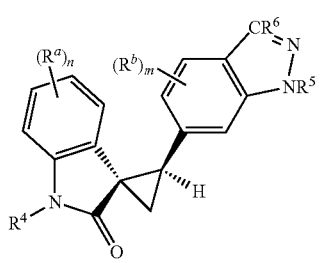 (IVc)
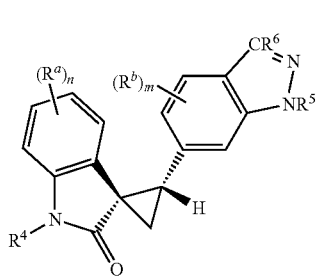 (IVd)
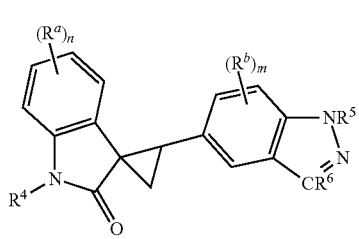 (V)
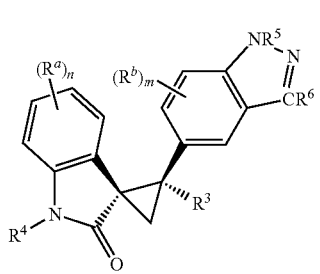 (Va)
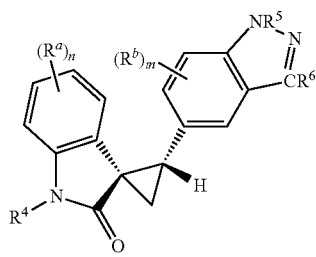 (Vb)
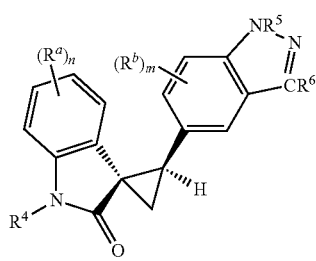 (Vc)
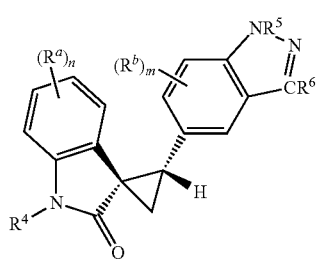 (Vd)
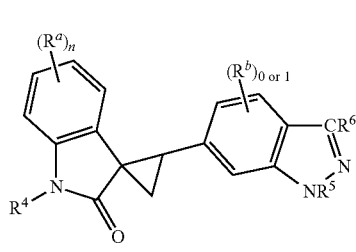 (VI)
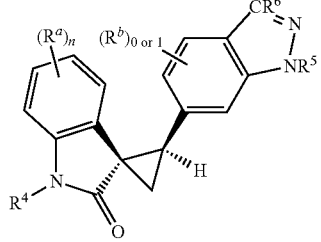 (VIa)
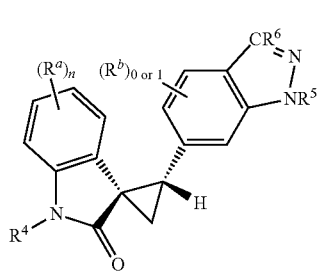 (VIb)

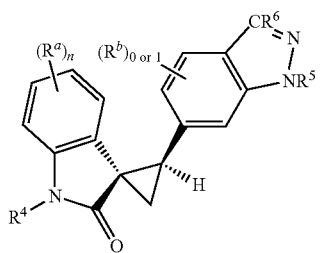 (VIc)
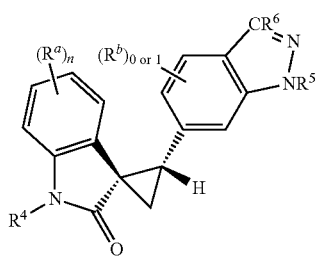 (VId)
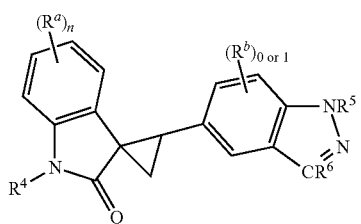 (VII)
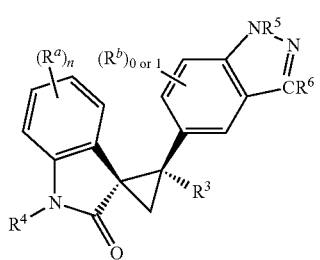 (VIIa)
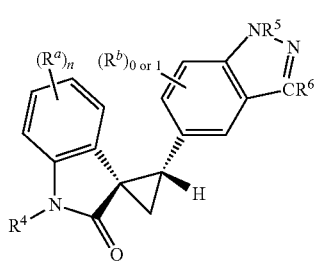 (VIIb)
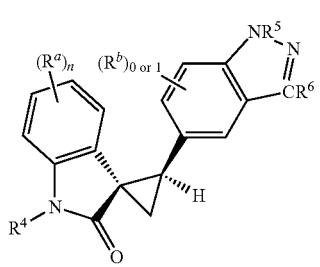 (VIIc)
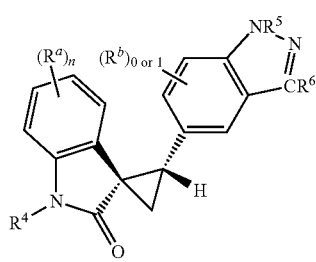 (VIId)
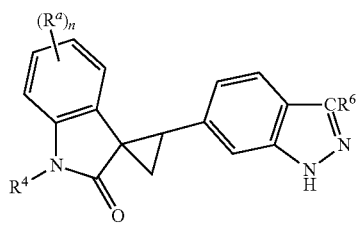 (VIII)
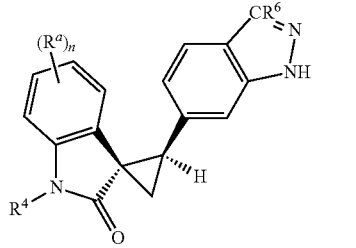 (VIIIa)
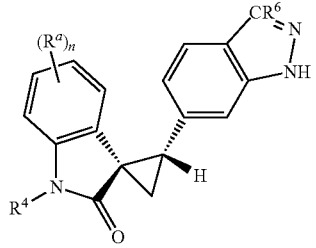 (VIIIb)
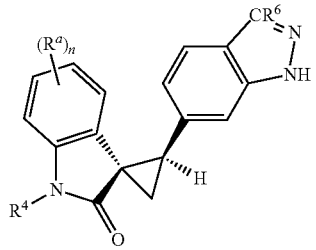 (VIIIc)
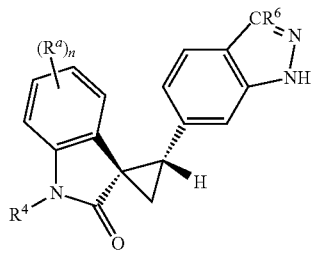 (VIIId)

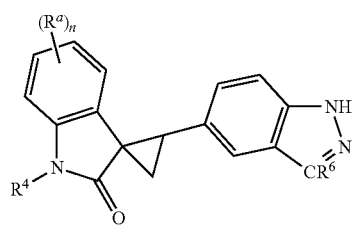
(IX)
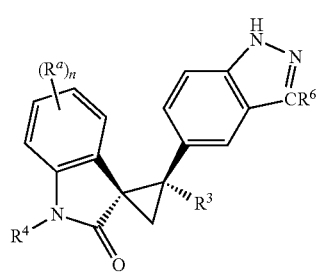
(IXa)
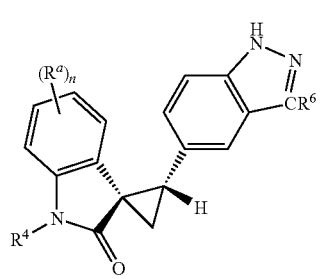
(IXb)
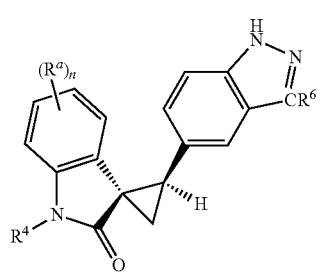
(IXc)
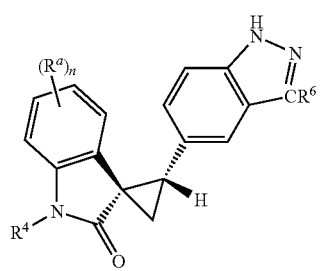
(IXd)
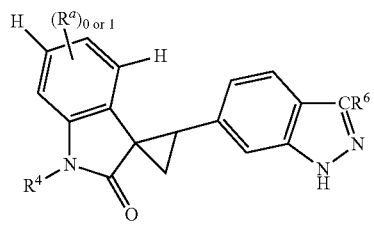
(X)
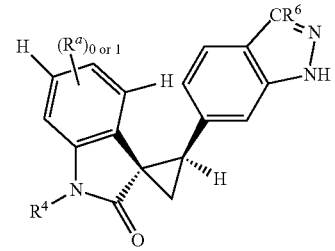
(Xa)
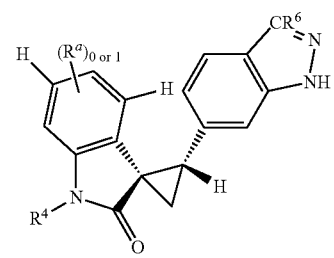
(Xb)
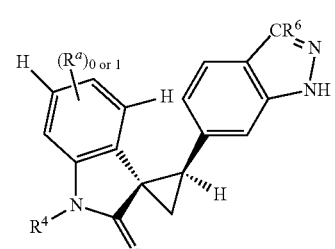
(Xc)
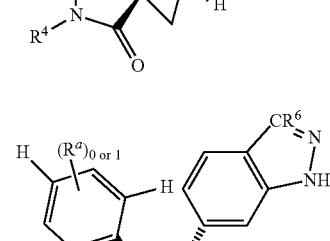
(Xd)
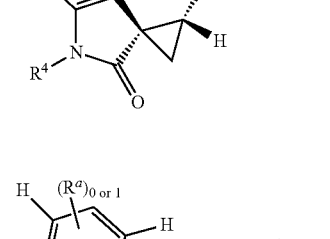
(XI)
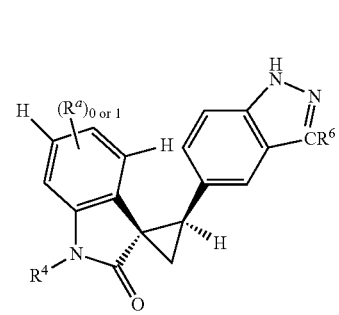
(XIa)

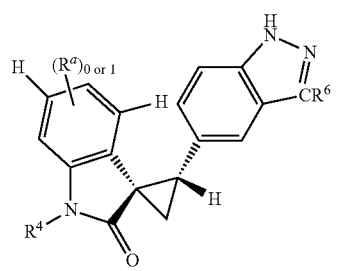
(XIb)
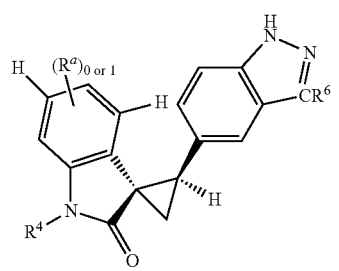
(XIc)
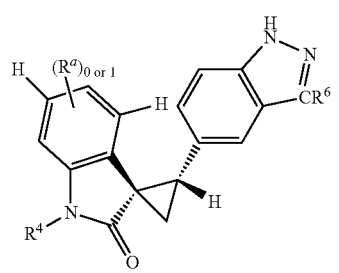
(XId)
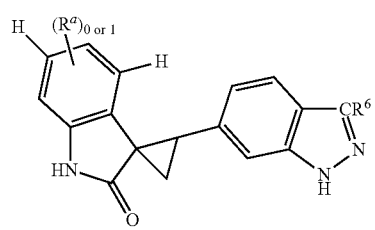
(XII)
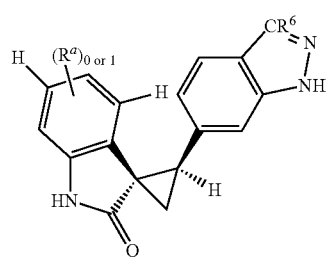
(XIIa)
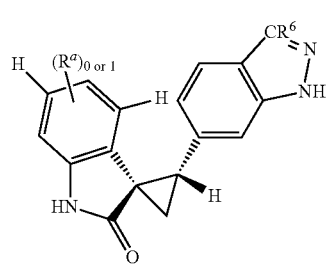
(XIIb)
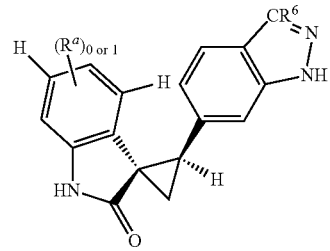
(XIIc)
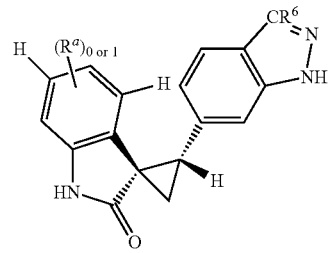
(XIId)
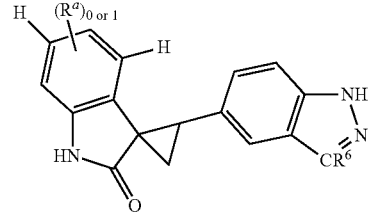
(XIII)
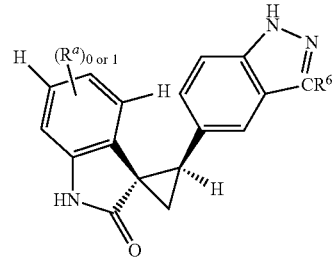
(XIIIa)
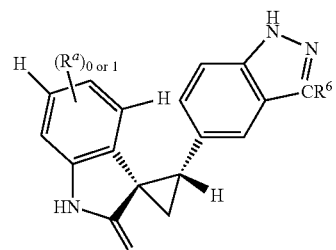
(XIIIb)
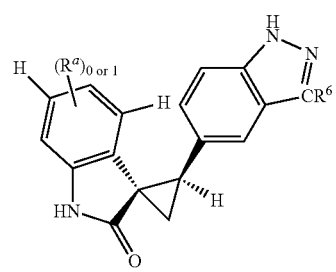
(XIIIc)

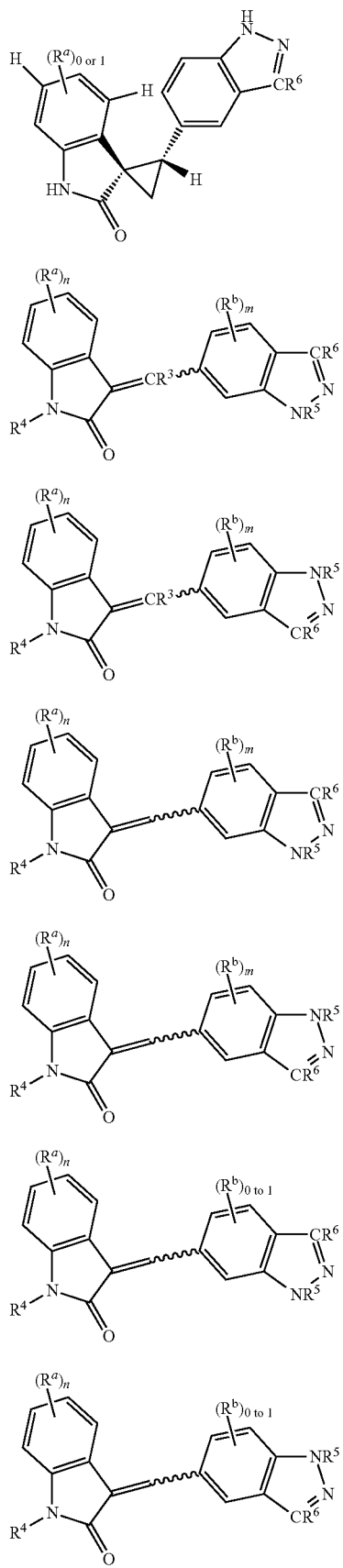
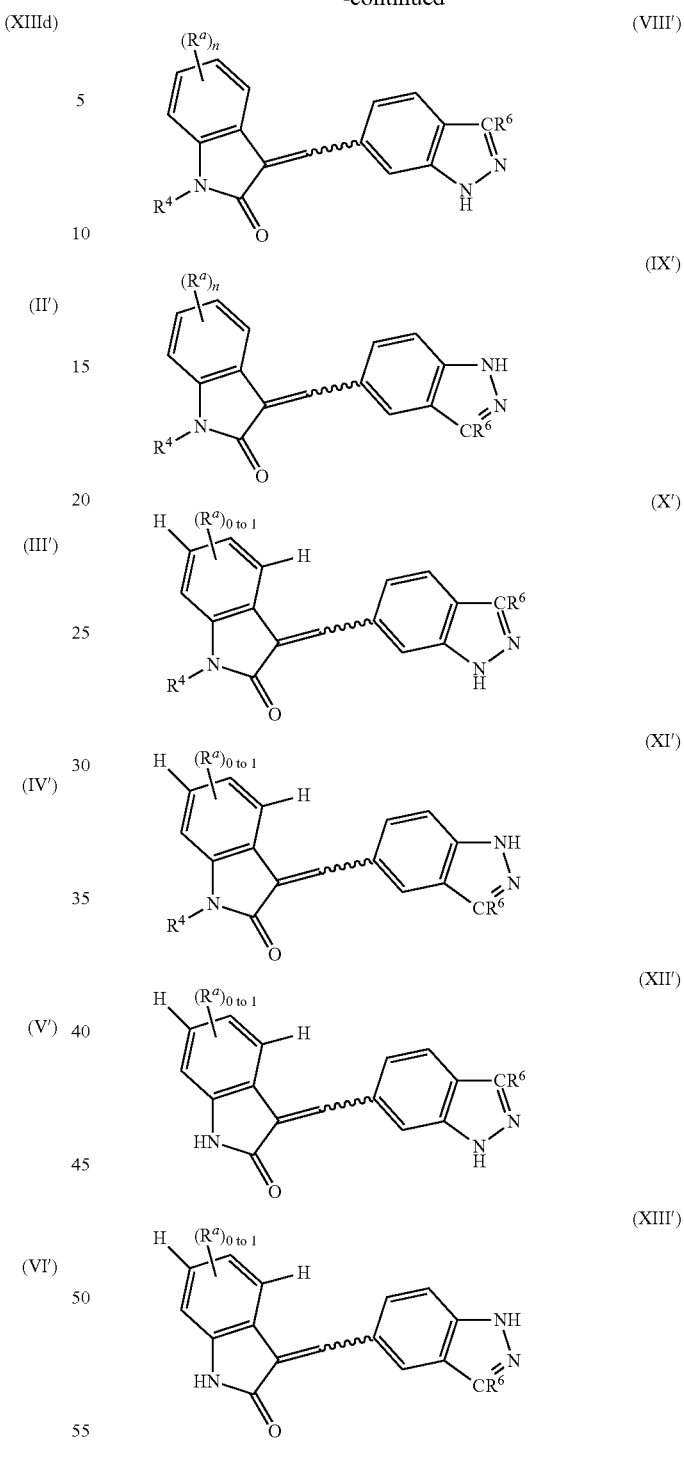

Values and alternative values for the variables in Structural Formulas (Ia)-(Id), (II)-(XIII), (IIa)-(XIIIa), (IIb)-(XIIIb), (IIc)-(XIIIc), (IId)-(XIIId), and (II')-(XIII') are as described for Structural Formulas (I) above.

In a second embodiment, small molecule PLK4 antagonists include compounds represented by any one of Structural Formulas (Ia)-(Id), (II)-(VII), (IIa)-(VIIa), (IIb)-(XIIIb), (IIc)-(VIII), (IId)-(VIId), and (II')-(VII') or a pharmaceutically acceptable salt thereof, wherein $R^5$ is —H, $C_1$-$C_6$ alkyl, phenyl, —C(O)($C_1$-$C_6$ alkyl), —C(O)(phenyl), —C(O)O ($C_1$-$C_6$ alkyl), —C(O)O(phenyl), —S(O)$_2$($C_1$-$C_6$ alkyl) or —S(O)$_2$(phenyl), wherein each phenyl in the group represented by $R^5$ is optionally substituted with one or more substituents independently selected from the group consisting of halogen, $C_{1-6}$ alkyl, —O($C_{1-6}$ alkyl), $C_{1-6}$ haloalkyl, $C_{1-6}$ haloalkoxy, cyano and nitro; and values and alternative values for the remainder of the variables are as described above for Structural Formulas (I).

In a third embodiment, small molecule PLK4 antagonists include compounds represented by any one of Structural Formulas (Ia)-(Id), (II)-(XI), (IIa)-(XIa), (IIb)-(XIb), (IIc)-(XIc), (IId)-(XId), and (II')—(XI') or a pharmaceutically acceptable salt thereof, wherein $R^4$ is —H, $C_1$-$C_6$ alkyl, phenyl, —C(O)($C_1$-$C_6$ alkyl), —C(O)(phenyl), —C(O)O($C_1$-$C_6$ alkyl), —C(O)O(phenyl), —S(O)$_2$($C_1$-$C_6$ alkyl) or —S(O)$_2$(phenyl), wherein each phenyl in the group represented by $R^4$ is optionally substituted with one or more substituents independently selected from the group consisting of halogen, $C_{1-6}$ alkyl, —O($C_{1-6}$ alkyl), $C_{1-6}$ haloalkyl, $C_{1-6}$ haloalkoxy, cyano and nitro; $R^5$, when present (as in Structural Formulas (Ia)-(Id), (II)-(VII), (IIa)-(VIIa), (IIb)-(VIIIb), (IIc)-(VIII), (IId)-(VIId) and (II')-(VII')), is selected from the same list of values as $R^4$, but is independently selected with respect to $R^4$; and values and alternative values for the remainder of the variables are as described above for Structural Formulas (I).

In a fourth embodiment, small molecule PLK4 antagonists include compounds represented by any one of Structural Formulas (Ia)-(Id), (II)-(XIII), (IIa)-(XIIIa), (IIb)-(VIIIb), (IIc)-(XIIIc), (IId)-(XIIId), and (II')-(XIII'), or a pharmaceutically acceptable salt thereof, wherein $R^4$, when present (as in Structural Formulas (Ia)-(Id), (II)-(XI), (IIa)-(XIa), (IIb)-(XIb), (IIc)-(XIc), (IId)-(XId), and (II')-(XI')), and $R^5$, when present (as in Structural Formulas (Ia)-(Id), (II)-(VII), (IIa)-(VIIa), (IIb)-(VIIIb), (IIc)-(VIII), (IId)-(VIId), and (II')-(VII')), are independently —H, $C_1$-$C_6$ alkyl, phenyl, —C(O)($C_1$-$C_6$ alkyl), —C(O)(phenyl), —C(O)O($C_1$-$C_6$ alkyl), —C(O)O(phenyl), —S(O)$_2$($C_1$-$C_6$ alkyl) or —S(O)$_2$(phenyl), wherein each phenyl in the group represented by $R^5$ is optionally substituted with one or more substituents independently selected from the group consisting of halogen, $C_{1-6}$ alkyl, —O($C_{1-6}$ alkyl), $C_{1-6}$ haloalkyl, $C_{1-6}$ haloalkoxy, cyano and nitro; $R^6$ is optionally substituted phenyl, optionally substituted 5-12 membered heteroaryl, —CH$_2$— (optionally substituted phenyl), —CH$_2$— (optionally substituted 5-12 membered heteroaryl), —CH$_2$—CH$_2$— (optionally substituted phenyl), —CH$_2$—CH$_2$— (optionally substituted 5-12 membered heteroaryl), —CH=CH-(optionally substituted phenyl), —CH=CH-(optionally substituted 5-12 membered heteroaryl), substituted phenyl) or —C≡C-(optionally substituted 5-12 membered heteroaryl); and values and alternative values for the remainder of the variables are as described above for Structural Formulas (I). Exemplary 5-12 membered heteroaryls in the group represented by $R^6$ include pyridyl, thiazolyl, pyrazinyl, thiophenyl, indolyl, quinolinyl, pyrrolyl, pyrazolyl, and pyrimidinyl, each of which is optionally substituted. An alternative group of exemplary 5-12 membered heteroaryls in the group represented by $R^6$ include optionally substituted pyridinyl, pyrimidinyl or pyrazinyl.

Exemplary substituents for the phenyl and 5-12 membered heteroaryl group represented by $R^6$ in the fourth embodiment include halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy) $C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl, $C_{1-6}$ alkylcarbonyl, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N—(CH$_2$)$_{0-3}$-piperazinyl, wherein the N-piperazinyl is optionally substituted with $C_{1-6}$ alkyl or $C_{1-6}$ acyl. An alternative list of exemplary substituents for the phenyl and 5-12 membered heteroaryl group represented by $R^6$ in the fourth embodiment include halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, amino, $C_{1-6}$ alkylamino, $C_{1-6}$ dialkylamino, —(CH$_2$)$_{0-3}$—N-piperidinyl, —(CH$_2$)$_{0-3}$—N-morpholinyl, —(CH$_2$)$_{0-3}$—N-pyrrolidinyl and —(CH$_2$)$_{0-3}$—N-piperazinyl, wherein the N-piperazinyl is optionally substituted with $C_{1-6}$ alkyl or $C_{1-6}$ acyl.

In a fifth embodiment, small molecule PLK4 antagonists include compounds represented by any one of (Ia)-(Id), (II)-(XIII), (IIa)-(XIIIa), (IIb)-(XIIIb), (IIc)-(XIIIc), (IId)-(XIIId) and (II')-(XIII'), wherein $R^a$ and $R^b$, when present (as in (Ia)-(Id), (II)-(VII), (IIa)-(VIIa), (IIb)-(VIIb), (IIc)-(VIIc), (IId)-(VIId) and (II')-(VII')) are independently halogen, cyano, —NR$^1$R$^2$, —NR$^2$C(O)R$^1$, —C(O)OR$^1$, —OC(O)R$^1$, —C(O)NR$^1$R$^2$, —NR$^2$C(O)OR$^1$, —N(R$^2$)C(O)NR$^1$R$^2$, —OR$^1$, —SO$_2$NR$^1$R$^2$, —NR$^2$SO$_2$R$^1$, $C_{1-6}$ alkyl, phenyl or 5-12 membered heteroaryl, wherein the $C_{1-6}$ alkyl represented by $R^a$ and $R_b$ is optionally and independently substituted with one or more substituents selected from the group consisting of halogen, nitro, cyano, —OH, —SH, —O($C_{1-6}$ alkyl), —S($C_{1-6}$ alkyl), $C_{1-6}$ haloalkoxy, amino, $C_{1-6}$ alkylamino, $C_{1-6}$ dialkylamino, $C_{1-6}$ alkylcarbonyloxy, $C_{1-6}$ alkoxycarbonyl and $C_{1-6}$ alkylcarbonyl; and the phenyl or the 5-12 membered heteroaryl represented by $R^a$ and $R_b$ is optionally substituted with one or more substituents selected from the group consisting of halogen, nitro, cyano, —OH, —SH, —O($C_{1-6}$ alkyl), —S($C_{1-6}$ alkyl), $C_{1-6}$ alkyl, $C_{1-6}$ haloalkyl, ($C_{1-6}$ haloalkoxy)$C_{1-6}$ alkyl, ($C_{1-6}$ alkoxy)$C_{1-6}$ alkyl, $C_{1-6}$ hydroxyalkyl, ($C_{1-6}$ aminoalkyl), ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, amino, $C_{1-6}$ alkylamino, $C_{1-6}$ dialkylamino, $C_{1-6}$ haloalkoxy, $C_{1-6}$ alkylcarbonyloxy, $C_{1-6}$ alkoxycarbonyl and $C_{1-6}$ alkylcarbonyl; each $R^1$ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), —S($C_{1-3}$ alkyl) and $C_{1-6}$ haloalkoxy; and the remainder of the variables are defined as in the first, second, third or fourth embodiment.

In a sixth embodiment, small molecule PLK4 antagonists include compounds represented by any one of (Ia)-(Id), (II)-(XIII), (IIa)-(XIIIa), (IIb)-(XIIIb), (IIc)-(XIIIc), (IId)-(XIIId) and (II')-(XIII'), wherein $R^a$ and $R^b$, when present (as in (Ia)-(Id), (II)-(VII), (IIa)-(VIIa), (IIb)-(VIIb), (IIc)-(VIIc), (IId)-(VIId), and (II')-(VII')), are independently halogen, cyano, —NR$^1$R$^2$, —NR$^2$C(O)R$^1$, —C(O)OR$^1$, —OC(O)R$^1$, —N(R$^2$)C(O)NR$^1$R$^2$, —OR$^1$ or $C_{1-6}$ alkyl, wherein the $C_{1-6}$ alkyl is optionally substituted with one or more substituents selected from the group consisting of halogen, —OH, —SH, —O($C_{1-6}$ alkyl), —S($C_{1-6}$ alkyl) and $C_{1-6}$ haloalkoxy; each $R^1$ is independently —H or $C_{1-6}$ alkyl, wherein the $C_{1-6}$ alkyl is optionally substituted with one or more substituents independently selected from the group consisting of halogen, —OH, —SH, —O($C_{1-3}$ alkyl), S($C_{1-3}$ alkyl) and $C_{1-6}$ haloalkoxy; and the remainder of the variables are defined as in the first, second, third or fourth embodiment.

In a seventh embodiment, small molecule PLK4 antagonists include compounds represented by any one of (Ia)-(Id), (II)-(XIII), (IIa)-(XIIIa), (IIb)-(XIIIb), (IIc)-(XIIIc), (IId)-(XIIId) and (IIa')-(XIIIa'), wherein $R^a$ and $R^b$, when present (as in (Ia)-(Id), (II)-(VII), (IIa)-(VIIa), (IIb)-(VIIb), (IIc)-(VIII), (IId)-(VIId) and (II')-(VII')), are independently halogen, —NH$_2$, (C$_{1-6}$ alkyl)amine or C$_{1-6}$ alkoxy; and the remainder of the variables are defined as in the first, second, third or fourth embodiment.

In a eighth embodiment, small molecule PLK4 antagonists used for treating a disease (e.g., a cancer, such as breast cancer) include the following small molecule compounds or pharmaceutically acceptable salts or solvates thereof:

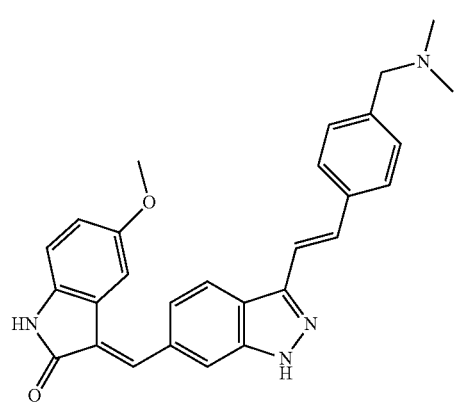

1

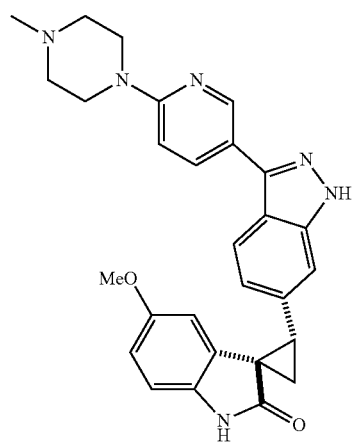

2

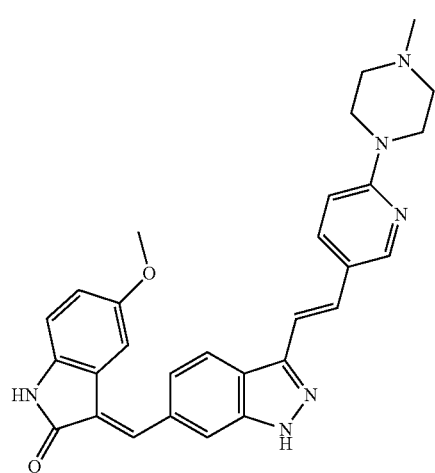

3

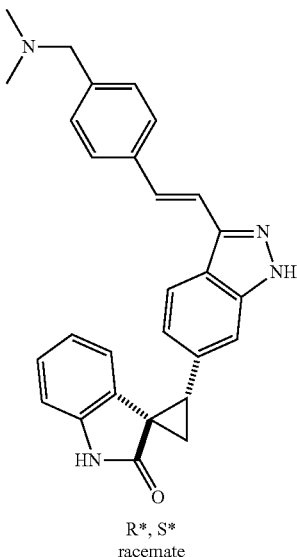

5

R*, S*
racemate

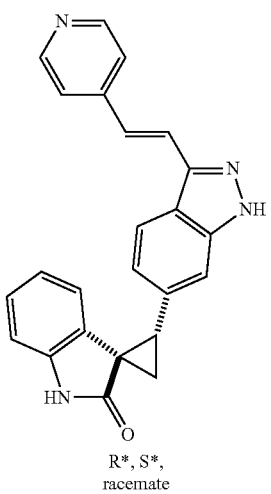

6

R*, S*,
racemate

Specific examples of small molecule PLK4 antagonists include those exemplified in the examples below, stereoisomers thereof, and pharmaceutically acceptable salts thereof. Additional specific examples of small molecule PLK4 antagonists include those exemplified in the examples in WO 09/079,767, published Jul. 2, 2009 and WO 10/115,279, published Oct. 14, 2010. The entire contents of these published applications are incorporated herein by this reference.

The recitation "the phenyl and the 5-12 membered heteroaryl in the group represented by R$^6$" refers to the phenyl and 5-12 membered heteroaryl in any value for the variable R$^6$ which consists of phenyl or a 5-12 membered heteroaryl or which comprises phenyl or a 5-12 membered heteroaryl. For example, when R$^6$ is defined to be "optionally substituted phenyl, optionally substituted 5-12 membered heteroaryl, —CH$_2$-(optionally substituted phenyl), —CH$_2$— (optionally substituted 5-12 membered heteroaryl), —CH$_2$—CH$_2$— (optionally substituted phenyl), —CH$_2$—CH$_2$— (optionally substituted 5-12 membered heteroaryl), —CH=CH-(optionally substituted phenyl), —CH=CH-(optionally substituted 5-12 membered heteroaryl), —C≡C-(optionally substituted phenyl) or —C≡C-(5-12 optionally substituted membered heteroaryl)", then the language "the phenyl and the 5-12 membered heteroaryl in the group represented by R⁶‴ refers to the phenyl and the 5-12 membered heteroaryl represented by R⁶ as well as to the phenyl moiety and the 5-12 membered heteroaryl moiety in the groups —CH₂— (optionally substituted phenyl), —CH₂—(optionally substituted 5-12 membered heteroaryl), —CH₂—CH₂— (optionally substituted phenyl), —CH₂—CH₂— (optionally substituted 5-12 membered heteroaryl), —CH═CH-(optionally substituted phenyl), —CH═CH-(optionally substituted 5-12 membered heteroaryl), —C≡C-(optionally substituted phenyl) or —C≡-C-(optionally substituted 5-12 membered heteroaryl).

In Structural Formulas described herein, when a hydrogen atom(s) is depicted at a particular position(s) of the aromatic ring(s) of the structural formula (s), no substitution is permitted at that (those) particular position(s).

Tautomeric forms exist when a compound is a mixture of two or more structurally distinct compounds that are in rapid equilibrium. Certain compounds of the present teachings exist as tautomeric forms. For example, the following compound represented by Structural Formula (I) include at least the following tautomeric forms:

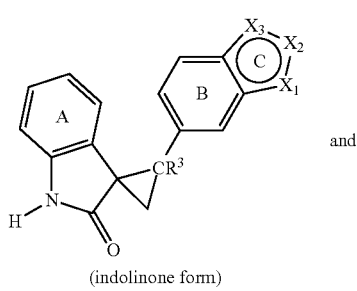

(indolinone form)

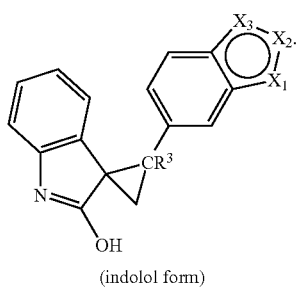

(indolol form)

Likewise, the compound represented by Structural Formula (I') include at least the following tautomeric forms:

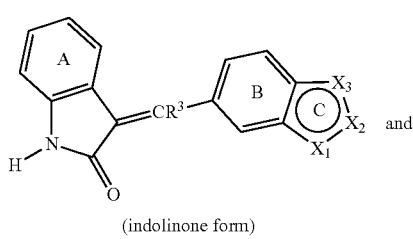

(indolinone form)

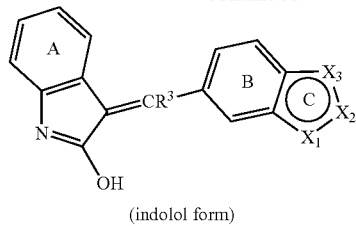

(indolol form)

It is to be understood that when one tautomeric form of a compound is depicted by name or structure, all tautomeric forms of the compound are included.

The PLK4 antagonists represented by Structural Formula (I) contain at least two chiral centers and a cyclopropane and, therefore, exist as stereoisomers, such as isomers about the cyclopropane (i.e., cis/trans isomers), enantiomers, and/or diastereomers. When compounds are depicted or named without indicating the stereochemistry, it is to be understood that both stereomerically pure forms (e.g., pure cis or pure trans, enantiomerically pure, or diastereomerically pure) and stereoisomeric mixtures are encompassed. For example, compounds represented by Structural Formulas (I) have "cis" and "trans" isomers shown below:

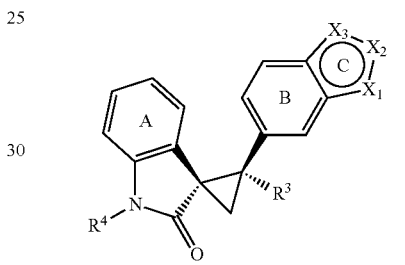

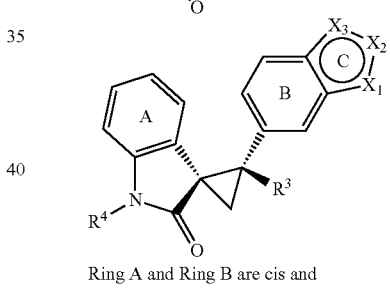

Ring A and Ring B are cis and

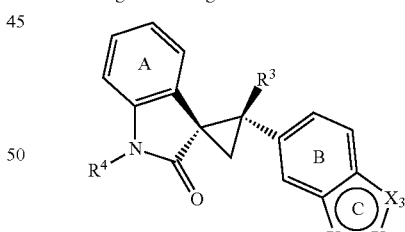

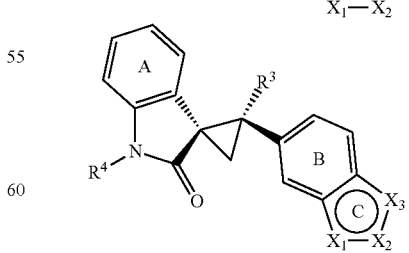

Ring A and Ring B are trans.

The language "Ring A and Ring B are cis" means Ring A and Ring B are both on the same side of the cyclopropane whereas the language "Ring A and Ring B are trans" means Ring A and Ring B are on different sides of the cyclopropane. Stereoisomers of the cis/trans variety are also referred to as geometric isomers. Accordingly, the compounds depicted by Structural Formula (I)-(XIII) include the pure cis geometric isomer, the pure trans geometric isomer, and mixtures thereof, including cis/trans mixtures enriched in the cis geometric isomer and cis/trans mixtures enriched in the trans geometric isomer. For example, Structural Formulas (Ia)-(XIIIa) and (Ib)-(XIIIb), depict a cis relationship between Ring A and B, whereas in, for example, Structural Formulas (Ic)-(XIIIc) and (Id)-(XIIId) the relationship between Ring A and B is trans. It is to be understood that both cis and trans forms of Structural Formulas (I)-(XIII) with respect to Rings A and B are encompassed within the present teachings.

The compounds represented by Structural Formulas (I')-(XIII') have E and Z geometric isomers. For example, the E and Z geometric isomers for compounds of Structural Formula (I') are shown below:

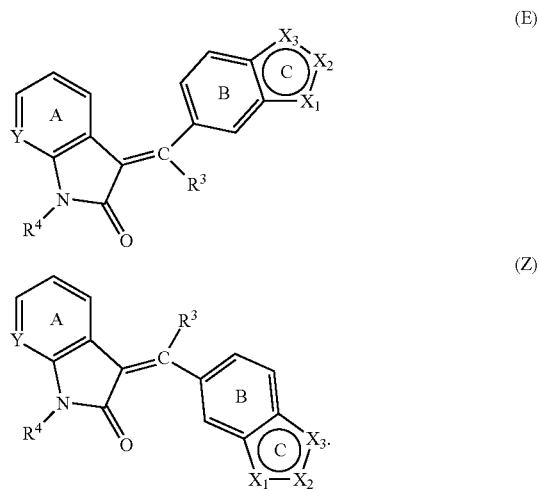

Accordingly, the compounds depicted by Structural Formulas (I')-(XIII') include the pure E geometric isomer, the pure Z geometric isomer, and mixture thereof.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of both geometric isomers in the mixture.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts include salts of inorganic acids (such as hydrochloric acid, hydrobromic, phosphoric, metaphosphoric, nitric, and sulfuric acids) and of organic acids (such as, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, and tartaric acids). Compounds with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

The term "halo" as used herein means halogen and includes chloro, fluoro, bromo and iodo.

An "aliphatic group" is acyclic, non-aromatic, consists solely of carbon and hydrogen and may optionally contain one or more units of unsaturation, e.g., double and/or triple bonds. An aliphatic group may be straight chained or branched. An aliphatic group typically contains between about one and about twenty carbon atoms, typically between about one and about ten carbon atoms, more typically between about one and about six carbon atoms. A "substituted aliphatic group" is substituted at any one or more "substitutable carbon atoms". A "substitutable carbon atom" in an aliphatic group is a carbon in the aliphatic group that is bonded to one or more hydrogen atoms. One or more hydrogen atoms can be optionally replaced with a suitable substituent group. A "haloaliphatic group" is an aliphatic group, as defined above, substituted with one or more halogen atoms.

The term "alkyl" used alone or as part of a larger moiety, such as "alkoxy", "haloalkyl", "arylalkyl", "alkylamine", "dialkyamine", "alkylamino", "dialkyamino" "alkylcarbonyl", "alkoxycarbonyl" and the like, means saturated straight-chain or branched aliphatic group. As used herein, a $C_1$-$C_6$ alkyl group is referred to "lower alkyl." Similarly, the terms "lower alkoxy", "lower haloalkyl", "lower arylalkyl", "lower alkylamine", lower dialkyamine", "lower alkylamino", "lower dialkyamino" "lower alkylcarbonyl", "lower alkoxycarbonyl" include straight and branched, saturated chains containing one to six carbon atoms.

The term "alkoxy" means —O-alkyl; "hydroxyalkyl" means alkyl substituted with hydroxy; "aralkyl" means alkyl substituted with an aryl group; "alkoxyalkyl" mean alkyl substituted with an alkoxy group; "alkylamine" means amine substituted with an alkyl group; "cycloalkylalkyl" means alkyl substituted with cycloalkyl; "dialkylamine" means amine substituted with two alkyl groups; "alkylcarbonyl" means —C(O)—R, wherein R is alkyl; "alkoxycarbonyl" means —C(O)—OR, wherein R is alkyl; and where alkyl is as defined above.

The terms "haloalkyl" and "haloalkoxy" means alkyl or alkoxy, as the case may be, substituted with one or more halogen atoms. The term "halogen" means F, Cl, Br or I. Preferably the halogen in a haloalkyl or haloalkoxy is F.

The term "acyl group" means —C(O)R, wherein R is an optionally substituted alkyl group or aryl group (e.g., optionally substituted phenyl). R is preferably an unsubstituted alkyl group or phenyl.

An "alkylene group" is represented by —[CH$_2$]$_z$—, wherein z is a positive integer, preferably from one to eight, more preferably from one to four.

An "alkenylene" is an alkylene group in which one methylene has been replaced with a double bond.

The term "aryl group" used alone or as part of a larger moiety as in "aralkyl", "aralkoxy", or "aryloxyalkyl", means a carbocyclic aromatic ring. The term "aryl" may be used interchangeably with the terms "aryl ring" "carbocyclic aromatic ring", "aryl group" and "carbocyclic aromatic group". An aryl group typically has six to fourteen ring atoms. Examples includes phenyl, naphthyl, anthracenyl, 1,2-dihydronaphthyl, 1,2,3,4-tetrahydronaphthyl, fluorenyl, indanyl, indenyl and the like. A "substituted aryl group" is substituted at any one or more substitutable ring atom, which is a ring carbon atom bonded to a hydrogen.

The term "heteroaryl", "heteroaromatic", "heteroaryl ring", "heteroaryl group", "heteroaromatic ring", and "heteroaromatic group", used alone or as part of a larger moiety as in "heteroaralkyl" or "heteroarylalkoxy", refers to aromatic ring groups having five to fourteen ring atoms selected from carbon and at least one (typically 1 to 4, more typically 1 or 2) heteroatoms (e.g., oxygen, nitrogen or sulfur). "Heteroaryl" includes monocyclic rings and polycyclic rings in which a monocyclic heteroaromatic ring is fused to one or more other carbocyclic aromatic or heteroaromatic rings. As such, "5-14 membered heteroaryl" includes monocyclic, bicyclic or tricyclic ring systems.

Examples of monocyclic 5-6 membered heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl. A "substituted heteroaryl group" is substituted at any one or more substitutable ring atom, which is a ring carbon or ring nitrogen atom bonded to a hydrogen.

The term "non-aromatic heterocyclic group" means a monocyclic, non-aromatic ring with 3 to 10-members containing from 1-3 ring heteroatoms or a polycyclic non-aromatic ring with 7 to 20-members and from 1 to 4 ring heteroatoms. Each heteroatom is independently selected from nitrogen, quaternary nitrogen, oxidized nitrogen (e.g., NO); oxygen; and sulfur, including sulfoxide and sulfone. The substituted non-aromatic heterocylic group may be attached via a suitable heteroatom or carbon atom. Representative non-aromatic heterocyclic groups include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A "substituted non-aromatic heterocylic group" is substituted at any one or more substitutable ring atom, which is a ring carbon or ring nitrogen atom bonded to a hydrogen.

Unless otherwise indicated, suitable substituents for a substituted aliphatic group, aryl group, heteroaryl group and non-aromatic heteroaryl groups include the groups represented by $R^a$. Other examples include halogen, nitro, cyano, hydroxy, $C_{1-20}$ alkyl, $C_{2-20}$ alkenyl, $C_{2-20}$ alkynyl, amino, $C_{1-20}$ alkylamino, $C_{1-20}$ dialkylamino, $C_{1-20}$ alkoxy, ($C_{1-10}$ alkoxy)$C_{1-20}$ alkyl, $C_{1-20}$ haloalkoxy, ($C_{1-10}$ haloalkoxy)$C_{1-20}$ alkyl and $C_{1-20}$ haloalkyl.

In accordance with another aspect, the compounds described herein can be prepared by processes analogous to those established in the art. Such processes may be found, for example, in WO 2009/079767, published Jul. 2, 2009 and WO 2010/115279, published Oct. 14, 2010.

A PLK4 antagonist can be a peptide (e.g., synthetic, recombinant, fusion or derivatized), which specifically binds to and inhibits (reduces, prevents, decreases) the activity of PLK4. The peptide can be linear, branched or cyclic, e.g., a peptide having a heteroatom ring structure that includes several amide bonds.

Peptides, including cyclic peptides, that are selective for binding to a particular domain (e.g., unique domain) of a PLK4 can be produced. A peptide can be, for example, derived or removed from a native protein by enzymatic or chemical cleavage, or can be synthesized by suitable methods, for example, solid phase peptide synthesis (e.g., Merrifield-type synthesis) (see, e.g., Bodanszky et al. "Peptide Synthesis," John Wiley & Sons, Second Edition, 1976). Peptides that are PLK4 antagonists can also be produced, for example, using recombinant DNA methodologies or other suitable methods (see, e.g., Sambrook J. and Russell D. W., Molecular Cloning: A Laboratory Manual, 3rd Edition, Cold Spring Harbor Laboratory Press, Cold Spring Harbor, N.Y., 2001). PLK4 antagonists can also be fusion peptides fused, for example to a carrier protein (e.g., myc, his, glutathione sulfhydryl transferase) and/or tagged (e.g., radiolabeled, fluorescently labeled).

A peptide can comprise any suitable L- and/or D-amino acid, for example, common α-amino acids (e.g., alanine, glycine, valine), non-α-amino acids (e.g., (β-alanine, 4-aminobutyric acid, 6-aminocaproic acid, sarcosine, statin), and unusual amino acids (e.g., citrulline, homocitrulline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "Protecting Groups in Organic Synthesis", John Wiley and Sons, 1991. The functional groups of a peptide can also be derivatized (e.g., alkylated) using art known methods.

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide antagonists can then be isolated using suitable methods. The peptide can comprise modifications (e.g., amino acid linkers, acylation, acetylation, amidation, methylation, terminal modifiers (e.g., cyclizing modifications)), if desired. The peptide can also contain chemical modifications (e.g., N-methyl-α-amino group substitution). In addition, the peptide antagonist can be an analog of a known and/or naturally-occurring peptide, for example, a peptide analog having conservative amino acid residue substitution(s). These modifications can improve various properties of the peptide (e.g., solubility, binding), including its PLK4 antagonist activity.

Peptidomimetic antagonists can be prepared by conventional chemical methods (see e.g., Damewood J. R. "Peptide Mimetic Design with the Aid of Computational Chemistry" in Reviews in Computational Biology, 2007, Vol. 9, pp. 1-80, John Wiley and Sons, Inc., New York, 1996; Kazmierski W. K., "Methods of Molecular Medicine: Peptidomimetic Protocols," Humana Press, New Jersey, 1999). Peptidomimetics can be prepared that are PLK4 antagonists. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for example, with the amino acid(s) at or near the ligand binding site. For example, the binding moieties in a peptidomimetic can be the same as those in a peptide or protein antagonist. The binding moieties can be an atom or chemical group which reacts with the PLK4 in the same or similar manner as the binding moiety in the peptide antagonist. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more -CONH-groups for a-NHCO-group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can then be isolated by suitable methods.

PLK4 antagonists are also agents that inhibit (reduce, decrease, prevent) the expression of PLK4. Agents (molecules, compounds, nucleic acids, oligonucleotides) which inhibit PLK4 gene expression (e.g., transcription, mRNA processing, translation) are effective PLK4 antagonists. For example, small interfering ribonucleic acids (siRNAs) and, similarly, short hairpin ribonucleic acids (shRNAs) which are processed into short siRNA-like molecules in a cell, can prevent the expression (translation) of the PLK4 protein. siRNA molecules can be polynucleotides that are generally about 20 to about 25 nucleotides long and are designed to bind specific RNA sequence (e.g., PLK4 mRNA). siRNAs silence gene expression in a sequence-specific manner, binding to a target RNA (e.g., an RNA having the complementary sequence) and causing the RNA to be degraded by endoribonucleases. siRNA molecules able to inhibit the expression of the PLK4 gene product can be produced by suitable methods. There are several algorithms that can be used to design siRNA molecules that bind the sequence of a gene of interest (see e.g., Mateeva O. et al. *Nucleic Acids Res.* 35(8):Epub, 2007; Huesken D. et al., *Nat. Biotechnol.* 23:995-1001; Jagla B. et al., *RNA* 11:864-872, 2005; Shabalinea S. A. *BMC Bioinformatics* 7:65, 2005; Vert J. P. et al. *BMC Bioinformatics* 7:520, 2006). Expression vectors that can stably express siRNA or shRNA are available. (See e.g., Brummelkamp, T. R., *Science* 296: 550-553, 2002, Lee, N S, et al., *Nature Biotechnol.* 20:500-505, 2002; Miyagishi, M., and Taira, K. *Nature Biotechnol.* 20:497-500, 2002; Paddison, P. J., et al., *Genes & Dev.* 16:948-958, 2002; Paul, C. P., et al., *Nature Biotechnol.* 20:505-508; 2002; Sui, G., et al., *Proc. Natl. Acad. Sci. USA* 99(6):5515-5520, 2002; Yu, J-Y, et al., *Proc. Natl. Acad. Sci. USA* 99(9):6047-6052, 2002; Elbashir, S M, et al., *Nature* 411:494-498, 2001.). Stable expression of siRNA/shRNA molecules is advantageous in the treatment of cancer as it enables long-term expression of the molecules, potentially reducing and/or eliminating the need for repeated treatments.

Antisense oligonucleotides (e.g., DNA, riboprobes) can also be used as PLK4 antagonists to inhibit PLK4 expression. Antisense oligonucleotides are generally short (~13 to ~25 nucleotides) single-stranded nucleic acids which specifically hybridize to a target nucleic acid sequence (e.g., mRNA) and induce the degradation of the target nucleic acid (e.g., degradation of the RNA through RNase H-dependent mechanisms) or sterically hinder the progression of splicing or translational machinery. (See e.g., Dias N. and Stein C. A., *Mol. Can. Ther.* 1:347-355, 2002). There are a number of different types of antisense oligonucleotides that can be used as PLK4 antagonists including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety is replaced by a morpholine ring), PN (N3'→P5' replacement of the oxygen at the 3' position on ribose by an amine group) and chimeric oligonucleotides (e.g., 2'-O-Methyl/phosphorothioate). Antisense oligonucleotides can be designed to be specific for PLK4 using predictive algorithms. (See e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Antisense oligonucleotides can be taken up by target cells (e.g., tumor cells) via the process of adsorptive endocytosis. Thus, in the treatment of a subject (e.g., mammalian), antisense PLK4 can be delivered to target cells (e.g., tumor cells) by, for example, injection or infusion. For instance, purified oligonucleotides or siRNA/shRNA, can be administered alone or in a formulation with a suitable drug delivery vehicle (e.g., liposomes, cationic polymers, (e.g., poly-L-lysine PAMAM dendrimers, polyalkylcyanoacrylate nanoparticles and polyethyleneimine) or coupled to a suitable carrier peptide (e.g., homeotic transcription factor, the Antennapedia peptide, Tat protein of HIV-1, E5CA peptide).

The PLK4 antagonist can be an antibody or antigen-binding fragment thereof which selectively binds a PLK4 protein. In a particular embodiment, the PLK4-specific antibody is a human antibody or humanized antibody. PLK4-specific antibodies can also be directly or indirectly linked to a cytotoxic agent.

Antibodies or antibody fragments which selectively bind to and inhibit the activity of a PLK4 can be produced, constructed, engineered and/or isolated by conventional methods or other suitable techniques. For example, antigen-specific antibodies can be raised against an appropriate immunogen, such as a recombinant mammalian (e.g., human) PLK4, or portion thereof (including synthetic molecules, e.g., synthetic peptides). A variety of methods have been described (see e.g., Kohler et al., Nature, 256: 495 497, 1975 and Eur. J. Immunol. 6: 511519, 1976; Milstein et al., Nature 266: 550 552, 1977; Koprowski et al., U.S. Pat. No. 4,172,124; Harlow, E. and D. Lane, *Antibodies: A Laboratory Manual*, (Cold Spring Harbor Laboratory: Cold Spring Harbor, N.Y.), 1988; Current Protocols In Molecular Biology, Vol. 2, Supp. 27, Summer 1994, Ausubel, F. M. et al., Eds., (John Wiley & Sons: New York, N.Y.), Chapter 11, 1991). Antibodies can also be raised by immunizing a suitable host (e.g., mouse) with cells that express PLK4 (e.g., cancer cells/cell lines) or cells engineered to express PLK4 (e.g., transfected cells) (see e.g., Chuntharapai et al., J. Immunol., 152:1783-1789, 1994; Chuntharapai et al. U.S. Pat. No. 5,440,021). For the production of monoclonal antibodies, a hybridoma can be produced by fusing a suitable immortal cell line (e.g., a myeloma cell line such as SP2/0 or P3X63Ag8.653) with antibody producing cells. The antibody producing cells can be obtained from the peripheral blood, or preferably, the spleen or lymph nodes, of humans or other suitable animals immunized with the antigen of interest. The fused cells (hybridomas) can be isolated using selective culture conditions, and cloned by limited dilution. Cells which produce antibodies with the desired specificity can be selected by a suitable assay (e.g., ELISA).

Antibody fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH1 domain and hinge region of the heavy chain. Single chain antibodies, and human, chimeric, humanized or primatized (CDR grafted), or veneered antibodies, as well as chimeric, CDR grafted or veneered single chain antibodies, comprising portions derived from different species, and the like are also encompassed by the present teachings and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, et al., WO 86/01533; Neuberger, et al., European Patent No. 0,194,276 B1; Winter, U.S. Pat. No. 5,225,539; Winter, European Patent No. 0,239, 400 B1; Queen et al., European Patent No. 0 451 216 B1; and Padlan, et al., EP 0 519 596 A1. See also, Newman, R. et al., BioTechnology, 10: 1455 1460 (1992), regarding primatized antibody, and Ladner et al., U.S. Pat. No. 4,946,778 and Bird, R. E. et al., Science, 242: 423 426, 1988 regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404, 1989); Sato, K., et al., Cancer Research, 53: 851856, 1993; Daugherty, B. L. et al., Nucleic Acids Res., 19(9): 2471 2476, 1991; and Lewis and Crowe, Gene, 101: 297 302, 1991). Using these or other suitable methods, variants can also be readily produced. In one embodiment, cloned variable regions (e.g., dAbs) can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Other suitable methods of producing or isolating antibodies of the requisite specificity can be used, including, for example, methods which select a recombinant antibody or antibody-binding fragment (e.g., dAbs) from a library (e.g., a phage display library), or which rely upon immunization of transgenic animals (e.g., mice). Transgenic animals capable of producing a repertoire of human antibodies are well-known in the art (e.g., Xenomouse® (Abgenix, Fremont, Calif.)) and can be produced using suitable methods (see e.g., Jakobovits et al., Proc. Natl. Acad. Sci. USA, 90: 2551 2555, 1993; Jakobovits et al., Nature, 362: 255 258, 1993; Lonberg et al., U.S. Pat. No. 5,545,806; Surani et al., U.S. Pat. No. 5,545,807; Lonberg et al., WO 97/13852).

Methods for Therapy

One aspect of the present teachings relates to a method for inhibiting the growth of a tumor (e.g., by directly inhibiting tumor growth) that expresses a mutant PTEN comprising administering to a patient with the tumor a therapeutically effective amount (e.g., an anti-tumor effective amount) of a PLK4 antagonist. In one embodiment, a therapeutically effective amount is an amount that is sufficient to inhibit (e.g., reduce, prevent or retard) tumor cell growth (e.g., as measured by tumor cell proliferation, tumor size or mass, tumor differentiation or de-differentiation and/or tumor progression (e.g., increased malignancy) for a particular cancer.

In one aspect, a small molecule PLK4 antagonist is used to treat a cancer patient, wherein the cancer is characterized by a mutant PTEN. In another embodiment, the cancer patient is a breast cancer patient. In a further embodiment, the breast cancer patient has or is diagnosed with a basal subtype breast cancer. In another embodiment, the cancer patient is a colon cancer patient.

In one aspect, the PLK4 antagonist directly inhibits the growth of the tumor by inducing apoptosis of the tumor cells or by inhibiting proliferation of the tumor cells. The PLK4 antagonist can inhibit PLK4 gene expression (e.g., using siRNA, antisense oligonucleotides) or PLK4 protein activity (e.g., using an antibody, peptide, peptide mimetic) of PLK4, thereby directly inhibiting the growth of the cells of the tumor.

Another aspect of the present teachings is a method for treating a basal subtype breast cancer in a patient. The method comprises administering to the patient a therapeutically effective amount of a PLK4 antagonist. In one embodiment, the administered PLK4 antagonist inhibits tumor growth directly by inducing the death (e.g., apoptosis) of the cells of the tumor or by inhibiting the growth (e.g., proliferation) of the cells of the tumor.

A further aspect of the present teachings is a method for treating colon cancer in a patient. The method comprises administering to the patient a therapeutically effective amount of a PLK4 antagonist. In one embodiment, the administered PLK4 antagonist inhibits tumor growth directly by inducing the death (e.g., apoptosis) of the cells of the tumor or by inhibiting the growth (e.g., proliferation) of the cells of the tumor.

The effectiveness of a therapy (e.g., the reduction or elimination of a tumor, the prevention or inhibition of tumor growth) can be determined by any suitable method (e.g., in situ immunohistochemistry, imaging (MRI, NMR), 3H-thymidine incorporation).

The methods described herein comprise administering a PLK4 antagonist. The PLK4 antagonist may be administered to the individual in need thereof as a primary therapy (e.g., as the principal therapeutic agent in a therapy or treatment regimen); as an adjunct therapy (e.g., as a therapeutic agent used together with another therapeutic agent in a therapy or treatment regime, wherein the combination of therapeutic agents provides the desired treatment; "adjunct therapy" is also referred to as "adjunctive therapy"); in combination with an adjunct therapy; as an adjuvant therapy (e.g., as a therapeutic agent that is given to the subject in need thereof after the principal therapeutic agent in a therapy or treatment regimen has been given); or in combination with an adjuvant therapy (e.g., chemotherapy (e.g., dacarbazine (DTIC), Cis-platinum, cimetidine, tamoxifen, cyclophophamide), radiation therapy, hormone therapy (e.g., anti-estrogen therapy, androgen deprivation therapy (ADT), luteinizing hormone-releasing hormone (LH-RH) agonists, aromatase inhibitors (AIs, such as anastrozole, exemestane, letrozole), estrogen receptor modulators (e.g., tamoxifen, raloxifene, toremifene)), or biological therapy). Numerous other therapies can also be administered during a cancer treatment regime to mitigate the effects of the disease and/or side effects of the cancer treatment including therapies to manage pain (narcotics, acupuncture), gastric discomfort (antacids), dizziness (anti-veritgo medications), nausea (anti-nausea medications), infection (e.g., medications to increase red/white blood cell counts) and the like, all of which are readily appreciated by the person skilled in the art.

Thus, a PLK4 antagonist can be administered as an adjuvant therapy (e.g., with another primary cancer therapy or treatment). As an adjuvant therapy, the PLK4 antagonist can be administered before, after or concurrently with a primary therapy like radiation and/or the surgical removal of a tumor(s). In some embodiments, the method comprises administering a therapeutically effective amount of a PLK4 antagonist and one or more other therapies (e.g., adjuvant therapies, other targeted therapies). An adjuvant therapy (e.g., a chemotherapeutic agent) and/or the one or more other targeted therapies and the PLK4 antagonist can be co-administered simultaneously (e.g., concurrently) as either separate formulations or as a joint formulation. Alternatively, the therapies can be administered sequentially, as separate compositions, within an appropriate time frame (e.g., a cancer treatment session/interval such as 1.5 to 5 hours) as determined by the skilled clinician (e.g., a time sufficient to allow an overlap of the pharmaceutical effects of the therapies). The adjuvant therapy and/or one or more other targeted therapies and the PLK4 antagonist can be administered in a single dose or multiple doses in an order and on a schedule suitable to achieve a desired therapeutic effect (e.g., inhibition of tumor growth).

One or more PLK4 antagonists can be administered in single or multiple doses. Suitable dosing and regimens of administration can be determined by a clinician and are dependent on the agent(s) chosen, pharmaceutical formulation and route of administration, various patient factors and other considerations. With respect to the administration of a PLK4 antagonist with one or more other therapies or treatments (adjuvant, targeted, cancer treatment-associated, and the like) the PLK4 antagonist is typically administered as a single dose (by e.g., injection, infusion, orally), followed by repeated doses at particular intervals (e.g., one or more hours) if desired or indicated.

The amount of the PLK4 antagonist to be administered (e.g., a therapeutically effective amount, an anti-tumor effective amount) can be determined by a clinician using the guidance provided herein and other methods known in the art and is dependent on several factors including, for example, the particular agent chosen, the subject's age, sensitivity, tolerance to drugs and overall well-being. For example, suitable dosages for a small molecule can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages for antibodies can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg body weight per treatment. Where the PLK4 antagonist is a polypeptide (linear, cyclic, mimetic), the preferred dosage will result in a plasma concentration of the peptide from about 0.1 µg/mL to about 200 µg/mL. Determining the dosage for a particular agent, patient and cancer is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

Methods for Administration

In one aspect of the present teachings, an "anti-tumor effective amount" of a PLK4 antagonist is administered to a patient in need thereof. For example, agents which directly inhibit tumor growth (e.g., chemotherapeutic agents) are conventionally administered at a particular dosing schedule and level to achieve the most effective therapy (e.g., to best kill tumor cells). Generally, about the maximum tolerated dose is administered during a relatively short treatment period (e.g., one to several days), which is followed by an off-therapy period. In a particular example, the chemotherapeutic cyclophosphamide is administered at a maximum tolerated dose of 150 mg/kg every other day for three doses, with a second cycle given 21 days after the first cycle. (Browder et al., Can. Res. 60:1878-1886, 2000).

An anti-tumor effective amount of PLK4 which directly inhibits the expression or activity of PLK4 in a tumor cell (e.g., neutralizing antibodies, inhibitory nucleic acids (e.g., siRNA, antisense nucleotides)) can be administered, for example, in a first cycle in which the maximum tolerated dose of the antagonist is administered in one interval/dose, or in several closely spaced intervals (minutes, hours, days) with another/second cycle administered after a suitable off-therapy period (e.g., one or more weeks). Suitable dosing schedules and amounts for a PLK4 antagonist can be readily determined by a clinician of ordinary skill. Decreased toxicity of a particular PLK4 antagonist as compared to chemotherapeutic agents can allow for the time between administration cycles to be shorter. When used as an adjuvant therapy (to, e.g., surgery, radiation therapy, other primary therapies), an anti-tumor effective amount of a PLK4 antagonist is preferably administered on a dosing schedule that is similar to that of the other cancer therapy (e.g., chemotherapeutics), or on a dosing schedule determined by the skilled clinician to be more/most effective at inhibiting (reducing, preventing) tumor growth.

A treatment regimen for an anti-tumor effective amount of a small molecule PLK4 antagonist can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg, every 1 to 7 days over a period of about 4 to about 6 months.

A treatment regimen for an anti-tumor effective amount of an antibody PLK4 antagonist can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg body weight per treatment, every 1 to 7 days over a period of about 4 to about 6 months.

A variety of routes of administration can be used including, for example, oral, dietary, topical, transdermal, rectal, parenteral (e.g., intravenous, intraarterial, intramuscular, subcutaneous injection, intradermal injection), intravenous infusion and inhalation (e.g., intrabronchial, intranasal or oral inhalation, intranasal drops) routes of administration, depending on the agent and the particular cancer to be treated. Administration can be local or systemic as indicated. The preferred mode of administration can vary depending on the particular agent chosen. In one embodiment, intravenous infusion is preferred (e.g., to administer neutralizing PLK4 antibodies).

The agent (such as a PLK4 antagonist) can be administered to a mammalian subject as part of a pharmaceutical or physiological composition. For example, the agent can be administered as part of a pharmaceutical composition for inhibition of PLK4 expression (e.g., inhibition of PLK4 gene expression and/or inhibition of PLK4 activity) and a pharmaceutically acceptable carrier. Formulations or compositions comprising a PLK4 antagonist or compositions comprising a PLK4 antagonist and one or more other therapeutic agents will vary according to the route of administration selected (e.g., solution, emulsion or capsule). Suitable pharmaceutical carriers can contain inert ingredients which do not interact with the PLK4 antagonist. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

For example, a nucleic acid-based PLK4 antagonist (e.g., siRNA, shRNA, antisense oligonucleotide, natural or synthetic nucleic acids, nucleic acid analogs, aptamers) can be introduced into a mammalian subject in a number of ways. For instance, chemically synthesized or in vitro transcribed nucleic acids can be transfected into cells in cell culture by any suitable method (e.g., viral infection). The nucleic acids may also be expressed endogenously from expression vectors or PCR products in host cells or packaged into synthetic or engineered compositions (e.g., liposomes, polymers, nanoparticles) that can then be introduced directly into the bloodstream of a mammalian subject (by, e.g., injection, infusion). Anti-PLK4 nucleic acids or nucleic acid expression vectors (e.g., retroviral, adenoviral, adeno-associated and herpes simplex viral vectors, engineered vectors, non-viral-mediated vectors) can also be introduced into a mammalian subject directly using established gene therapy strategies and protocols (see e.g., Tochilin V. P. Annu. Rev. Biomed. Eng. 8:343-375, 2006; Recombinant DNA and Gene Transfer, Office of Biotechnology Activities, National Institutes of Health Guidelines).

Similarly, where the agent is a protein or polypeptide, the agent can be administered via in vivo expression of recombinant protein. In vivo expression can be accomplished by somatic cell expression according to suitable methods (see, e.g., U.S. Pat. No. 5,399,346). Further, a nucleic acid encoding the polypeptide can also be incorporated into retroviral, adenoviral or other suitable vectors (often a replication deficient infectious vector) for delivery, or can be introduced into a transfected or transformed host cell capable of expressing the polypeptide for delivery. In the latter embodiment, the cells can be implanted (alone or in a barrier device), injected or otherwise introduced in an amount effective to express the polypeptide in a therapeutically effective amount.

The invention is illustrated by the following examples which are not intended to be limiting in any way.

EXEMPLIFICATION

Materials and Methods
Sulforhodamine B (SRB) Assay

Breast cancer and normal cells were seeded at various concentrations, ranging from 1500 to 4000 per 80 μl according to cell growth rate, into 96-well plates 24 hours before compound overlay. Each 10 mM stock solution in 100% DMSO of the compounds was diluted with Opti-MEM I Reduced-Serum Medium (Invitrogen, Canada) to make concentration ranges from 50 nM to 250 μM. 20 μl from each concentration was added to the cells to make the final concentration range from 10 nM to 50 μM. The cells were cultured at 37° C. for 5 days before the Sulforhodamine B (SRB) assay was performed to assess cell survival. SRB is a water-soluble dye that binds to the basic amino acids of cellular proteins. Thus, colorimetric measurement of the bound dye provides an estimate of the total protein mass and is related to cell number. The cells were fixed in situ by gently aspirating off the culture media and adding 50 μl ice-cold 10% Trichloroacetic Acid (TCA) per well and incubation at 4° C. for 30-60 min. The plates were washed with tap water five times and allowed to air dry for 5 min. 50 μl of 0.4% (w/v) SRB solution in 1% (v/v) acetic acid was added per well and incubated for 30 mM at RT for staining. Following staining, plates were washed four times with 1% acetic acid to remove any unbound dye and then allowed to air dry for 5 min. The stain was solubilized with 100 μl of 10 mM Tris pH 10.5 per well. Absorbances were read at 570 nm. The cell survival percentage at each compound concentration was calculated over the cell DMSO control, which was growing in the presence of 0.1% DMSO (0.5% in the case of 50 μM compounds). Cell viability $GI_{50}$ values were calculated using GraphPad PRISM software (GraphPad Software, Inc.).

Cell Cycle and Annexin V Analysis

Breast cancer cells were seeded at various concentrations, ranging from $1 \times 10^5$ to $2.5 \times 10^5$ per well according to cell growth rate, into 6-well plates 24 hours before siRNA and/or compound treatment. Each 10 mM stock solution in 100% DMSO of the compounds was diluted with Opti-MEM I Reduced-Serum Medium (Invitrogen, Canada) and added to the cells to the stated final concentrations. Control cells received 0.001% DMSO alone. Where indicated, 40 nM PTEN siRNAs (siPTEN) (QIAGEN, Canada; sense sequence: 5'-GGCGUAUACAGGAACAAUA-3') or 40 nM control siRNA (siCTRL) (QIAGEN, Canada) were transfected into cells using Lipofectamine 2000 according to the manufacturer's protocol (Invitrogen, Canada). Prior to analysis, cells were trypsinized, washed in 1× phosphate-buffered saline (PBS) and centrifuged. For cell cycle analysis, cells were resuspended in 0.1% bovine serum albumin in PBS, fixed in ethanol and stained with propidium iodide in Hepes buffer. For Annexin V assays, cell pellets were resuspended in 1× binding buffer, FITC Annexin V and propodium iodide were added at final concentrations of 0.25 micrograms per mL and 0.5 micrograms per mL, respectively. All samples were read in a FACSCalibur flow cytometer (Becton, Dickinson and Company), and data analyzed using FloJo software (Tree Star, Inc.).

Western Immunoblot Analysis

Cells were rinsed in ice-cold PBS and lysed in lysis buffer (50 mM Tris pH 8.0, 10% glycerol, 1% Triton X-100, 150 mM NaCl) supplemented with 1 mM sodium orthovanadate, 1 mM phenylmethylsulfonyl fluoride (PMSF) and Complete Mini Protease Inhibitors (Roche). Proteins were separated by SDS-PAGE, transferred to polyvinylidene fluoride (PVDF) membrane, and immunoblotted with antibodies against cleaved PARP (Cell Signaling Technology, Inc.), GAPDH (Millipore) or PTEN (Cascade Bioscience). Blots were developed using the Odyssey Infrared Imager (LI-COR Biosciences).

Immunofluorescence Microscopy

MDA-MB-231 or MDA-MB-468 cells were seeded at a density of 10,000 cells per well in eight-well chamber slides (Nalge NUNC Labware) and treated with 0.1 μM PLK4 inhibitor 21 or DMSO. After 3 days, the cells were rinsed briefly in PBS, fixed with 4% paraformaldehyde in PBS for 15 min, permeabilized with 0.1% Triton X-100 in PBS for 5 min, and placed in blocking solution (0.5% bovine serum albumin, 6% normal goat serum in PBS) for 1 hour at room temperature. Samples were incubated overnight at 4° C. with rabbit antibodies against cleaved PARP (Cell Signaling Technology, Inc.) and mouse antibodies against alpha-tubulin (Sigma Inc.) at a concentration of 1 μg/ml in blocking solution. Alexa 488-conjugated anti-rabbit and Alexa 555-conjugated anti-mouse antibodies (Molecular Probes) were used to detect primary antibodies. Nuclei were visualized by staining with Hoechst reagent (Invitrogen, Canada) at a concentration of 0.5 μg/ml. Microscopy was carried out using a Leica DM 5000B microscope equipped with fluorescence optics.

Example A

Syntheses of Compounds of the Invention

Compounds falling within the general formulas described herein were synthesized using techniques known in the art. For example, exemplary compounds are synthesized in WO 2009/079767, published Jul. 2, 2009 (see, e.g., pages 81-212). Other exemplary compounds are synthesized in WO 2010/115279, published Oct. 14, 2010 (see, e.g., pages 52-304).

Example B

PLK4 Inhibition Assay

Active PLK4 was purified from an *E. coli* expression system as an amino terminal GST fusion of residues 1-391 of human PLK4. The protein was purified from clarified cell extracts after induction at 15° C. overnight using glutathione sepharose, gel permeation chromatography, and ion exchange (Resource Q). The resulting protein was dephosphorylated with lambda phosphatase (NEB cat# P0753), and resolved from the phosphatase using gluthione sepharose. The dephosphorylated GST-PLK4 was stored in aliquots at −80° C. until use.

PLK4 activity was measured using an indirect ELISA detection system. Dephosphorylated GST-PLK4 (4 nM) was incubated in the presence of 15 μM ATP (Sigma cat# A7699), 50 mM HEPES-$Na^{2+}$ pH 7.4, 10 mM $MgCl_2$, 0.01% Brij 35 (Sigma cat#03-3170), in a 96 well microtitre plate pre-coated with MBP (Millipore cat#30-011). The reaction was allowed to proceed for 30 minutes, followed by 5 washes of the plate with Wash Buffer (50 mM TRIS-Cl pH 7.4 and 0.2% Tween 20), and incubation for 30 minutes with a 1:3000 dilution of primary antibody (Cell Signaling cat#9381). The plate was washed 5 times with Wash Buffer, incubated for 30 minutes in the presence of secondary antibody coupled to horse radish peroxidase (BioRad cat#1721019, 1:3000 concentration), washed an additional 5 times with Wash Buffer, and incubated in the presence of TMB substrate (Sigma cat# T0440). The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 µM) or at a variable inhibitor concentration (typically 50 µM to 0.1 µM in a 10 point dose response titration). Compounds were pre-incubated in the presence of enzyme for 15 minutes prior to addition of ATP and the activity remaining quantified using the above described activity assay. The % Inhibition of a compound was determined using the following formula; % Inhibition=100×(1−(experimental value−background value)/(high activity control−background value)). The $IC_{50}$ value was determined using a non-linear 4 point logistic curve fit (XLfit4, IDBS) with the formula;

$(A+(B/(1+((x/C)^D))))$, where A=background value, B=range, C=inflection point, D=curve fit parameter.

Example C

PLK1 Inhibition Assay

PLK1 inhibition was determined using the Z-Lyte assay kit from Invitrogen (cat#PV3802). The assay was performed using the recommended manufacturer's instructions with 25 µM ATP and 8 nM PLK1 (Invitrogen cat #PV3501). The % inhibition values were determined according to the manufacturer's directions and $IC_{50}$ values were obtained using a non-linear 4 point logistic curve fit (XLfit4, IDBS)

Example D

PLK2 Inhibition Assay

PLK2 inhibition was determined using the Z-Lyte assay kit from Invitrogen (cat# PV3802). The assay was performed using the recommended manufacturer's instructions with 60 µM ATP and 133 nM PLK2 (Invitrogen cat #PV4204). The % inhibition values were determined according to the manufacturer's directions and $IC_{50}$ values were obtained using a non-linear 4 point logistic curve fit (XLfit4, IDBS)

Example E

Aurora A Inhibition Assay

Aurora A inhibition was determined using the Z-Lyte assay kit from Invitrogen. The assay was performed using the recommended manufacturer's instructions with 20 nM ATP and 12 nM Aurora A (Invitrogen cat #PV3612). The % inhibition values were determined according to the manufacturer's directions and $IC_{50}$ values were obtained using a non-linear 4 point logistic curve fit (XLfit4, IDBS)

Example F

Aurora B Inhibition Assay

Aurora B inhibition was determined using the Z-Lyte assay kit from Invitrogen. The assay was performed using the recommended manufacturer's instructions with 128 µM ATP and 28 nM Aurora B (Invitrogen cat #PV3970). The % inhibition values were determined according to the manufacturer's directions and $IC_{50}$ values were obtained using a non-linear 4 point logistic curve fit (XLfit4, IDBS).

In Table 1, $IC_{50}$ values for PLK4, PLK1, PLK2, Aurora A and Aurora B Kinases are indicated as "A," "B," and "C," for those less than or equal to 5 µM; those greater than 5 µM and less than or equal to 50 µM; and those greater than 50 µM, respectively. The relative inhibition percentages at a dose of 10 µM are indicated as "X" and "Y" for those equal to or greater than 50% inhibition and those less than 50% inhibition, respectively. As shown in Table 1, compounds have been identified, which are effective PLK inhibitors, in particular PLK4 inhibitors. In addition, a number of compounds also inhibit Aurora kinases, in particular Aurora B kinase.

TABLE 1

Inhibition Data of PLK4, PLK1, PLK2, Aurora A and Aurora B Kinases

| | IC50 Ranges | | | | |
|---|---|---|---|---|---|
| Compound # | PLK4 | PLK1 | PLK2 | Aurora A | Aurura B |
| 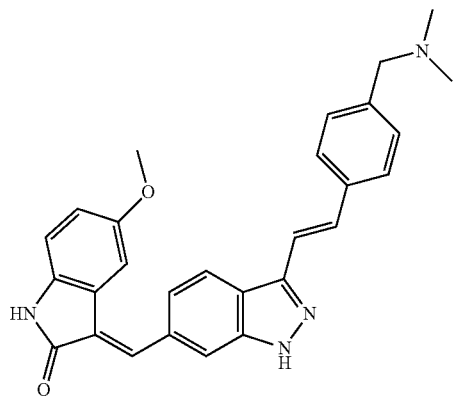 [SMILES: COc1ccc2c(c1)/C(=C\c1ccc3c(/C=C/c4ccc(CN(C)C)cc4)n[nH]c3c1)C(=O)N2] | A | | | — | A |

TABLE 1-continued
Inhibition Data of PLK4, PLK1, PLK2, Aurora A and Aurora B Kinases
| Compound # | PLK4 | PLK1 | PLK2 | Aurora A | Aurura B |
|---|---|---|---|---|---|
| 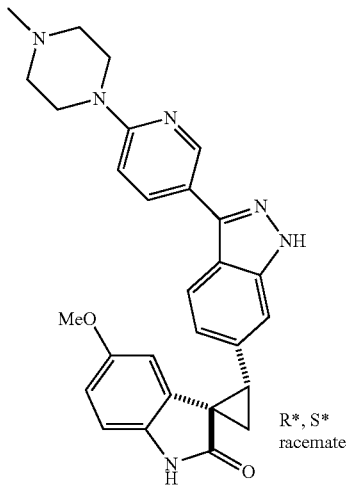 2 | A | — | — | Y | A |
| 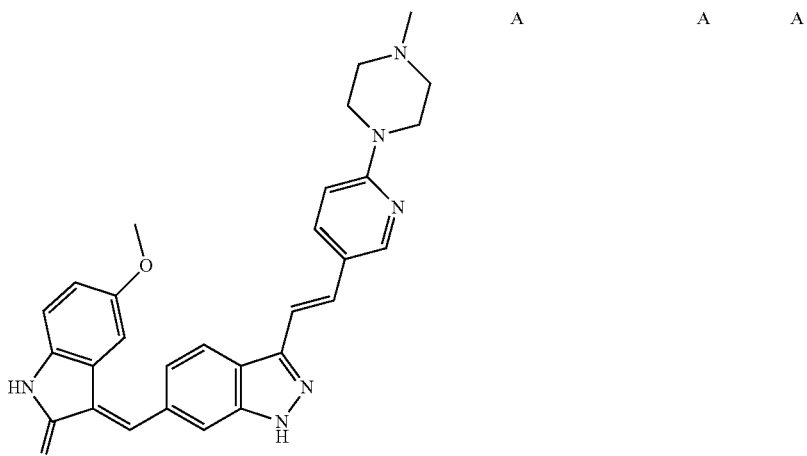 3 | A |  |  | A | A |
| 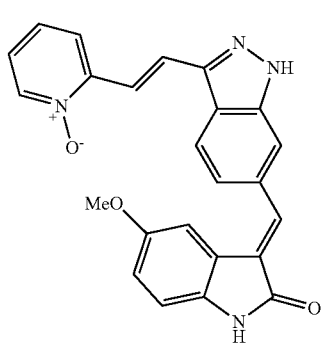 4 | A | — | — | — | A |

TABLE 1-continued
Inhibition Data of PLK4, PLK1, PLK2, Aurora A and Aurora B Kinases
| Compound # | PLK4 | PLK1 | PLK2 | Aurora A | Aurura B |
|---|---|---|---|---|---|
| 5 | A | Y | Y | A | A |
| 6 | A | Y | Y | A | A |
| 7 | A | Y | Y | A | A |
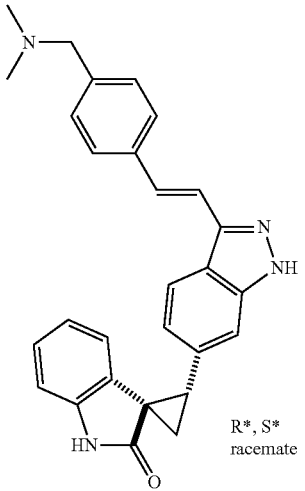
5  R*, S* racemate
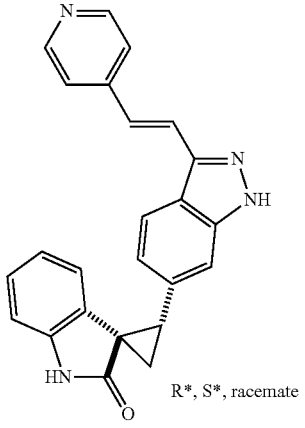
6  R*, S*, racemate
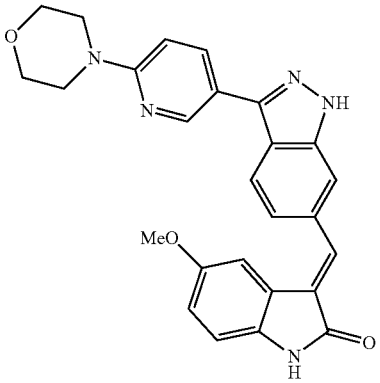 [SMILES: COc1ccc2c(c1)/C(=C\c1ccc3c(-c4ccc(N5CCOCC5)nc4)n[nH]c3c1)C(=O)N2]
7

TABLE 1-continued
Inhibition Data of PLK4, PLK1, PLK2, Aurora A and Aurora B Kinases
| Compound # | PLK4 | PLK1 | PLK2 | Aurora A | Aurora B |
|---|---|---|---|---|---|
| 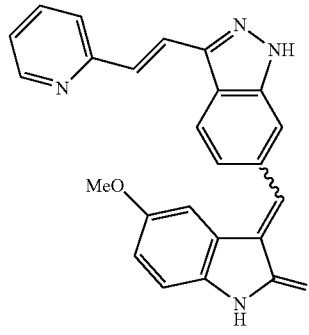 8 | A | Y | Y | X | A |
| 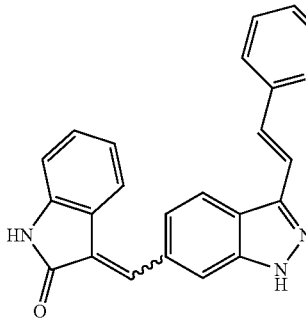 9 | A | C | C | A | A |
| 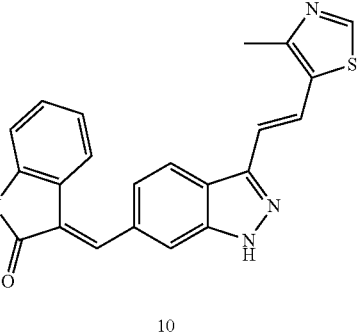 10 | A | Y | Y | X | A |
| 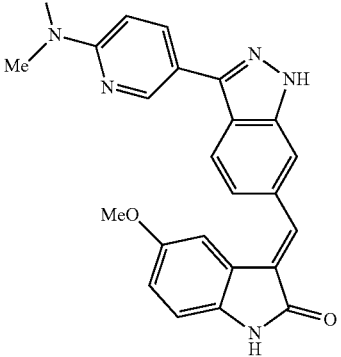 11 | A | Y | Y | A | A |

TABLE 1-continued
Inhibition Data of PLK4, PLK1, PLK2, Aurora A and Aurora B Kinases
| Compound # | PLK4 | PLK1 | PLK2 | Aurora A | Aurura B |
|---|---|---|---|---|---|
| 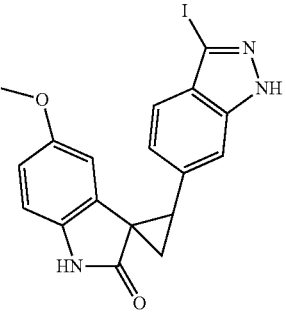 [SMILES: COc1ccc2c(c1)C1(CC1c1ccc3c(I)n[nH]c3c1)C(=O)N2] 12 | A | — | — | — | — |
| 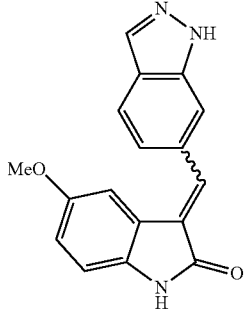 [SMILES: COc1ccc2c(c1)C(=Cc1ccc3cn[nH]c3c1)C(=O)N2] 13 | A | X | X | X | A |
| 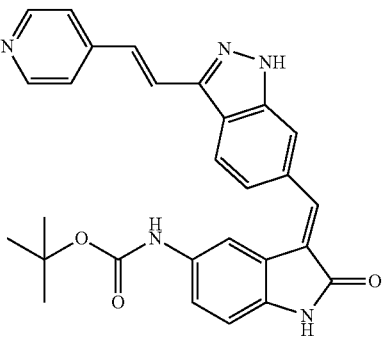 [SMILES: CC(C)(C)OC(=O)Nc1ccc2c(c1)/C(=C\c1ccc3c(/C=C/c4ccncc4)n[nH]c3c1)C(=O)N2] 14 | A | — | — | — | A |
| 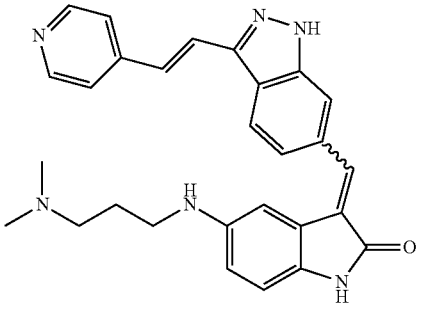 [SMILES: CN(C)CCCNc1ccc2c(c1)C(=Cc1ccc3c(/C=C/c4ccncc4)n[nH]c3c1)C(=O)N2] 15 | A | | | — | A |

TABLE 1-continued

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| 16 | A | Y | Y | A | A |
| 17 | A | | | B | A |
| 18 | A | B | X | X | B |
| 24 | A | B | B | Y | A |

TABLE 1-continued

Inhibition Data of PLK4, PLK1, PLK2, Aurora A and Aurora B Kinases

| Compound # | PLK4 | PLK1 | PLK2 | Aurora A | Aurora B |
|---|---|---|---|---|---|
| 25 | A | B | — | — | — |
| 26 | A | B | B | A | A |
| 27 | A | A | — | — | — |
| 28 | A | Y | X | A | A |

TABLE 1-continued
Inhibition Data of PLK4, PLK1, PLK2, Aurora A and Aurora B Kinases
| Compound # | IC50 Ranges | | | | |
| --- | --- | --- | --- | --- | --- |
| | PLK4 | PLK1 | PLK2 | Aurora A | Aurura B |
| | A | Y | Y | A | A |
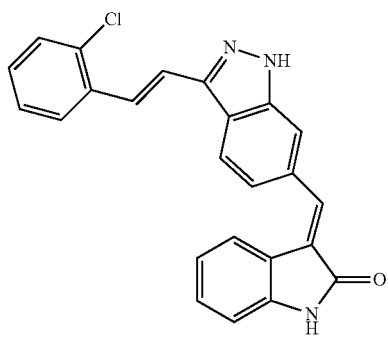 [SMILES: O=C1Nc2ccccc2/C1=C\c1ccc2c(/C=C/c3ccccc3Cl)n[nH]c2c1]
29
| | A | — | — | — | — |
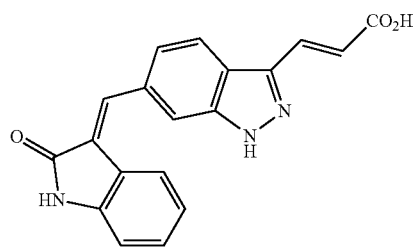 [SMILES: O=C(O)/C=C/c1n[nH]c2cc(/C=C3/C(=O)Nc4ccccc43)ccc12]
30
| | A | — | — | — | A |
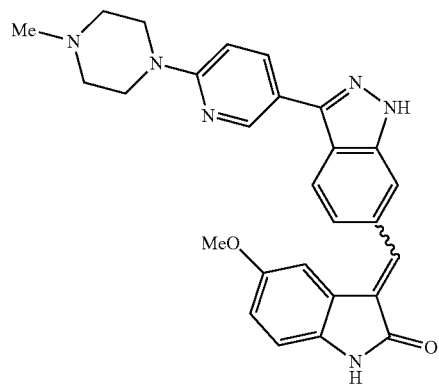 [SMILES: COc1ccc2c(c1)C(=Cc1ccc3c(-c4ccc(N5CCN(C)CC5)nc4)n[nH]c3c1)C(=O)N2]
31

TABLE 1-continued
Inhibition Data of PLK4, PLK1, PLK2, Aurora A and Aurora B Kinases
| Compound # | PLK4 | PLK1 | PLK2 | Aurora A | Aurora B |
|---|---|---|---|---|---|
| | A | Y | Y | A | A |
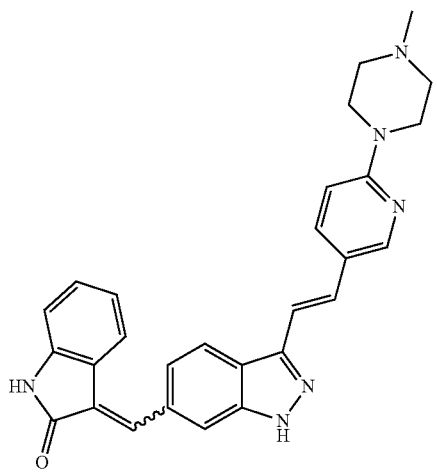 [SMILES: CN1CCN(c2ccc(/C=C/c3n[nH]c4cc(C=C5C(=O)Nc6ccccc65)ccc34)cn2)CC1]
32
| | A | Y | Y | A | A |
|---|---|---|---|---|---|
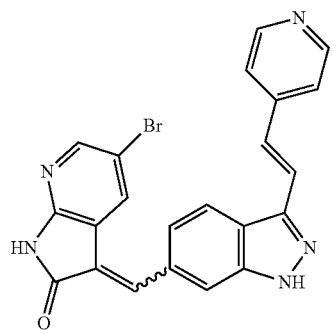 [SMILES: O=C1Nc2ncc(Br)cc2C1=Cc1ccc2c(/C=C/c3ccncc3)n[nH]c2c1]
33
| | A | Y | Y | A | — |
|---|---|---|---|---|---|
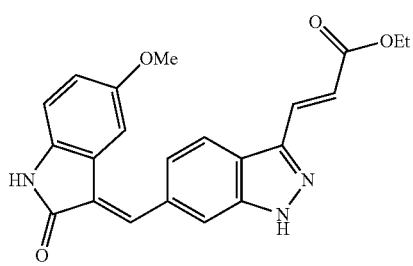 [SMILES: CCOC(=O)/C=C/c1n[nH]c2cc(/C=C3/C(=O)Nc4ccc(OC)cc43)ccc12]
34

TABLE 1-continued
Inhibition Data of PLK4, PLK1, PLK2, Aurora A and Aurora B Kinases
| Compound # | IC50 Ranges | | | | |
|---|---|---|---|---|---|
| | PLK4 | PLK1 | PLK2 | Aurora A | Aurura B |
| 35 | A | — | — | — | — |
| 36 | A | | X | | A |
| 37 | A | | X | | A |
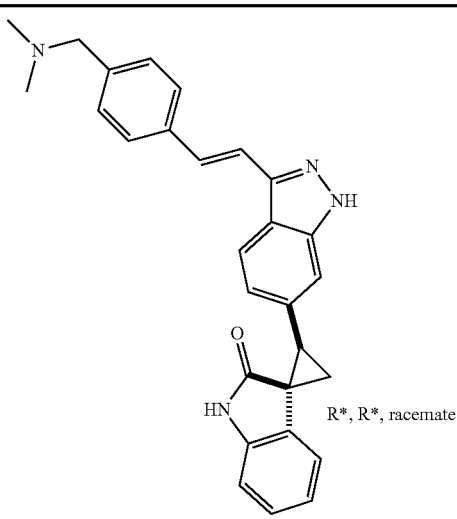

TABLE 1-continued

Inhibition Data of PLK4, PLK1, PLK2, Aurora A and Aurora B Kinases

| Compound # | IC50 Ranges | | | | |
|---|---|---|---|---|---|
| | PLK4 | PLK1 | PLK2 | Aurora A | Aurora B |
| 38 | A | | | X | A |
| 39 | A | Y | — | X | A |
| 40 R*, S*, racemate | A | — | C | — | A |

Additional data has been collected for further compounds and may be found, for example, in Examples B-F of WO 09/079,767, published Jul. 2, 2009 and in Examples B-G of WO 10/115,279, published Oct. 14, 2010.

Example H

Kinase Selectivity Assays

The inhibitory activity of selected compounds was evaluated against a panel of 45 different kinase enzymes by CEREP, France. The assays were performed using standard HTRF assay methods as documented by CEREP against the human orthologues of Abl kinase, Akt1/PKBa, AMPKa, BMX kinase (Etk), Brk, CaMK2a, CaMK4, CDC2/CDK1 (cycB), CHK1, CHK2, c-Met kinase, CSK, EphB4 kinase, ERK1, ERK2 (P42mapk), FGFR2 kinase, FGFR4 kinase, FLT-1 kinase (VEGFR1), FLT-3 kinase, Fyn kinase, IGF1R kinase, IRK (InsR), JNK 2, KDR kinase (VEGFR2), Lck kinase, Lyn kinase, MAPKAPK2, MEK1/MAP2K1, p38a kinase, p38d kinase, p38g kinase, PDGFRb kinase, PDK1, PKA, PKCa, PKCb1, PKCb2, PKCg, Ret kinase, ROCK2, RSK2, Src kinase, Syk, and TRKA. The % Inhibition was determined by the formula; % Inhibition=100×(1−(experimental value−background value)/(high activity control−background value)).

TABLE 2

Percent Inhibition Values For
Compounds 24, 26, 9, 29, 31 and 3 at 10 μM Concentration

| Kinase | % Inhibition at 10 μM Concentration | | | | | |
|---|---|---|---|---|---|---|
| | 24 | 26 | 9 | 29 | 31 | 3 |
| Abl | 34 | 24 | 100 | 40 | 99 | 23 |
| Akt1/PKBalpha | −3 | −4 | −3 | −14 | −4 | −5 |
| AMPKalpha | 15 | 54 | 81 | 8 | 76 | 34 |
| BMX (Etk) | 15 | −3 | 53 | 18 | 9 | 0 |
| Brk | 5 | −6 | 40 | 4 | 7 | −2 |
| CaMK2alpha | 4 | −3 | 31 | −2 | 14 | 2 |
| CaMK4 | 3 | 26 | 27 | −15 | 2 | 6 |
| CDC2/CDK1 | 2 | 9 | 62 | 18 | 15 | 11 |
| CDK2 (cycE) | 10 | 16 | 8 | 5 | 3 | — |
| CHK1 | −6 | −2 | 7 | −1 | 3 | 0 |
| CHK2 | 14 | 2 | 22 | 6 | 4 | −4 |
| c-Met | −20 | 2 | 35 | 0 | 28 | 2 |
| CSK | 8 | 5 | 86 | 17 | 51 | 6 |
| EphB4 | 5 | −5 | 85 | −14 | 6 | −1 |
| ERK1 | 6 | 6 | 13 | 1 | 10 | 2 |
| ERK (P42mapk) | 3 | 0 | 14 | 2 | −9 | 15 |
| FGFR2 | 68 | 31 | 97 | 10 | 35 | 4 |
| FGFR4 | 18 | −4 | 38 | 6 | 30 | −30 |
| FLT-1 (VEGFR1) | 0 | 16 | 99 | 42 | 73 | 30 |
| FLT-3 | 93 | 76 | 100 | 10 | 100 | 32 |
| Fyn | 24 | 5 | 91 | 70 | 13 | 4 |
| IGF1R | 7 | −4 | 43 | 81 | 4 | 5 |
| IRK (InsR) | 13 | 12 | 34 | 6 | 9 | 2 |
| JNK 2 | 13 | 14 | 52 | 3 | 14 | 15 |
| KDR (VEGFR2) | 59 | 29 | 100 | 8 | 93 | 32 |
| Lck | 15 | 0 | 88 | 30 | 89 | 13 |
| Lyn | 14 | −5 | 98 | 88 | 85 | −2 |
| MAPKAPK2 | 6 | 0 | 0 | 19 | 4 | 6 |
| MEK1/MAP2K1 | 20 | 3 | 46 | 16 | 9 | −3 |
| p38alpha | −8 | 18 | 16 | 1 | 11 | 22 |
| p38delta | 0 | −8 | −5 | 3 | 13 | −2 |
| p38gamma | 14 | 5 | 2 | 10 | 1 | 12 |
| PDGFRbeta | 46 | 19 | 100 | 2 | 0 | 14 |
| PDK1 | −3 | 2 | 4 | 1 | 73 | 5 |
| PKA | 9 | −1 | −4 | 7 | 0 | −5 |
| PKCalpha | 9 | 0 | 2 | −1 | 9 | 7 |
| PKCbeta 1 | 1 | −5 | −2 | 0 | 2 | 1 |
| PKCbeta 2 | 0 | 2 | 12 | 4 | 37 | 4 |
| PKCgamma | 9 | −6 | 0 | 3 | 0 | 3 |
| Ret | 67 | 41 | 98 | 33 | 93 | 33 |
| ROCK2 | 1 | 3 | −3 | −1 | 22 | −20 |
| RSK2 | 4 | 1 | 38 | 0 | 37 | −4 |
| Src | 10 | −9 | 59 | 0 | 24 | 26 |
| Syk | −2 | −3 | 70 | — | 21 | −1 |
| TRKA | −13 | 60 | 99 | 75 | 93 | 43 |

Table 2 shows the percent inhibition values obtained for Compounds 24, 26, 9, 29, 31 and 3 at 10 μM concentration. From this inhibition data it is apparent that certain kinases, e.g. Abl, FGFR2, FLT-1, FLT-3, KDR, Lyn, PDGFRbeta Ret and TRKA kinases are stongly inhibited (i.e. >95%) by compounds described herein at 10 μM. For a number of compounds, IC50 values were estimated against kinases of interest based on Millipore protocols. Kinase assays at Millipore were performed using a radiolabelled phosphopeptide filter binding detection system, in duplicate, at each compound concentration. The ATP substrate concentration in the reactions was at the Km for each enzyme.

To allow for a more direct comparison of compound inhibition, an IC50 value was estimated from the inhibition determined at three compound concentrations. Several assumptions were made to allow this calculation using a 4 parameter non linear curve fit model, including full inhibition set at 100%, no inhibition set to 0%, and a curve fit parameter set at 1. The inflection point was reported as the estimated 1050.

In Table 3, $IC_{50}$ value estimates against the Receptor Tyrosine Kinase family (e.g. Abl, FGFR2, FLT-1, KDR, Lyn, and PDGFRβ) are indicated as "A," "B," and "C," for those less than or equal to 5 μM; those greater than 5 μM and less than or equal to 50 μM; and those greater than 50 μM, respectively. These activities may impart additional therapeutic benefit to these compounds.

TABLE 3

$IC_{50}$ value estimates against
Ab1, FGFR2, FLT-1, KDR, Lyn, and PDGFRβ

| Compound # | Abl | FGFR1 | FLT-1 | KDR | Lyn | PDGFRβ | Ret | TrkA |
|---|---|---|---|---|---|---|---|---|
| 9 | A | A | A | A | A | A | A | A |
| 28 | A | A | A | A | A | A | A | A |
| 31 | A | A | A | A | B | B | A | A |
| 39 | A | A | A | A | A | A | A | A |

TABLE 4

Percent Inhibition Values For Examples
40, 2, 6 & 35 at 10 μM Concentration

| Kinase | 40 % Inhibition @ 10 uM | 2 % Inhibition @ 10 uM | 6 % Inhibition @ 10 uM | 35 % Inhibition @ 10 uM |
|---|---|---|---|---|
| Abl | 3 | 91 | 97 | 100 |
| Akt1/PKBalpha | −2 | −2 | −1 | −4 |
| AMPKalpha | 57 | 8 | 82 | 69 |
| BMX (Etk) | −3 | 3 | 71 | 39 |
| Brk | 1 | −1 | 41 | 53 |

TABLE 4-continued

Percent Inhibition Values For Examples
40, 2, 6 & 35 at 10 μM Concentration

| Kinase | 40 % Inhibition @ 10 uM | 2 % Inhibition @ 10 uM | 6 % Inhibition @ 10 uM | 35 % Inhibition @ 10 uM |
|---|---|---|---|---|
| CaMK2alpha | 41 | 1 | 82 | 9 |
| CaMK4 | 7 | −6 | −8 | −4 |
| CDC2/CDK1 | 57 | 5 | 93 | 60 |
| CHK1 | −4 | −9 | 37 | 43 |
| CHK2 | −10 | −5 | 4 | −3 |
| c-Met | 15 | −8 | 97 | 61 |
| CSK | 9 | 10 | 99 | 75 |
| EphB4 | 11 | 0 | 99 | 65 |
| ERK1 | 4 | −3 | 8 | 1 |
| ERK (P42mapk) | 9 | 2 | 11 | 2 |
| FGFR4 | 0 | −20 | 56 | −12 |
| FLT-1 (VEGFR1) | 1 | 22 | 82 | 30 |
| FLT-3 | 62 | 86 | 100 | 102 |
| Fyn | 7 | 2 | 87 | 55 |
| IGF1R | 20 | −3 | 22 | 0 |
| IRK (InsR) | 4 | −2 | 21 | 5 |
| JNK 2 | −2 | 11 | 32 | 5 |
| KDR (VEGFR2) | 14 | 6 | 98 | 58 |
| Lck | 17 | 71 | 97 | 100 |
| Lyn | 26 | 15 | 99 | 86 |
| MAPKAPK2 | −4 | −10 | 4 | 2 |
| MEK1/MAP2K1 | 4 | −2 | 12 | −2 |
| p38alpha | 6 | −28 | 32 | −22 |
| p38delta | −10 | 1 | −22 | 5 |
| p38gamma | 4 | −1 | −15 | −5 |
| PDGFRbeta | 4 | 3 | 88 | 59 |
| PDK1 | 4 | −2 | 69 | 2 |
| PKA | 0 | −2 | −6 | −7 |
| PKCalpha | −2 | 3 | 7 | 6 |
| PKCbeta 1 | 1 | −2 | 0 | −2 |
| PKCbeta 2 | 4 | −2 | 11 | 26 |
| PKCgamma | 7 | 3 | 8 | 10 |
| Ret | 14 | 10 | 99 | 86 |
| ROCK2 | 39 | −8 | 88 | 32 |
| RSK2 | 17 | 1 | 48 | 22 |
| Src | −10 | 13 | 26 | 51 |
| Syk | — | −1 | — | — |
| TRKA | 54 | 93 | 100 | 101 |

Table 4 above shows the percent inhibition values obtained for Compounds 40, 2, 6 and 35 at 10 μM concentration. From this inhibition data it is apparent that certain kinases, e.g. Abl, CSK, FLT-3, Lck, Lyn, Ret and TRKA kinase are inhibited by compounds described herein. These activities may impart additional therapeutic benefit to these compounds.

Example I

Cancer Cell Line Data

Breast cancer cells (MCF-7, MDA-MB-468 and HCC1954), colon cancer cells (SW620) and lung cancer cells (A549), together with human mammary epithelial primary cells (HMEC) were seeded (1000 to 4000 per 80 μl per well depending on the cell growth rate) into 96-well plates 24 hours before compound overlay. Compounds were prepared as 10 mM stock solutions in 100% DMSO which were diluted with DMEM (Dulbecco's Modified Eagle's Medium) cell growth Medium (Invitrogen, Canada) containing 10% FBS (Fetal Bovine Serum) to concentrations ranging from 50 nM to 250 μM. Aliquots (20 μl) from each concentration were overlaid to 80 μl of the pre-seeded cells in the 96-plates to make final concentrations of 10 nM to 50 μM. The cells were cultured for 5 days before the Sulforhodamine B (SRB) assay was performed to determine the compound's cell growth inhibition activity.

Sulforhodamine B (Sigma, Canada) is a water-soluble dye that binds to the basic amino acids of cellular proteins. Thus, colorimetric measurement of the bound dye provides an estimate of the total protein mass that is related to the cell number. The cells are fixed in situ by gently aspirating off the culture media and adding 50 μl ice cold 10% Trichloroacetic Acid (TCA) per well and incubated at 4° C. for 30-60 min. The plates are washed with water five times and allowed to air dry for 5 min. Addition of 50 μl 0.4% (w/v) SRB solution in 1% (v/v) acetic acid to each well and incubatation for 30 mM at RT completes the staining reaction. Following staining, plates are washed four times with 1% acetic acid to remove unbound dye and then allowed to air dry for 5 min. The stain is solubilized with 100 μl of 10 mM Tris pH 10.5 per well. Absorbance is read at 570 nm.

The percentage (%) of relative growth inhibition was calculated by comparing to DMSO-treated only cells (100%). $GI_{50}$'s were determined for compounds with cytotoxic activity. The $GI_{50}$ was calculated using GraphPad PRISM software (GraphPad Software, Inc., USA). $GI_{50}$ (growth inhibition) is the compound concentration that causes 50% inhibition of cell growth.

In Table 5 below, $GI_{50}$ value ranges for several compound examples against a luminal breast cancer cell line (MCF-7), two basal breast cancer cell lines (MDA-MB-468 and HCC1954), a lung cancer cell line (A549), a colon cancer cell line (SW620) and primary breast cells (HMEC) are given. The example compounds demonstrated varying growth inhibition/cell killing activity against cancer cells of luminal breast cancer and basal breast cancer, lung cancer and colon cancer. In general, these compounds showed less activity against normal cells as exemplified by HMEC. The $GI_{50}$ ranges are indicated as "A," "B," "C," and "D," for values less than or equal to 5 μM; those greater than 5 μM and less than or equal to 20 μM; those greater than 20 μM and less than or equal to 50 μM; and those greater than 50 μM, respectively.

TABLE 5

Cell Growth Inhibition Data

| | Cell Line $GI_{50}$ Range | | | | | |
|---|---|---|---|---|---|---|
| Cpd # | MCF-7 | MDA-MB-468 | HCC1954 | SW620 | A549 | HMEC |
| 9 | A | A | C | B | B | D |
| 31 | A | A | A | A | A | C |
| 10 | A | A | B | A | B | D |
| 32 | A | A | A | A | A | A |
| 33 | A | A | D | A | A | D |
| 2 | A | A | A | A | A | C |
| 6 | A | A | A | A | A | B |
| 35 | A | A | A | A | A | B |
| 39 | A | A | A | A | A | B |

Additional data has been collected for further compounds and may be found, for example, in Examples of WO 09/079,767, published Jul. 2, 2009 and WO 10/115,279, published Oct. 14, 2010.

In addition to the cell lines tested as described above, selected compounds have been assayed against an extended panel. These include: breast cancer cell lines (T-47D, MDA-MB-231, Hs578T, 8T-474, SKBr-3 and HCC1954), a lung cancer cell line (H358), brain cancer cell lines (A172, Hs683 and SK-N-SH), colon cancer cell lines (Colo 205, HCT-15, HCT116 p53$^{+/+}$ and HCT116 p53$^{-/-}$), ovarian cancer cell lines (OVCAR-3, SK-OV-3 and SW626), a melanoma cell line (518A2), a prostate cancer cell line (PC-3) and an immortalized breast cell line (184A1). The SRB assay described above was used to assay test compounds against the extended panel (Table 6). The GI$_{50}$ ranges are indicated as "A," "B," "C," and "D," for values less than or equal to 5 µM; those greater than 5 µM and less than or equal to 20 µM; those greater than 20 µM and less than or equal to 50 µM; and those greater than 50 µM, respectively.

TABLE 6

Cell Growth Inhibition Data

| Cell line | Cpd. # GI$_{50}$ Range | | | | |
|---|---|---|---|---|---|
| | 9 | 31 | 33 | 32 | 3 |
| T-47D | A | A | A | A | A |
| MDA-MB-231 | B | A | A | A | A |
| Hs578T | B | A | A | A | A |
| BT-474 | D | A | B | A | A |
| SKBr-3 | A | A | D | A | A |
| HCC1954 | A | A | D | A | A |
| H358 | A | — | A | A | A |
| A172 | A | — | A | A | A |
| Hs683 | A | — | A | A | A |
| SK-N-SH | A | — | A | A | A |
| Colo 205 | A | A | A | A | A |
| HCT-15 | A | — | A | A | A |
| HCT116 p53$^{-/-}$ | D | A | A | A | A |
| HCT116 p53$^{+/+}$ | D | A | A | A | A |
| OVCAR-3 | D | — | A | A | A |
| SK-OV-3 | D | — | B | A | A |
| SW626 | D | — | B | A | A |
| 518A2 | A | — | A | A | A |
| PC-3 | C | — | A | A | A |
| 184A1 | C | A | A | A | A |

Some compounds described herein, although inhibiting the isolated PLK4 enzyme activity, generally failed to inhibit the growth of breast cancer cell lines (e.g., compounds 25, 27, 30 and 34 exhibited GI$_{50}$ values >50 µM on the MCF-7, MDA-MB-468 and T-47D lines).

Example J

Identification of Predictors of Response to PLK4 Inhibitors

To identify predictors of response to PLK4 inhibitors, cell viability GI$_{50}$ data was generated for 20 PLK4 compounds (biochemical PLK4 IC$_{50}$'s ranging from subnanomolar to <15 µM) on more than 33 unique breast cancer and normal cell lines (FIG. 1A). The GI$_{50}$ values for 5 PLK4 inhibitors (FIG. 1B) were log-transformed and the distance matrix in log-space between these data points was calculated. Metric scaling was then performed on the lower triangular of the distance matrix. Metric scaling is a transformation that retains the relative distance of the original data points, thus FIG. 2 is a reasonable graphical representation of the dissimilarity of different cell lines with regard to their behaviour towards these PLK4 inhibitors. Although FIG. 2 clearly indicates visually which groups of cell lines behave similarly, formal clustering was also performed using the complete linkage method. Data points belonging to the three most populous clusters are encircled with a dotted line.

Figure 3A:
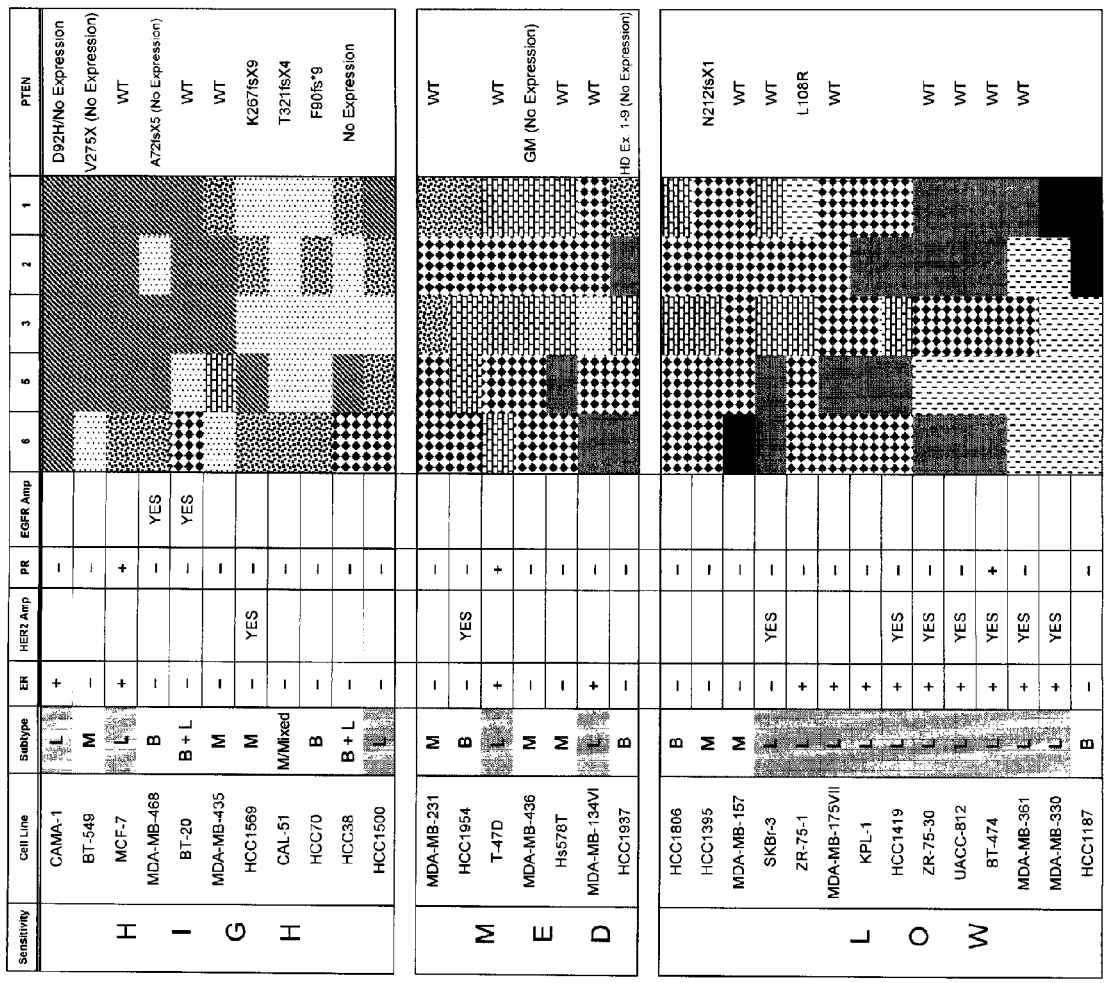
FIG. 3A is a schematic chart illustrating the molecular characteristics of the breast cancer cell lines in each cluster of high, medium and low sensitivity to PLK4 inhibitors. Subtypes are listed as either luminal (L), basal (B), or mesenchymal (M). Expression for estrogen receptor (ER), and progesterone receptor (PR) were scored for each cell line as either positive (+) or negative (−) (Neve et al., Cancer Cell 10: 515-527, 2006). The presence of amplified epidermal growth factor receptor (EGFR) expression (EGFR Amp) and/or amplified human epidermal growth factor receptor-2 (HER2 Amp) are also reported. Mutation status of the gene sequence for PTEN was also investigated, and the specific mutation or wild-type (WT) sequence is listed. The cell viability $GI_{50}$s of 5 PLK4 inhibitors (compounds 1-3, 5 and 6) are represented by color intensity (see key legend). The cell lines were clustered according to their sensitivity to PLK4 inhibitor treatment (high, medium, or low sensitivity to PLK4 inhibitor, as measured by cell viability). Predictors of high sensitivity and predictors of low sensitivity to PLK inhibitors are summarized.
Figure 3B:
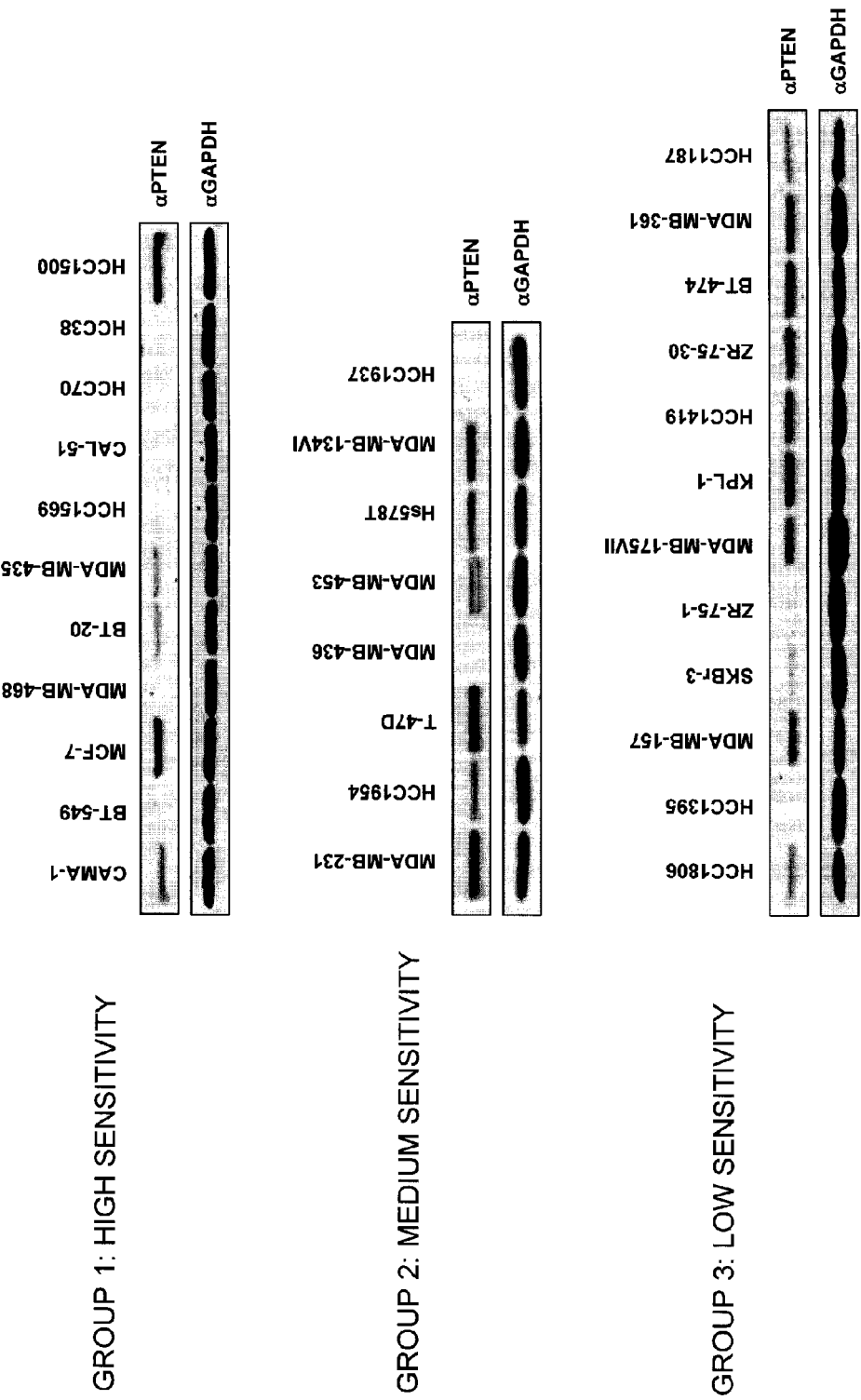
FIG. 3B is comprised of Western immunoblots showing levels of PTEN in each cluster of high, medium and low sensitivity to PLK4 inhibitors. GAPDH levels are included as loading controls.

A schematic chart was constructed that illustrates the molecular characteristics of the breast cancer cell lines in each cluster of high, medium and low sensitivity to the 5 PLK4 inhibitors (FIG. 3A). Predictors of high sensitivity to PLK4 inhibitors were identified as non-luminal, triple-negative subtype with a PTEN deficiency or PIK3CA mutation, and predictors of low sensitivity to PLK inhibitors were identified as luminal, HER2+/ER+ subtype. Western immunoblots of levels of PTEN in each cluster of high (group 1), medium (group 2) and low (group 3) sensitivity to PLK4 inhibitors demonstrated reduced PTEN expression in the high sensitivity group (FIG. 3B).

Example K

Figure 4A:
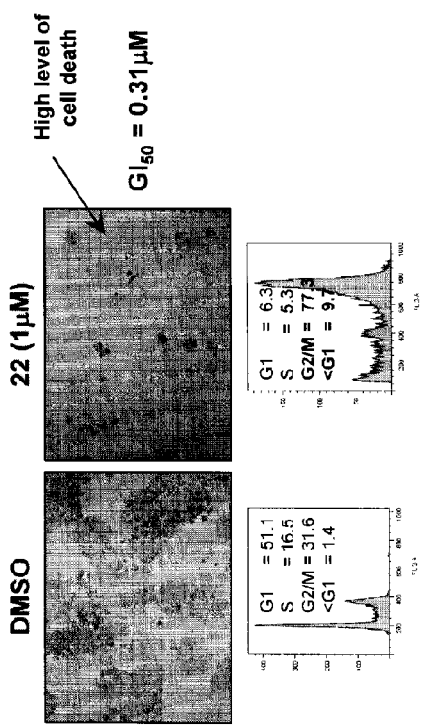
FIGS. 4A and 4B illustrate the comparison of cell viability $GI_{50}$ and cell cycle data for two breast cancer cell lines, MDA-MB-468 (PTEN negative cells) and MDA-MBA-231 (PTEN wild-type cells), treated with PLK4 inhibitor 22. The graphs represent the cell growth calculated using the sulforhodamine B (SRB) assay. The cells were incubated in the presence of DMSO (control), 1 μM or 5 μM of PLK4 inhibitor. Representative photographs of the cells are provided 5 days after PLK4 inhibitor addition. MDA-MB-468 cells in the presence of PLK4 inhibitor 22 exhibited a high level of cell death. FACS analysis was also performed, and the percentage of cells in each cell cycle phase G1, S, G2/M and <G1 (sub-G1, which represents dead and dying cells) is presented for the conditions indicated. Cell death was dependent on the PTEN status of the cells.
Figure 4B:
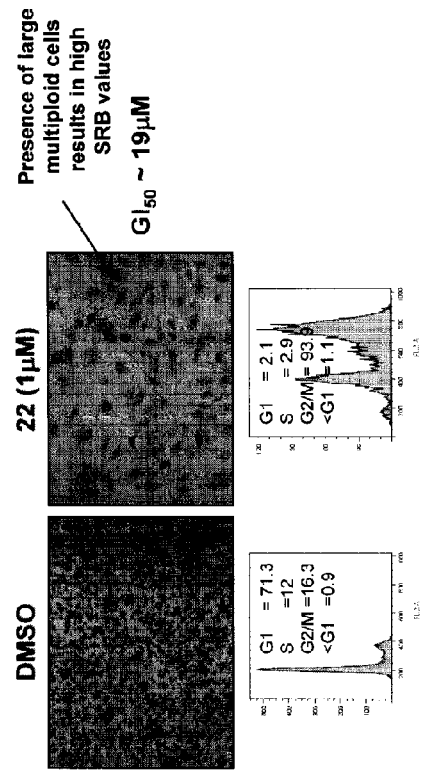

Comparison of Cell Growth Inhibition (GI$_{50}$) and Cell Cycle Data for a PLK4 Inhibitor in PTEN Wild-type and Negative Breast Cancer Cells Cell viability GI$_{50}$ and cell cycle data for PLK4 inhibitor 22 were compared for two breast cancer cell lines, PTEN wild-type MDA-MB-231 cells and MDA-MB-468 cells, which do not express PTEN. Treatment of MDA-MB-468 (FIG. 4A) and MDA-MB-231 (FIG. 4B) cells with 22 for 5 days yielded GI$_{50}$ values of 0.31 µM and ~19 µM, respectively, as determined by SRB assay. To investigate this difference in sensitivity of the cancer cells to the PLK4 inhibitor, cell cycle analysis was performed 48 hours after treatment, and the percentage of cells with sub-G1 DNA content, which represents dead and dying and cells, was measured. In response to 22 treatment, both cell lines exhibited increased 4N DNA content and the generation of 8N DNA polyploid cells, but only MDA-MB-468 cells displayed a significant increase in sub-G1 percentage. A 9.7% sub-G1 percentage was observed for MDA-MB-468 cells treated with an inhibitor concentration of 1 µM compared to 1.4% for the DMSO control (FIG. 4A). In MDA-MB-231 cells, however, only 1.1% of cells had a sub-G1 DNA content, and was not statistically different from that in the DMSO control (FIG. 4B). Representative photographs of the cells 5 days after treatment confirmed that MDA-MB-468 cells in the presence of 22 exhibited a high level of cell death, while MDA-MB-231 cells were polyploid. The formation of 8N DNA polyploid MDA-MB-231 cells after PLK4 inhibitor addition resulted in high SRB readings, and thus high GI$_{50}$ values. Collectively, these data suggest that cell death was dependent on the PTEN status of the cells.

Example L

PLK4 Inhibitors Cause Increased Death in PTEN Negative Breast Cancer Cells

Figure 5A:
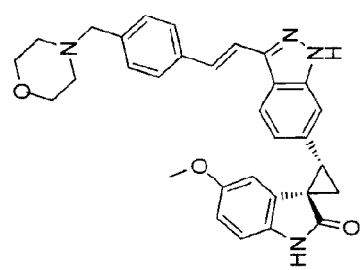
Figure 5A:

To explore if PTEN status may be correlated with a differential response of cancer cells to PLK4 inhibitor treatment, MDA-MB-231 (PTEN wild-type) cells were compared with MDA-MB-468 (PTEN negative) cells. Treatment of MDA-MB-468 cells for 24 hours with increasing concentrations of PLK4 inhibitor 21 resulted in a robust induction of the early cell death marker cleaved PARP (cPARP) at concentrations of 0.03 µM and above. The increase in cPARP levels was detectable as early as 15 hours after inhibitor treatment at this concentration. In contrast, MDA-MB-231 cells exhibited no changes in cPARP above background levels when treated for 24 hours with inhibitor at concentrations as high as 1 µM (FIG. 5A). In addition, immunofluorescence staining analysis showed that cPARP was present in the nuclei of MDA-MB-468 cells treated with 0.1 µM 21 for 72 hours, but no cPARP was detectable in MDA-MB-231 cells under the same conditions (FIG. 5B).

Consistent with these data, a cell cycle analysis was performed on treated cells and the percentage of cells with sub-G1 DNA content was measured. In response to compound treatment, both cell lines exhibited increased 4N DNA content and the generation of 8N DNA polyploid cells, but only MDA-MB-468 cells displayed a significant increase in sub-G1 percentage. An 11.8% sub-G1 percentage was observed for MDA-MB-468 cells treated with inhibitor concentrations of 0.01 μM and 0.1 μM compared to 2.3% for the DMSO control. In MDA-MB-231 cells, however, only 0.8% of cells had a sub-G1 DNA content, the same number as the DMSO control (FIG. 5C). Overall, these data suggest that PLK4 compounds elicit a cell death response marked by increases in the early apoptotic marker cPARP and an increase in the percentage of sub-G1 cells in PTEN negative MDA-MB-468 cells, but not in PTEN wild-type MDA-MB-231 cells.

Example M

Figure 6A:
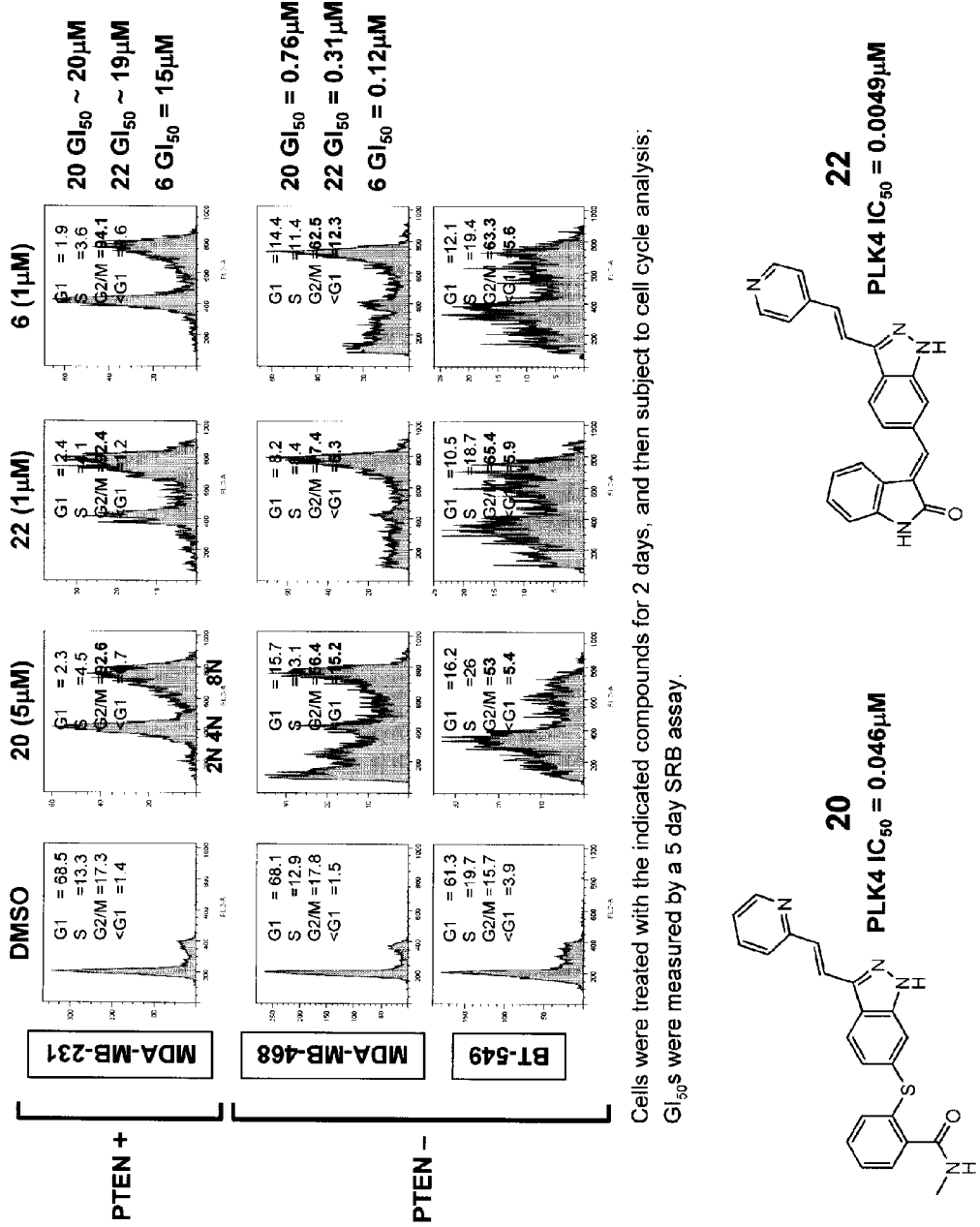
FIGS. 6A and 6B are a series of FACS analyses of cell cycle profiles of PTEN wild-type (Hs578T and MDA-MB-231) and PTEN negative (BT-549, CAMA-1 and MDA-MB-468) breast cancer cell lines treated with various PLK4 inhibitors (compounds 6, 20-23). Cell cycle analyses were performed 2 days (FIG. 6A) or 5 days (FIG. 6B) after PLK4 inhibitor treatment. Cell death is dependent on the PTEN status of the cells (compare <G1 values for PTEN wild-type cells with <G1 values for PTEN negative cells). The chemical structures of PLK4 inhibitor 20, 22 and 23 are illustrated.
Figure 6B:
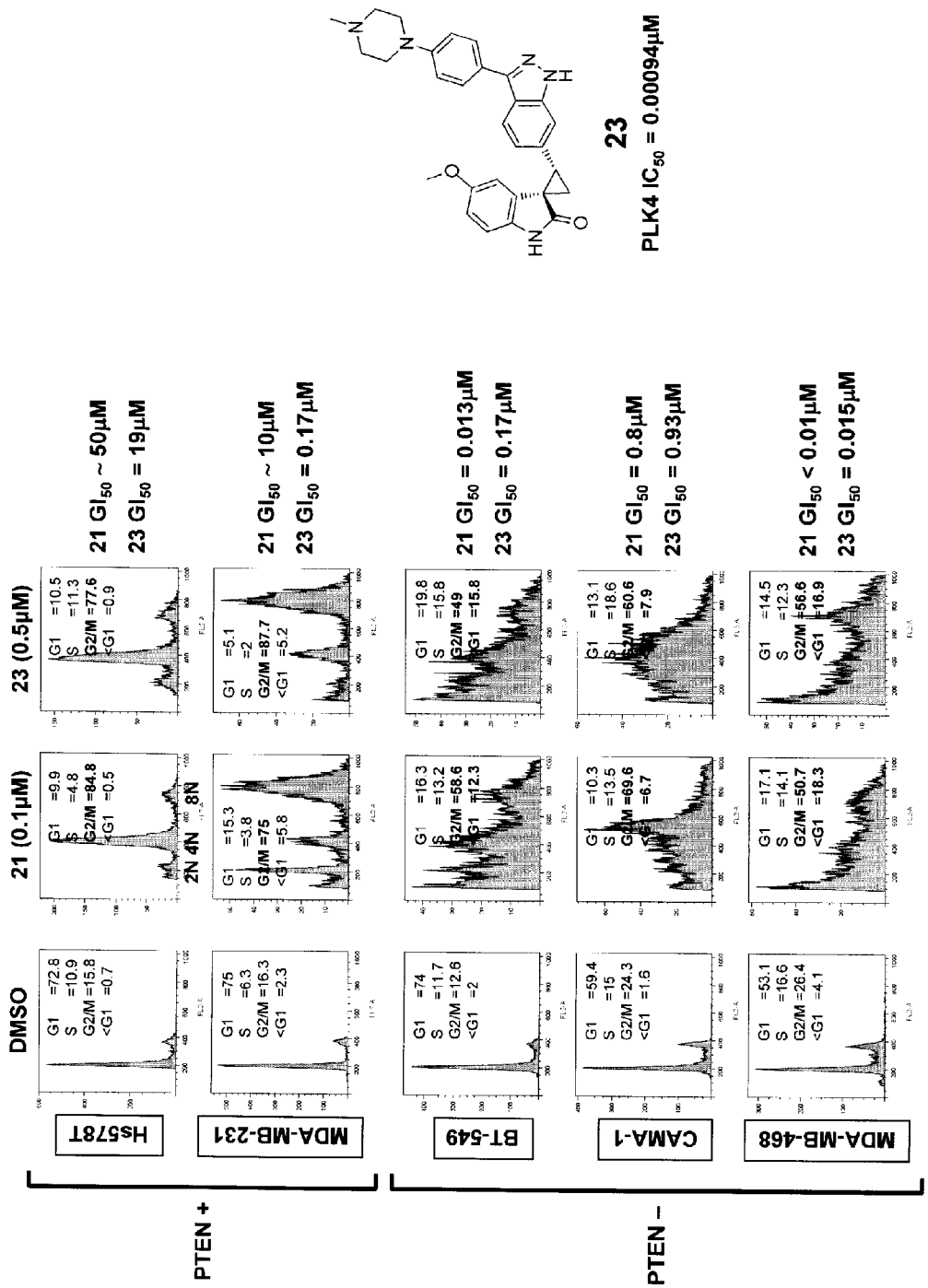

Comparison of Cell Cycle Data for PLK4 Inhibitors in PTEN Wild-Type and PTEN Negative Breast Cancer Cells To further investigate if PTEN status may be correlated with a differential response of cancer cells to PLK4 inhibitor treatment, PTEN wild-type breast cancer cells were compared with breast cancer cells, which do not express PTEN. Cell cycle analysis was performed on inhibitor treated cells and the percentage of cells with sub-G1 DNA content, which represents dying and dead cells, was measured (FIGS. 6A and 6B). In response to PLK4 inhibitor treatment (compounds 6, and 20-23), both PTEN wild-type (Hs578T and MDA-MB-231) and PTEN negative (BT-549, CAMA-1 and MDA-MB-468) cell lines exhibited increased 4N DNA content and the generation of 8N DNA polyploid cells, but only PTEN negative cells displayed a significant increase in sub-G1 percentage. Overall, these data suggest that PLK4 compounds elicit a cell death response marked by an increase in the percentage of sub-G1 cells in PTEN negative cells, but not in PTEN wild-type cancer cells.

Example N

Figure 7:
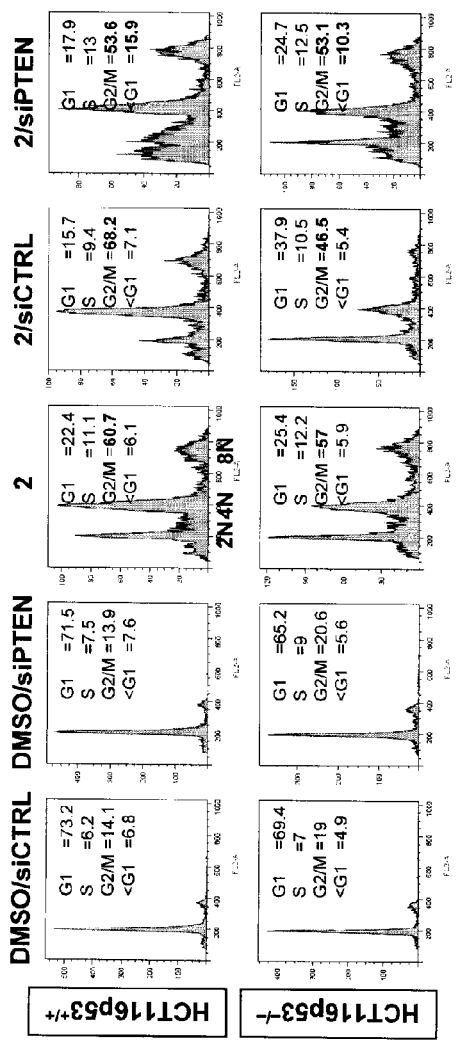
FIG. 7 illustrates that PTEN knockdown sensitizes PLK4 inhibitor-treated HCT116 colon cancer cells to cell death. Cell cycle analysis was performed on cells (either p53 wild-type or negative) transfected with either control siRNA (siCTRL) or siRNA targeting PTEN (siPTEN), and treated two days after transfection with either DMSO or 0.5 μM PLK4 inhibitor 2 for two days. The percentages of <G1 cells, indicative of cell death, are shown.
Figure 7:
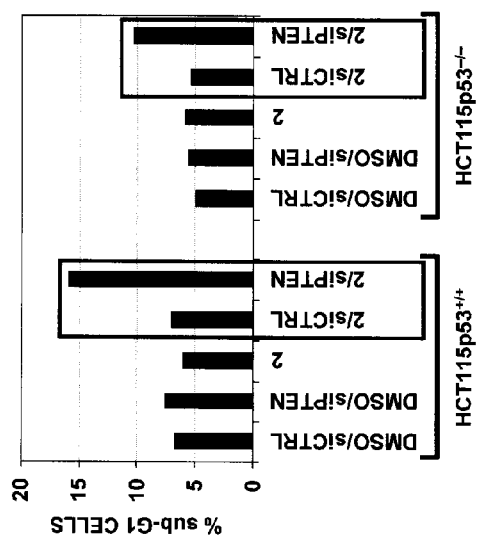

PTEN Depletion Causes Increased Death in PLK4 Inhibitor-Treated Colon Cancer Cells To explore if PTEN status may be a contributing factor in determining if PLK4 inhibitor treatment induces a cell death response in cancer cells, a test of whether reducing the levels of endogenous PTEN would sensitize HCT116 cells (either p53 wild-type or negative) to PLK4 compound-induced death (FIG. 7) was performed. HCT116 cells were transfected with siRNAs targeting the PTEN transcript or a control siRNA of arbitrary sequence 48 hours prior to treatment with PLK4 inhibitor 2. Levels of endogenous PTEN were substantially decreased in PTEN siRNA-transfected cells relative to the control siRNA (data not shown). After two days of inhibitor treatment, the percentage of sub-G1 cells was measured by cell cycle analysis. Reducing PTEN levels increased the percentage of sub-G1 cells from 7.1% in the control siRNA sample to 15.9% in the PTEN siRNA-transfected HCT116 p53 wild-type cells, and from 5.4% in the control siRNA sample compared to 10.3% in the PTEN siRNA-transfected HCT116 p53 negative cells. Similar results were obtained from three independent experiments.

Example O

Figure 8A:
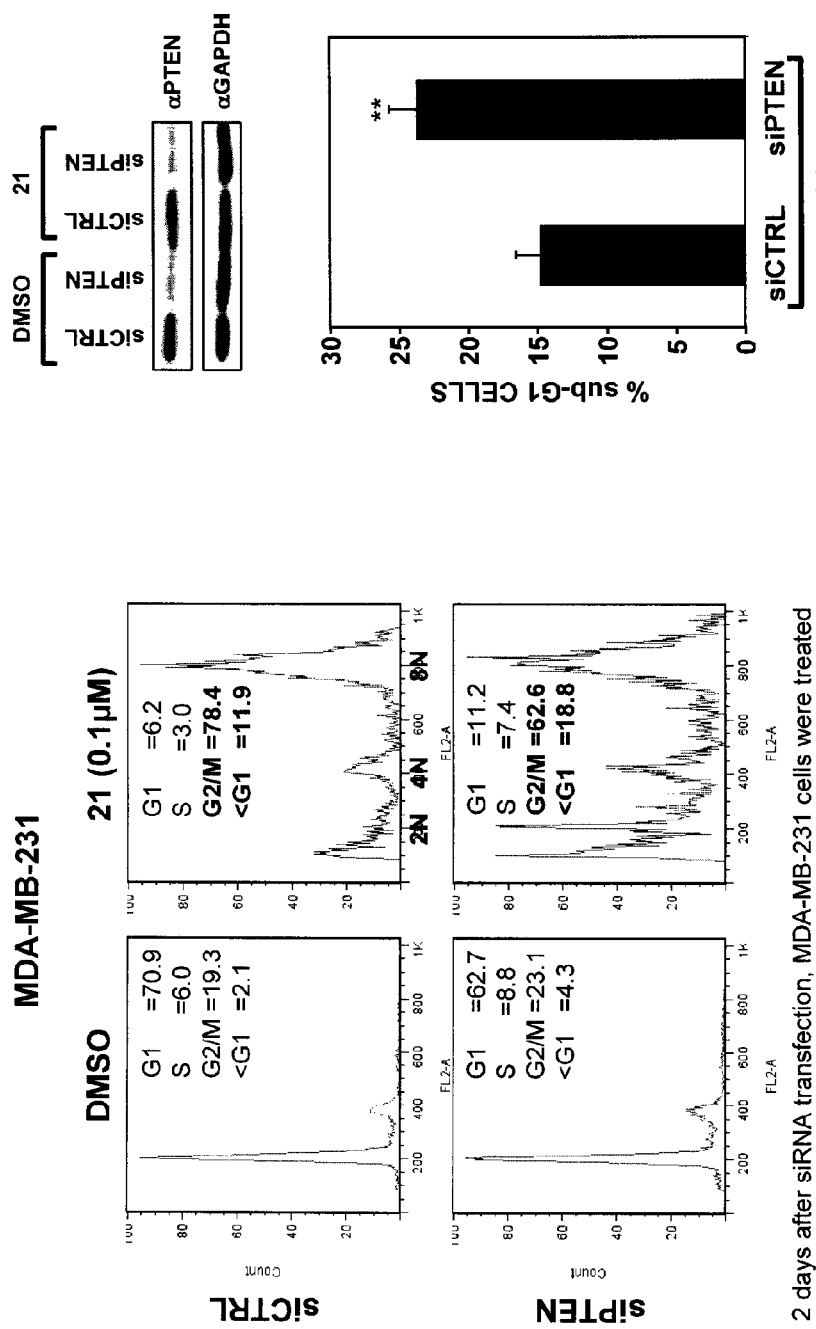
FIGS. 8A and 8B show how reduction of PTEN levels in MDA-MB-231 breast cancer cells increases PLK4 inhibitor-induced cell death.

PTEN Depletion Causes Increased Death in PLK4 Inhibitor-Treated Breast Cancer Cells To further investigate PTEN status as a contributing factor in determining if PLK4 inhibitor treatment induces a cell death response in cancer cells, we evaluated whether reducing the levels of endogenous PTEN would sensitize MDA-MB-231 cells to PLK4 compound-induced apoptosis. MDA-MB-231 cells were transfected with siRNAs targeting the PTEN transcript or a control siRNA of arbitrary sequence 48 hours prior to treatment with PLK4 inhibitor 21. Levels of endogenous PTEN were substantially decreased in PTEN siRNA-transfected cells relative to the control siRNA. After six days of treatment, the percentage of sub-G1 cells was measured by cell cycle analysis. Reducing PTEN levels increased the percentage of sub-G1 cells from 11.9% in the control siRNA sample compared to 18.8% for PTEN siRNA-transfected cells. The results from three independent experiments indicated the difference in sub-G1 percentage of 14.9% for the control and 23.6% when PTEN levels were reduced was statistically significant ($P<0.01$, Student's T-Test) (FIG. 8A).

Figure 8B:
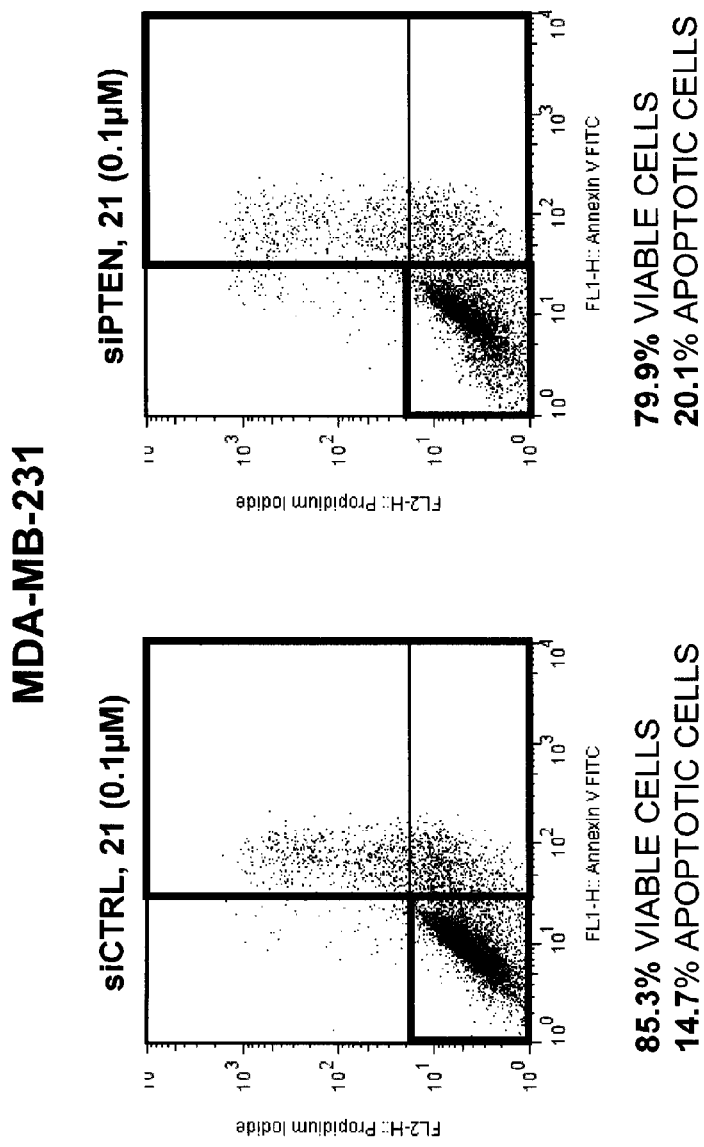

In order to verify that the increase in sub-G1 percentage after PLK4 compound treatment in PTEN reduced cells was a result of increased cell death, levels of apoptosis were specifically measured with the Annexin V/Propidium Iodide assay. Two days following siRNA transfection, MDA-MB-231 cells were treated with PLK4 inhibitor 21 for 4 days, stained with AnnexinV-FITC and Propidium Iodide and subject to analysis by flow cytometry. After compound treatment, the percentage of Annexin V-positive cells, which comprise the cell population undergoing apoptotic cell death, was 20.1% when PTEN levels were knocked down compared to 14.7% for the control (FIG. 8B). Taken together, these data demonstrate that PTEN plays a role in determining whether cancer cells undergo apoptotic cell death as a result of PLK4 inhibitor treatment.

The teachings of all patents, published applications and references cited herein are incorporated by reference in their entirety. In particular, the teachings of PCT/CA2008/002227, titled "Indazolyl, Benzimidazolyl, Benzotriazolyl Substituted Indolinone Derivatives As Kinase Inhibitors Useful In The Treatment Of Cancer", filed on Dec. 19, 2008, are incorporated by reference in their entirety; and U.S. Provisional Application No. 61/211,988, titled "Kinase Inhibitors And Method Of Treating Cancer With Same", filed on Apr. 6, 2009, are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a patient with cancer, the method comprising:
    (a) providing a suitable sample from a cancer patient; and
    (b) determining PTEN gene expression in said sample;
    (c) treating the patient with an effective amount of a PLK-4 antagonist if the patient has a PTEN mutation; and excluding the patient from a PLK-4 antagonist therapy if the patient does not have a PTEN mutation;
    wherein the PTEN gene mutation results in reduced expression of PTEN as compared to a normal control, expression of a non-functional or limited functioning PTEN protein, or a loss of PTEN expression.

2. The method of claim 1, wherein the cancer is breast cancer, prostate cancer, endometrial cancer, ovarian cancer, brain cancer, skin cancer, thyroid cancer, lung cancer, bladder cancer, colon cancer, melanoma, glioblastoma or lymphoma.

3. The method of claim 2, wherein the cancer is a basal subtype breast cancer.

4. The method of claim 2, wherein the breast cancer is estrogen receptor (ER) negative, human epidermal growth factor receptor-2 (HER2) negative, progesterone receptor (PR) negative, or a combination thereof.

5. The method of claim 2, wherein the cancer is colon cancer.

6. The method of claim 1, further comprising treating the patient without the PTEN mutation with an anti-cancer therapy other than the PLK-4 antagonist.

7. The method of claim 1, wherein the PLK-4 antagonist is represented by structural formula (I):

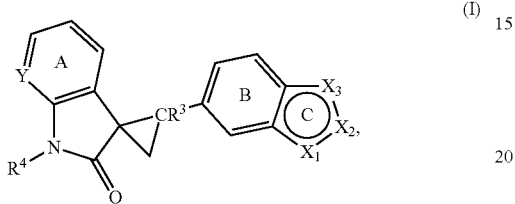

(I)

or a pharmaceutically acceptable salt thereof, wherein:

ring A is optionally and independently substituted with one or more substituents represented by $R^a$ and ring B is optionally and independently substituted with one or more substituents represented by $R^b$;

ring C is a 5-membered heteroaromatic ring wherein one of $X_1$-$X_3$ is N, one of $X_1$-$X_3$ is $NR^5$, and one of $X_1$-$X_3$ is N or $CR^6$;

Y is independently N, CH or $CR^a$;

each of $R^a$ and $R^b$ independently is:

halogen, —C(O)$OR^1$, —C(O)$R^1$, —C(S)$R^1$, —OC(O)$R^1$—, —C(O)$NR^1R^2$, —C(S)$NR^1R^2$, —OC(O)$NR^1R^2$, —S(O)$R^1$, —S(O)$_2R^1$, —SO$_3R^1$, —SO$_2NR^1R^2$, —$OR^1$, —$SR^1$, —$NR^1R^2$, —$NR^2$C(O)$R^1$, —$NR^2$S(O)$R^1$, —$NR^2$C(O)$OR^1$, —$NR^2$C(O)ON$R^1R^2$, —N($R^2$)C(O)N$R^1R^2$, —$NR^2$SO$_2NR^1R^2$, —$NR^2$SO$_2R^1$; —NO$_2$, —CN, —NCS; or two ortho $R^a$ groups taken together form —O—[CH$_2$]$_p$—O—, —S—[CH$_2$]$_p$—S— or —[CH$_2$]$_q$—; or $C_{1-10}$ aliphatic group optionally substituted with one or more substituents selected from the group consisting halogen, nitro, cyano, —N($R^{21}$)$_2$, —C(O)N($R^{21}$)$_2$, —C(O)N($R^{21}$)$_2$, —$NR^{21}$C(O)$R^{21}$, —SO$_2R^{22}$, —SO$_2N(R^{21})_2$, —$NR^{21}$SO$_2R^{22}$, —$NR^{21}$C(O)O$R^{21}$, —OC(O)N($R^{21}$)$_2$, —$NR^{21}$C(O)N($R^{21}$)$_2$, —NRC(O)ON(R)$_2$, —$NR^{21}$SO$_2N(R^{21})_2$, —$OR^{21}$, —$SR^{21}$, $C_{1-10}$ haloalkoxy, —C(O)$R^{21}$, —C(O)O$R^{21}$ and —OC(O)$R^{21}$; or ($C_{0-10}$ alkylene)-$Ar^1$, ($C_{2-10}$ alkenylene)-$Ar^1$, wherein $Ar^1$ is a $C_{6-14}$ aryl group or a 5-14 membered heteroaryl group, each optionally and independently substituted with one or more substituents selected from the group consisting of halogen, nitro, cyano, $C_{1-10}$ alkyl, $C_{1-10}$ haloalkyl, ($C_{1-10}$ haloalkoxy)$C_{1-10}$ alkyl, ($C_{1-10}$ alkoxy)$C_{1-10}$ alkyl, $C_{1-10}$ hydroxyalkyl, $C_{1-10}$ aminoalkyl, ($C_{1-10}$ alkylamino)$C_{1-10}$ alkyl, ($C_{1-10}$ dialkylamino)$C_{1-10}$ alkyl, —N($R^{21}$)$_2$, —C(O)N($R^{21}$)$_2$, —C(O)N($R^{21}$)$_2$, —$NR^{21}$C(O)$R^{21}$, —SO$_2R^{22}$, —SO$_2N(R^{21})_2$, —$NR^{21}$SO$_2R^{22}$, —$NR^{21}$C(O)N($R^{21}$)$_2$, —NRC(O)ON(R)$_2$, —$NR^{21}$SO$_2N(R^{21})_2$, —$OR^{21}$, —$SR^{21}$, $C_{1-10}$ haloalkoxy, —C(O)$R^{21}$, —C(O)O$R^{21}$, —OC(O)$R^{21}$, phenyl and 5-6 membered heteroaryl, wherein said phenyl and said 5-6 membered heteroaryl are each independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^1$ independently is:
i) hydrogen;
ii) a $C_{6-14}$ aryl group or a 5-14 membered heteroaryl group, each optionally and independently substituted with one or more substituents selected from the group consisting of halogen, —NO$_2$, —CN, —NCS, $C_1$-$C_{10}$ aliphatic, ($C_{1-10}$ alkylene)-$Ar^{10}$, ($C_{2-10}$ alkenylene)-$Ar^{10}$, —C(O)O$R^{10}$, —C(O)$R^{10}$, —C(S)$R^{10}$, —OC(O)$R^{10}$, —C(O)N($R^{11}$)$_2$, —C(S)N($R^{11}$)$_2$, —OC(O)N($R^{11}$)$_2$, —S(O)$R^{12}$, —S(O)$_2R^{12}$, —SO$_3R^{12}$, —SO$_2N(R^{11})_2$, —$OR^{10}$, —$SR^{10}$, —N($R^{11}$)$_2$, —$NR^{11}$C(O)$R^{10}$, —$NR^{11}$S(O)$R^{12}$, —$NR^{11}$C(O)O$R^{12}$, —N($R^{11}$)C(O)N($R^{11}$)$_2$, —$NR^{11}$SO$_2N(R^{11})_2$ and —$NR^{11}$SO$_2R^{12}$; or
iii) a $C_{1-10}$ aliphatic group optionally substituted with one or more substituents selected from the group consisting of halogen, —NO$_2$, —CN, —NCS, $Ar^{10}$, —C(O)O$R^{10}$, —C(O)$R^{10}$, —C(S)$R^{10}$, —OC(O)$R^{10}$, —C(O)N($R^{11}$)$_2$, —C(S)N($R^{11}$)$_2$, —OC(O)N($R^{11}$)$_2$, —S(O)$R^{12}$, —S(O)$_2R^{12}$, —SO$_3R^{12}$, SO$_2N(R^{11})_2$, —$OR^{10}$, —$SR^{10}$, —N($R^{11}$)$_2$, —$NR^{11}$C(O)$R^{10}$, —$NR^{11}$S(O)$R^{12}$, —$NR^{11}$C(O)O$R^{12}$, —N($R^{11}$)C(O)N($R^{11}$)$_2$, —$NR^{11}$SO$_2N(R^{11})_2$ and —$NR^{11}$SO$_2R^{12}$, provided that $R^1$ is other than hydrogen when $R^a$ or $R^b$ is —S(O)$R^1$, —S(O)$_2R^1$, —SO$_3R^1$, —$NR^2$S(O)$R^1$ or —$NR^2$SO$_2R^1$; and each $R^2$ independently is —H or $C_1$-$C_6$ alkyl, or, taken together with $NR^1$, forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, ($C_{1-6}$ alkylamino)$C_{1-6}$ alkyl, ($C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl;

$R^3$ is —H, halogen, $C_{1-6}$ alkyl or $C_{1-6}$ haloalkyl;

each of $R^4$ and $R^5$ independently is —H, $C_{1-6}$ alkyl, phenyl, —C(O)($C_{1-6}$ alkyl), —C(O)(phenyl), —C(O)O($C_{1-6}$ alkyl), —C(O)O(phenyl), —S(O)$_2$($C_{1-6}$ alkyl) or —S(O)$_2$(phenyl), wherein each alkyl in the groups represented by $R^4$ and $R^5$ independently is optionally substituted with one or more substituents selected from the group consisting of halogen, hydroxy, nitro, cyano, amino, phenyl, 5-6 membered heteroaryl, $C_{1-6}$ alkoxy and $C_{1-6}$ haloalkoxy, and wherein each phenyl in the groups represented by $R^4$ and $R^5$ independently is optionally substituted with one or more substituents selected from the group consisting of halogen, hydroxy, nitro, cyano, amino, $C_{1-6}$ alkyl, $C_{1-6}$ haloalkyl, $C_{1-6}$ alkoxy and $C_{1-6}$ haloalkoxy;

$R^6$ is hydrogen, halogen, nitro, cyano, R', —OR, —SR, —N(R)$_2$, —C(O)R, —C(O)OR, —OC(O)R, —C(O)N(R)$_2$, —OC(O)N(R)$_2$, —NRC(O)R, —NRC(O)OR, —SOW, —SO$_2$R', —SO$_3$R', —SO$_2$N(R)$_2$, —NRS(O)R', —NRSO$_2$R', —NRC(O)N(R)$_2$, —NRC(O)ON(R)$_2$, or —NRSO$_2$N(R)$_2$;

each $R^{10}$ independently is:
i) hydrogen;
ii) a $C_{6-14}$ aryl group or a 5-14 membered heteroaryl group, each optionally and independently substituted with one or more substituents selected from the group consisting of halogen, nitro, cyano, hydroxy, $C_{1-10}$ alkyl, $C_{1-10}$ haloalkyl, $(C_{1-10}$ haloalkoxy)$C_{1-10}$ alkyl, $(C_{1-10}$ alkoxy)$C_{1-10}$ alkyl, $C_{1-10}$ hydroxyalkyl, $C_{1-10}$ aminoalkyl, $(C_{1-10}$ alkylamino)$C_{1-10}$ alkyl, $(C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ alkoxy, $C_{1-10}$ haloalkoxy, $C_{1-10}$ alkylcarbonyloxy, $C_{1-10}$ alkoxycarbonyl and $C_{1-10}$ alkylcarbonyl; or iii) a $C_{1-10}$ alkyl group optionally substituted with one or more substituents selected from the group consisting of halogen, nitro, cyano, hydroxy, $C_{1-10}$ haloalkyl, $C_{1-10}$ alkoxy, $C_{1-10}$ haloalkoxy, amino, $C_{1-10}$ alkylamino, $C_{1-10}$ dialkylamino, $C_{1-10}$ alkylcarbonyloxy, $C_{1-10}$ alkoxycarbonyl, $C_{1-10}$ alkylcarbonyl and phenyl, said phenyl being optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each $R^{11}$ independently is $R^{10}$, —$CO_2R^{10}$, —$SO_2R^{10}$ or —$C(O)R^{10}$, or —$N(R^{11})_2$ taken together is a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, $(C_{1-6}$ alkylamino)$C_{1-6}$ alkyl, $(C_{1-6}$ dialkylamino)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl and $C_{1-6}$ alkylcarbonyl; and each $R^{12}$ is independently is $R^{10}$ provided that $R^{12}$ is not hydrogen;

each $R^{21}$ independently is hydrogen, $C_{1-6}$ alkyl, phenyl or 5-6 membered heteroaryl, wherein each of the phenyl and heteroaryl groups represented by $R^{21}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{21}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy; or $N(R^{21})_2$ forms a non-aromatic heterocyclic group optionally substituted with one or more substituents selected from the group consisting of halogen, hydroxy, nitro, cyano, =O, $C_{1-3}$ alky, $C_{1-3}$ haloalkyl, $C_{1-3}$ alkoxy, $C_{1-3}$ haloalkoxy and amino; and each $R^{22}$ independently $C_{1-6}$ alkyl, phenyl or 5-6 membered heteroaryl, wherein each of the phenyl and heteroaryl groups represented by $R^{22}$ is independently and optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy, and wherein the alkyl group represented by $R^{22}$ is optionally substituted with one or more substituents selected from the group consisting of halogen, hydroxy, nitro, cyano, amino, $C_{1-3}$ alkyl, $C_{1-3}$ haloalkyl, $C_{1-3}$ alkoxy and $C_{1-3}$ haloalkoxy;

each R independently is hydrogen, $C_{1-10}$ aliphatic, phenyl or 5-6 membered heteroaryl, wherein the aliphatic group represented by R is optionally substituted with one or more substituents selected from the group consisting of halogen, hydroxy, nitro, cyano, amino, phenyl, 5-6 membered heteroaryl, $C_{1-6}$ alkoxy, $C_{1-6}$ haloalkoxy, and wherein each of the phenyl and heteroaryl groups represented by R, and the phenyl and heteroaryl substituents for the aliphatic group represented by R independently are optionally and independently substituted with one or more substituents selected from the group consisting of halogen, hydroxy, nitro, cyano, amino, $C_{1-6}$ alkyl, $C_{1-6}$ haloalkyl, $C_{1-6}$ alkoxy, $C_{1-6}$ haloalkoxy, or $N(R)_2$ forms a non-aromatic heterocyclic group optionally substituted with one or more substituents selected from the group consisting of =O, =S, halogen, nitro, cyano, hydroxy, $C_{1-6}$ alkyl, $C_{1-6}$ haloalkyl, $C_{1-6}$ hydroxyalkyl, amino, $C_{1-6}$ alkylamino, $C_{1-6}$ dialkylamino, $C_{1-6}$ aminoalkyl, $(C_{1-6}$ alkylamino)$C_{1-6}$ alkyl, $(C_{1-6}$ dialkylamino)$C_{1-6}$ alkyl, (phenyl)$C_{1-6}$ alkyl, (5-6 membered heteroaryl)$C_{1-6}$ alkyl, $C_{1-6}$ alkoxy, $C_{1-6}$ haloalkoxy, $C_{1-6}$ alkylcarbonyloxy, $C_{1-6}$ alkoxycarbonyl, $C_{1-6}$ alkylcarbonyl, phenyl and 5-6 membered heteroaryl; and each R' independently is $C_{1-10}$ aliphatic, phenyl or 5-12 membered heteroaryl, wherein the aliphatic group represented by R' is optionally substituted with one or more substituents selected from the group consisting of halogen, hydroxy, nitro, cyano, amino, phenyl, 5-12 membered heteroaryl, $C_1$-$C_6$ alkoxy, $C_1$-$C_6$ haloalkoxy, $C_{1-6}$ alkylamino, $C_{1-6}$ dialkylamino, —C(O)($C_1$-$C_6$ alkyl), —C(O)($C_1$-$C_6$ haloalkyl), —C(O)(phenyl), —C(O)(non-aromatic heterocyclic group), —C(O)O($C_1$-$C_6$ alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_1$-$C_6$ alkyl), —S(O)$_2$($C_1$-$C_6$ haloalkyl) and —S(O)$_2$(phenyl), and wherein each of the phenyl and heteroaryl groups represented by R', and the phenyl and heteroaryl groups in the substituents for the aliphatic group represented by R' independently are optionally substituted with one or more substituents selected from the group consisting of halogen, —OH, —SH, nitro, cyano, amino, $C_{1-6}$ alkylamino, $C_{1-6}$ dialkylamino, $C_1$-$C_6$ alkyl, $C_1$-$C_6$ haloalkyl, —O($C_{1-6}$ alkyl), —S($C_{1-6}$ alkyl), —O($C_{1-6}$ haloalkyl), ($C_{1-6}$ haloalkoxy)$C_{1-6}$ alkyl, $(C_{1-6}$ alkoxy)$C_{1-6}$ alkyl, $C_{1-6}$ hydroxyalkyl, $(C_{1-6}$ aminoalkyl), $(C_{1-6}$ alkylamino)$C_{1-6}$ alkyl, $(C_{1-6}$ dialkylamino)$C_{1-6}$ alkyl, (phenyl)$C_{0-6}$ alkyl, (5-6 membered heteroaryl)$C_{0-6}$ alkyl, (non-aromatic heterocyclic group)$C_{0-6}$ alkyl (optionally substituted with $C_{1-6}$ alkyl or $C_{1-6}$ acyl), —C(O)($C_1$-$C_6$ alkyl), —C(O)($C_1$-$C_6$ haloalkyl), —C(O)(phenyl), —C(O)(non-aromatic heterocyclic group), —C(O)O($C_1$-$C_6$ alkyl), —C(O)O($C_1$-$C_6$ haloalkyl), —C(O)O(phenyl), —OC(O)($C_1$-$C_6$ alkyl), —OC(O)($C_1$-$C_6$ haloalkyl), —OC(O)(phenyl), —S(O)$_2$($C_{1-6}$ alkyl), —S(O)$_2$($C_{1-6}$ haloalkyl), and —S(O)$_2$(phenyl);

each $Ar^{10}$ independently is a $C_{6-14}$ aryl group or a 5-14 membered heteroaryl group, each optionally and independently substituted with one or more substituents selected from the group consisting of halogen, nitro, cyano, —OH, —SH, —O($C_{1-10}$ alkyl), —S($C_{1-10}$ alkyl), $C_{1-10}$ alkyl, $C_{1-10}$ haloalkyl, $(C_{1-10}$ haloalkoxy)$C_{1-10}$ alkyl, $(C_{1-10}$ alkoxy)$C_{1-10}$ alkyl, $C_{1-10}$ hydroxyalkyl, $(C_{1-10}$ aminoalkyl, $(C_{1-10}$ alkylamino)$C_{1-40}$ alkyl, $(C_{1-10}$ dialkylamino)$C_{1-10}$ alkyl, (phenyl)$C_{1-10}$ alkyl, (5-6 membered heteroaryl)$C_{1-10}$ alkyl, amino, $C_{1-10}$ alkylamino, $C_{1-10}$ dialkylamino, $C_{1-10}$ haloalkoxy, $C_{1-10}$ alkylcarbonyloxy, $C_{1-10}$ alkoxycarbonyl and $C_{1-10}$ alkylcarbonyl;

each p is 1, 2 or 3; and each q is 2, 3, 4 or 5.

8. The method of claim 7, wherein the PLK-4 antagonist is represented by a structural formula selected from:

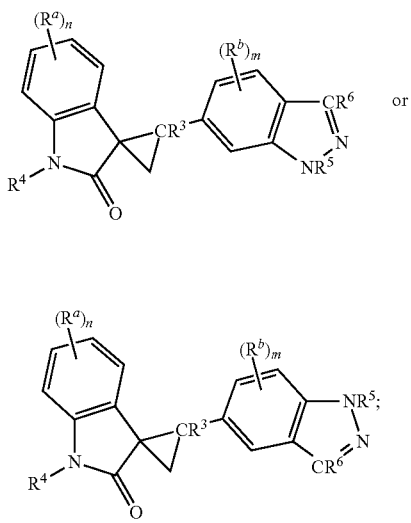

or a pharmaceutically acceptable salt thereof, wherein each n is 0, 1, 2, or 3; and each m is 0, 1, or 2.

9. The method of claim 8, wherein the PLK-4 antagonist is represented by structural formula (X):

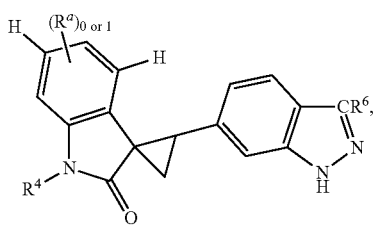

or a pharmaceutically acceptable salt thereof.

10. The method of claim 9, wherein the PLK-4 antagonist is represented by structural formula (Xb):

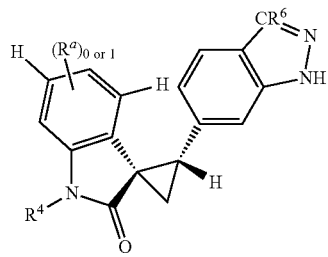

or a pharmaceutically acceptable salt thereof.

11. The method of claim 9, wherein $R^6$ is —C≡C-(optionally substituted phenyl).

12. The method of claim 11, wherein the phenyl in —CH=CH-(phenyl) is optionally substituted with one or more substituents independently selected from the group consisting of halogen, $C_{1-6}$ alkyl, $C_{1-6}$ haloalkyl, ($C_{1-6}$ aminoalkyl), ($C_{1-6}$ alkylamino)$C_{1-6}$ alkyl, ($C_{1-6}$ dialkylamino) $C_{1-6}$ alkyl, (phenyl)$C_{1-6}$ alkyl, amino, $C_{1-6}$ alkylamino, $C_{1-6}$ dialkylamino, —$(CH_2)_{0-3}$—N-piperidinyl, —$(CH_2)_{0-3}$—N-morpholinyl, —$(CH_2)_{0-3}$—N-pyrrolidinyl, —$(CH_2)_{0-3}$—N-piperazinyl and —$(CH_2)_{0-3}$—N-oxazepanyl, wherein the N-piperazinyl is optionally N'-substituted with $C_{1-6}$ alkyl or $C_{1-6}$ acyl.

13. The method of claim 11, wherein $R^4$ is —H, $C_1$-$C_6$ alkyl, phenyl, —C(O)($C_1$-$C_6$ alkyl), —C(O)(phenyl), —C(O)O($C_1$-$C_6$ alkyl), —C(O)O(phenyl), —S(O)$_2$($C_1$-$C_6$ alkyl) or —S(O)$_2$(phenyl).

14. The method of claim 13, wherein $R^a$ is halogen, —NH$_2$, ($C_{1-6}$ alkyl)amine or $C_{1-6}$ alkoxy.

15. The method of claim 1, wherein the PLK-4 antagonist is represented by the following structural formula:

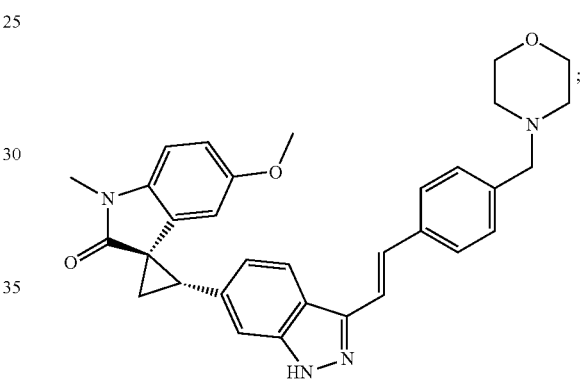

or a pharmaceutically acceptable salt thereof.

16. The method of claim 1, wherein the PLK-4 antagonist is represented by the following structural formula:

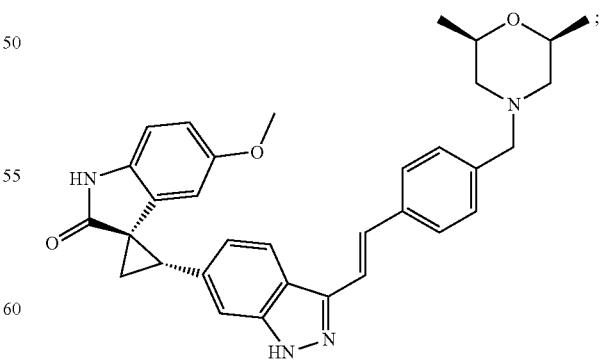

or a pharmaceutically acceptable salt thereof.

17. The method of claim 1, wherein the PLK-4 antagonist is represented by the following structural formula:

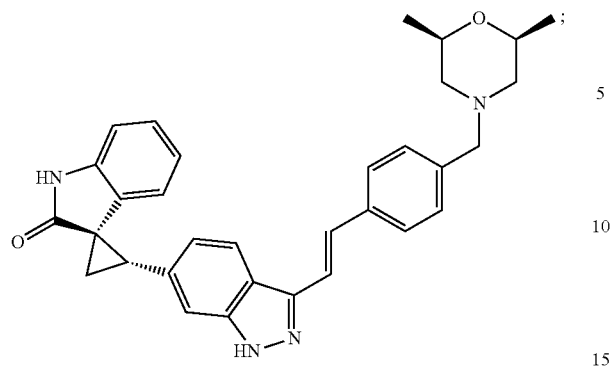
or a pharmaceutically acceptable salt thereof.
\* \* \* \* \*

UNITED STATES PATENT AND TRADEMARK OFFICE
CERTIFICATE OF CORRECTION

PATENT NO. : 8,933,070 B2  
APPLICATION NO. : 13/807816  
DATED : January 13, 2015  
INVENTOR(S) : Pan et al.

Page 1 of 1

It is certified that error appears in the above-identified patent and that said Letters Patent is hereby corrected as shown below:

In the Claims:

Column 84, claim 7, line 61, replace "SOW" with --SOR'--;

Column 86, claim 7, line 60, replace "($C_{1-10}$ alkylamino)$C_{1-40}$ alkyl" with --($C_{1-10}$ alkylamino$C_{1-10}$ alkyl--.

Signed and Sealed this  
Twenty-sixth Day of May, 2015

Michelle K. Lee  
*Director of the United States Patent and Trademark Office*